(12) United States Patent
Mensa-Wilmot

(10) Patent No.: US 8,246,966 B2
(45) Date of Patent: Aug. 21, 2012

(54) TRYPANOSOME MICROSOME SYSTEM AND USES THEREOF

(75) Inventor: Kojo Mensa-Wilmot, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 108 days.

(21) Appl. No.: 12/367,093

(22) Filed: Feb. 6, 2009

(65) Prior Publication Data

US 2009/0202625 A1 Aug. 13, 2009

Related U.S. Application Data

(63) Continuation-in-part of application No. PCT/US2007/017555, filed on Aug. 7, 2007.

(60) Provisional application No. 61/094,457, filed on Sep. 5, 2008, provisional application No. 60/836,045, filed on Aug. 7, 2006.

(51) Int. Cl.
*A61K 39/00* (2006.01)
*C12Q 1/18* (2006.01)

(52) U.S. Cl. .................................. 424/269.1; 435/32

(58) Field of Classification Search ............................ None
See application file for complete search history.

(56) References Cited

U.S. PATENT DOCUMENTS

| | | | |
|---|---|---|---|
| 3,470,182 A | 9/1969 | Hardtmann et al. |
| 3,551,427 A | 12/1970 | Ott et al. |
| 3,772,295 A | 11/1973 | Robba et al. |
| 3,800,039 A | 3/1974 | Marquis et al. |
| 4,343,940 A | 8/1982 | Kreighbaum et al. |
| 4,464,375 A | 8/1984 | Kobayashi et al. |
| 5,521,184 A | 5/1996 | Zimmermann |
| 5,618,829 A | 4/1997 | Takayanagi et al. |
| 5,639,757 A | 6/1997 | Dow et al. |
| 5,656,643 A | 8/1997 | Spada et al. |
| 5,710,158 A | 1/1998 | Myers et al. |
| 5,714,493 A | 2/1998 | Myers et al. |
| 5,721,237 A | 2/1998 | Myers et al. |
| 5,728,868 A | 3/1998 | Springer et al. |
| 5,792,783 A | 8/1998 | Tang et al. |
| 5,804,396 A | 9/1998 | Plowman |
| 5,834,504 A | 11/1998 | Tang et al. |
| 5,874,242 A * | 2/1999 | Mensa-Wilmot ............ 435/69.1 |
| 5,883,113 A | 3/1999 | Tang et al. |
| 5,883,116 A | 3/1999 | Tang et al. |
| 5,886,020 A | 3/1999 | Tang et al. |
| 6,100,254 A | 8/2000 | Budde et al. |
| 6,127,374 A | 10/2000 | Bridges |
| 6,245,759 B1 | 6/2001 | Bilodeau et al. |
| 6,306,874 B1 | 10/2001 | Fraley et al. |
| 6,313,138 B1 | 11/2001 | Fraley et al. |
| 6,316,444 B1 | 11/2001 | Hunt et al. |
| 6,329,380 B1 | 12/2001 | Goulet et al. |
| 6,344,459 B1 | 2/2002 | Bridges et al. |
| 6,420,382 B2 | 7/2002 | Fraley et al. |
| 6,479,512 B1 | 11/2002 | Fraley et al. |
| 6,498,165 B1 | 12/2002 | Armstrong et al. |
| 6,544,988 B1 | 4/2003 | Bilodeau et al. |
| 6,562,818 B1 | 5/2003 | Bridges |
| 6,586,423 B2 | 7/2003 | Bilodeau et al. |
| 6,586,424 B2 | 7/2003 | Bilodeau et al. |
| 6,740,665 B1 | 5/2004 | Murali et al. |
| 6,794,393 B1 | 9/2004 | Fraley et al. |
| 6,875,767 B2 | 4/2005 | Bilodeau et al. |
| 6,927,293 B2 | 8/2005 | Kim et al. |
| 6,958,340 B2 | 10/2005 | Bilodeau et al. |
| 6,984,389 B2 | 1/2006 | Li |
| 7,189,820 B2 | 3/2007 | Ruben |
| 2001/0044451 A1 | 11/2001 | Fraley et al. |
| 2001/0047007 A1 | 11/2001 | Fraley et al. |
| 2002/0147203 A1 | 10/2002 | Bilodeau et al. |
| 2003/0059862 A1 | 3/2003 | Ruben |
| 2003/0064996 A1 | 4/2003 | Bilodeau et al. |
| 2003/0092145 A1 | 5/2003 | Jira et al. |
| 2003/0100567 A1 | 5/2003 | Bilodeau et al. |
| 2003/0203846 A1 | 10/2003 | Srivstava et al. |
| 2004/0192725 A1 | 9/2004 | Kim et al. |
| 2004/0220201 A1 | 11/2004 | Bilodeau et al. |
| 2005/0096344 A1 | 5/2005 | Fraley et al. |
| 2007/0160603 A1 | 7/2007 | Ruben |
| 2008/0274107 A1 | 11/2008 | Fraley et al. |
| 2009/0202625 A1 * | 8/2009 | Mensa-Wilmot ............. 424/450 |

FOREIGN PATENT DOCUMENTS

| | | |
|---|---|---|
| EP | 0 520 722 A1 | 12/1992 |
| EP | 0 602 851 A1 | 6/1994 |
| EP | 0 602 851 B1 | 1/1996 |
| EP | 0 520 722 B1 | 12/1996 |
| EP | 0 584 222 B1 | 10/1997 |
| EP | 1 262 556 A2 | 12/2002 |
| WO | WO 92/20642 A1 | 11/1992 |
| WO | WO 95/15758 A1 | 6/1995 |
| WO | WO 96/40116 A1 | 12/1996 |
| WO | WO 99/03854 A1 | 1/1999 |
| WO | WO 00/38519 A1 | 7/2000 |

(Continued)

OTHER PUBLICATIONS

Taylor et al, TRENDS in Genetics, Aug. 2006, 22/11:614-620.*
Duszenko et al, Eur. J. Biochem., 1999, 266:789-797.*
U.S. Appl. No. 12/446,286, filed Nov. 21, 2007, Mensa-Wilmont.
Abrahmsen et al., "Analysis of signals for secretion in the staphylococcal protein A gene," Dec. 30, 1985 *EMBO J.* 4(13B):3901-3906.
Abrams et al., "SU11248 inhibits KIT and platelet-derived growth factor receptor β in preclinical models of human small cell lunch cancer," May 2003 *Mol Cancer Ther.* 2(5):471-478.

(Continued)

*Primary Examiner* — Nita M Minnifield

(74) *Attorney, Agent, or Firm* — Mueting Raasch & Gebhardt, P.A.

(57) ABSTRACT

The present invention provides cell free preparations of protozoan microsomes, wherein the cell free preparation of protozoan microsomes demonstrate the ability to translocate a protozoan polypeptide into the microsome, methods of preparing cell free preparations of protozoan microsomes, and methods of using cell free preparations of protozoan microsomes.

17 Claims, 25 Drawing Sheets

FOREIGN PATENT DOCUMENTS

| | | |
|---|---|---|
| WO | WO 2008/006085 A2 | 1/2008 |
| WO | WO 2008/021092 A2 * | 2/2008 |
| WO | WO 2008/066755 A2 | 6/2008 |
| WO | WO 2008/066755 A3 | 1/2009 |
| WO | WO 2008/006085 A3 | 4/2009 |

OTHER PUBLICATIONS

Akiyama et al., "Genistein, a specific inhibitor of tyrosine-specific protein kinases," Apr. 25, 1987 *J. Biol. Chem.* 262(12):5592.

Albuschat et al., "4-anilinoquinazolines with Lavendustin A subunit as inhibitors of epidermal growth factor receptor tyrosine kinase: syntheses, chemical and pharmacological properties," Dec. 2004 *Eur. J. Med. Chem.* 39(12):1001-1011.

Al-Qahtani and Mensa-Wilmot, "A 5' untranslated region which directs accurate and robust translation by prokaryotic and mammalian ribosomes," Mar. 15, 1996 *Nucleic Acid Res.* 24(6):1173-1174.

Al-Qahtani et al., "Species-specificity in endoplasmic reticulum signal peptide utilization revealed by proteins from *Trypanosoma brucei* and *Leishmania*," Apr. 15, 1998 *Biochem J.* 331(Pt 2):521-529.

Alberts et al., *Molecular Biology of the Cell 3rd Edition*. Garland Publishing: New York, NY. 1994. Cover page, publishers page and pp. 577-594.

Anafi et al., "Selective interactions of transforming and normal *abl* proteins with ATP, tyrosine-copolymer substrates, and tyrphostins," Mar. 5, 1992 *J. Biol. Chem.* 26(7)7:4518-4523.

Aparna et al., "Virtual screening of 4-anilinoquinazoline analogues as EGFR kinase inhibitor: importance of hydrogen bonds in the evaluation of poses and scoring functions," May-Jun. 2005 *J. Chem. Inf. Model* 45(3):725-738.

Assefa et al., "3D-QSAR and docking studies on 4-anilinoquinazoline and 4-anilinoquinoline epidemial growth factor receptor (EGR) tyrosine kinase inhibitors," Aug. 2003 *J. Comput. Aided Mol. Des.* 17(8):475-493.

Attoub et al., "The c-kit tyrosine kinase inhibitor STI571 for colorectal cancer therapy," Sep. 1, 2002 *Cancer Res.* 62(17):4879-4883.

Axitinib product datasheet [online] Pfizer Oncology; New York, NY. Published in 2008 [retrieved on May 18, 2009]. Retrieved from the Internet: <http://media.pfizer.com/files/news/asco/axitinib_fact_sheet_2008.pdf>; 1 pg.

"Axitinib shows promise in treatment of advanced thyroid cancer," Jun. 7, 2007 *News-Medical.Net*. Available online [retrieved on Nov. 16, 2007]. Retrieved from the Internet: <http://www.news-medical.net/print_article.asp?id=26022>; 2 pgs.

Bangs et al., "Posttranslational modification and intracellular transport of a trypanosome variant surface glycoprotein," Jul. 1986 *J. Cell Biol.* 103(1):255-263.

Bangs et al., "A soluble secretory reporter system in *Trypanosoma brucei*. Studies on endoplasmic reticulum targeting," Aug. 2, 1996 *J. Biol. Chem.* 271(31):18387-18393.

Barrett et al., "Recent advances in identifying and validating drug targets in trypanosomes and leishmanias," Feb. 1999 *Trends Microbiol.* 7(2):82-88.

Barrett and Barrett, "Anti-sleeping sickness drugs and cancer chemotherapy," Jan. 2000 *Parasitol. Today* 16(1):7-9.

Barrett et al., "Human African trypanosomiases: pharmacological re-engagement with a neglected disease," Dec. 2007 *Br. J. Pharmacol.* 152(8):1155-1171. Available online on Jul. 9, 2007.

Barrett et al., "The discovery of the benzhydroxamate MEK inhibitors CI-1040 and PD 0325901," Dec. 15, 2008 *Bioorg. Med. Chem. Lett.* 18(24):6501-6504. Available online on Oct. 15, 2008.

Batra et al., "Epidermal growth factor ligand-independent, unregulated, cell-transforming potential of a naturally occurring human mutant *EGFRvIII* gene," Oct. 1995 *Cell Growth Diff.* 6(10):1251-1259.

Becker et al., "Functional interaction of cytosolic hsp70 and a DnaJ-related protein, Ydjlp, in protein translocation in vivo," Aug. 1996 *Mol. Cell Biol.* 16(8):4378-4386.

Besemer et al., "Selective inhibition of cotranslational translocation of vascular cell adhesion molecule 1," Jul. 14, 2005 *Nature* 436(7048):290-293.

Bilder et al., "Tyrphostins inhibit PDGF-induced DNA synthesis and associated early events in smooth muscle cells," Apr. 1991 *Am. Jr. Physiol.—Cell Physiol.* 260:C721-C730.

Bird et al., "Translocation in yeast and mammalian cells: not all signal sequences are functionally equivalent," Dec. 1987 *J. Cell Biol.* 105(6 Pt2):2905-2914.

Bleasdale et al., "Small molecule peptidomimetics containing a novel phosphotyrosine biosostere inhibit protein tyrosine phosphatase 1B and augment insulin action," May 15, 2001 *Biochem.* 40(19):5642-5654.

Bowler et al., "How azide inhibits ATP hydrolysis by the F-ATPases," Jun. 6, 2006 *PNAS* 103(23):8646-8649. Available online on May 25, 2006.

Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor," Jan. 5, 1996 *J. Med. Chem.* 39:267.

Brodsky et al., "Reconstitution of protein translocation from solubilized yeast membranes reveals topologically distinct roles for BiP and cytosolic Hsc70," Jan. 1993 *J. Cell Biol.* 120(1):95-102.

Brodsky et al., "BiP and Sec63p are required for both co- and post-translational protein translocation into the yeast endoplasmic reticulum," Oct. 10, 1995 *PNAS* 92(21):9643-9646.

Brodsky and Chiosis, "Hsp70 molecular chaperones: emerging roles in human disease and identification of small molecule modulators," 2006 *Curr. Top. Med. Chem.* 6(11):1215-1225.

Broniscer et al., "Plasma and cerebrospinal fluid pharmacokinetics of erlotinib and its active metabolite OSI-420," Mar. 1, 2007 *Clin. Cancer Res.* 13(5):1511-1515.

Bruch and Gierasch, "Comparison of helix stability in wild-type and mutant LamB signal sequences," Mar. 5, 1990 *J. Biol. Chem.* 265(7):3851-3858.

Bryckaert et al., "Inhibition of platelet-derived growth factor-induced mitogenesis and tyrosine kinase activity in cultured bone marrow fibroblasts by tyrphostins," Apr. 1992 *Exp. Cell Res.* 199(2):255-261.

Burke et al., "A short stereoselective total synthesis of the fusarium toxin equisetin," Nov. 16, 2000 *Org. Lett.* 2(23):3611-3613.

Button et al., "Recombinant *Leishmania* surface glycoprotein GP63 is secreted in the baculovirus expression system as a latent metalloproteinase," Nov. 30, 1993 *Gene* 134(1):75-81.

Cabebe and Wakelee, "Sunitinib: a newly approved small-molecule inhibitor of angiogenesis," Jun. 2006 *Drugs Today* 42(6):387-398.

Carter et al., "Inhibition of drug-resistance mutants of ABL, KIT, and EGF receptor kinases," Aug. 2, 2005 *PNAS* 102(31):11011-11016. Available online on Jul. 26, 2005.

Chen et al., "Synthesis and structure-activity studies of a series of [(hyroxybenzyl)amino]salicylates as inhibitors of EGF receptor-associated tyrosine kinase activity," Dec. 10, 1993 *J. Med. Chem.* 36(25):4094-4098.

Chen et al., "Competition between functional signal eptides demonstrates variation in affinity for the secretion pathway," Dec. 1996 *J. Bacteriol.* 178(23):6658-6664.

Chini et al., "Evidence that the cADPR signaling pathway controls calcium-mediated microneme secretion in *Toxoplasma gondii*," 2005 *Biochem J.* 389:269-277.

Chopard et al., "Quantitative analysis of relative protein contents by Western blotting: comparison of three members of the dystrophin-glycoprotein complex in slow and fast rat skeletal muscle," Feb. 2000 *Electrophoresis* 21(3):517-522.

Chou and Kendall, "Polymeric sequences reveal a functional interrelationship between hydrophobicity and length of signal peptides," Feb. 15, 1990 *J. Biol. Chem.* 265(5):2873-2880.

Chu et al., "Receptor dimerization is not a factor in the signalling activity of transforming variant epidermal growth factor receptor (EGFRvIII)," Jun. 15, 1997 *Biochem. J.* 324(Pt 3):855-861.

Szende et al., "Tryphostin induces non-apoptotic programmed cell death in colon tumor cells," Nov. 1995 *Cell Biol. Int.* 19(11):903-912.

Tasigna® (nilotinib) product website "Tasigna education" [online]. Novartis Oncology; New Hanover, NJ. Copyright 2007 [retrieved on Apr. 28, 2009]. Retrieved from the Internet: <http://www.us.tasigna.com/info/about-tasigna.jsp?printmode=true>; 3 pgs.

Taylor and Rudenko, "Switching trypanosome coats: what's in the wardrobe?" Nov. 2006 *Trends Genet.* 22(11):614-620. Available online on Aug. 14, 2006.

Teilhet et al., "Effect of short 5' UTRs on protein synthesis in two biological kingdoms," Nov. 5, 1998 *Gene* 222(1):91-97.

Thompson and Schultz, "Enzymatic properties of microsomal membranes from the protozoan *Acanthamoeba castellanii*," 1971 *Exp. Cell Res.* 68:106-112.

Tomilo et al., "Can a signal sequence become too hydrophobic?" Dec. 16, 1994 *J. Biol. Chem.* 269(50):32016-32021.

Traxler et al., "Use of a pharmacophore model for the design of EGF-R tyrosine kinase inhibitors: 4-(phenylamino)pyrazolo[3,4-d]pyrimidines," Oct. 24, 1997 *J. Med. Chem.* 40(22):3601-3616. Abstract published on Sep. 15, 1997.

Traxler et al., "AEE788: a dual family epidermal growth factor receptor/ErbB2 and vascular endothelial growth factor receptor tyrosine kinase inhibitor with antitumor and antiangiogenic activity," Jul. 15, 2004 *Cancer Res.* 64(14):4931-4941.

Tsou et al., "Optimization of 6,7-disubstituted-4-(arylamino)quinoline-3-carbonitriles as orally active, irreversible inhibitors of human epidermal growth factor receptor-2 kinase activity," Feb. 24, 2005 *J. Med. Chem.* 48(4):1107-1131. Available online on Jan. 27, 2005.

Turbov et al., "Effects of receptor tyrosine kinase inhibitor A47 on estrogen and growth factor-dependent breast cancer cell proliferation and apoptosis in vitro," Jan. 2002 *J. Surg. Oncol.* 79(1):17-29.

Twaddle et al., "Tyrosine kinase inhibitors as antiproliferative agents against an estrogen-dependent breast cancer cell line in vitro," Feb. 1999 *J. Surg. Oncol.* 70(2):83-90.

Tykerb® (lapatinib) product website "I want more information about Tykerb®" [online]. GlaxoSmithKline Oncology; Brentford, Middlesex UK. Copyright 1997-2009 [retrieved on Apr. 28, 2009]. Retrieved from the Internet: <http://www.tykerb.com/about-tykerb/about-tykerb.html#>; 2 pgs.

"Tyrosine kinase inhibitors," Parker Hughes Institute: St. Paul, MN; copyright 2000. No longer available online [retrieved on Aug. 4, 2006]. Retrieved from the Internet: <www.ih.org/pages/tyrosine_kinase_inhibitors.html>; 2 pgs.

Tzivelka et al., "Natural products with anti-HIV activity from marine organisms," 2003 *Curr. Top. Med. Chem.* 3(13):1512-1535.

Uehara et al., "Irreversible inhibition of v-src tyrosine kinase activity by herbimycin A and its abrogation by sulfhydryl compounds," Sep. 15, 1989 *Biochem. Biophys. Res. Comm.* 163(2):803-809.

Uings et al., "Tyrosine phosphorylation is involved in receptor coupling to phospholipase D but not phospholipase C in the human neutrophil," Feb. 1, 1992 *Biochem. J.* 281(Pt 3):597-600.

Ullers et al., "SecB is a bona fide generalized chaperone in *Escherichia coli*," May 18, 2004 *PNAS* 101(20):7583-7588. Available online on May 5, 2004.

Van de Casteele et al., "Prolonged culture in low glucose induces apoptosis of rat pancreatic β-cells through induction of c-myc," Dec. 26, 2003 *Biochem. Biophys. Res. Comm.* 312(4):937-944.

Van den Berg et al., "X-ray structure of a protein-conducting channel," Jan. 1, 2004 *Nature* 427(6969):36-44. Available online on Dec. 3, 2003.

Van der Ploeg et al., "Heat shock genes: regulatory role for differentiation in parasitic protozoa," Jun. 21, 1985 *Science* 228(4706):1443-1446.

Van der Wolk et al., "The catalytic cycle of the *Escherichia coli* SecA ATPase comprises two distinct preprotein translation events," Dec. 15, 1997 *EMBO J.* 16(24):7297-7304.

Von Heijne, "On the hydrophobic nature of signal sequences," May 15, 1981 *Eur. J. Biochem.* 116(2):419-422.

Von Heijne, "Signal sequences. The limits of variation," Jul. 5, 1985 *J. Mol. Biol.* 184(1):99-105.

Von Heijne and Abrahmsen, "Species-specific variation in signal sequence peptide design. Implications for protein secretion in foreign hosts," Feb. 27, 1989 *FEBS Lett.* 244(2):439-446.

Walter and Blobel, "Translocation of proteins across the endoplasmic reticulum III. Signal recognition protein (SRP) causes signal sequence-dependent and site-specific arrest of chain elongation that is released by microsomal membranes," Nov. 1, 1981 *J. Cell. Biol.* 91(2 Pt 1):557-561.

Walter and Johnson, "Signal sequence recognition and protein targeting to the endoplasmic reticulum membrane," 1994 *Ann. Rev. Cell Biol.* 10:87-119.

Watanabe and Blobel, "SecA protein is required for translocation of a model precursor protein into inverted vesicles of *Escherichia coli* plasma membrane," Oct. 1, 1993 *PNAS* 90:9011-9015.

Waters et al., "Protein translocation across the yeast microsomal membrane is stimulated by a soluble factor," Dec. 1, 1986 *J. Cell Biol.* 103(6 Pt 2):2629-2636.

Wessely et al., "Distinct roles of the receptor tyrosine kinases c-ErbB and c-Kit in regulating the balance between erythroid cell proliferation and differentiation," May 1997 *Cell Growth Diff.* 8(5):481-493.

Wickner and Schekman, "Protein translocation across biological membranes," Dec. 2, 2005 *Science* 310(5753):1452-1456.

Wiedmann et al., "Post-translational transport of proteins into microsomal membranes of *Candida maltosa*," Jun. 1988 *EMBO J.* 7(6):1763-1768.

Wigg et al., "Assessment of cell concentration and viability of isolated hepatocytes using flow cytometry," Jun. 1, 2003 *Anal. Biochem.* 317(1):19-25.

Wikstrand et al., "Cell surface localization and density of the tumor-associated variant of the epidermal growth factor receptor, EGFRvIII," Sep. 15, 1997 *Cancer Res.* 57(18):4130-4140.

Williams, "Prof looks for parasite's 'Achilles heel'," in *University of Georgia Columns*. Jan. 27, 1997 UGA People. Available online [retrieved on Jul. 20, 2006]. Retrieved from the Internet: <http://www.uga.edu/columns/012797/people1.html>; 2 pgs.

Wissner et al., "Dual irreversible kinase inhibitors: quinazoline-based inhibitors incorporating two independent reactive centers with each targeting different cysteine residues in the kinase domains of EGFR and VEGFR-2," Jun. 1, 2007 *Bioorg. Med. Chem.* 15(11):3635-3648. Available online on Mar. 23, 2007.

Wolbring et al., "Inhibition of GTP-utilizing enzymes by tyrphostins," Sep. 9, 1994 *J. Biol. Chem.* 269(36):22470-22472.

Wright et al., "Pyrimidinone-peptoid hybrid molecules with distinct effects on molecular chaperone function and cell proliferation," Mar. 15, 2008 *Bioorg. Med. Chem.* 16(6):3291-3301. Available online on Dec. 14, 2007.

Xu et al., "Inhibition of protein tyrosine phosphorylation in T cells by a novel immunosuppressive agent, leflunomide," May 26, 1995 *J. Biol. Chem.* 270(21):12398-12403.

Yang et al., "Butein, a specific protein tyrosine kinase inhibitor," Apr. 17, 1998 *Bioc. Biophys. Res. Comm.* 245(2):435-438.

Yazici et al., "Dual inhibition of the epidermal growth factor and vascular endothelial growth factor phosphorylation for antivascular therapy of human prostate cancer in the prostate of nude mice," Nov. 1, 2005 *Prostate* 65(3):203-215. Available online on Jun. 9, 2005.

Yen et al., "Enhanced cell differentiation when RB is hypophosphorylated and down-regulated by radicicol, a SRC-kinase inhibitor," Sep. 1994 *Exp. Cell Res.* 214(1):163-171.

Yermovsky-Kammerer and Hajduk, "In vitro import of a nuclearly encoded tRNA into the mitochondrion of *Trypanosoma brucei*," Sep. 1999 *Mol. Cell Biol.* 19(9):6253-6259.

Yoneda et al., "The antiproliferative effects of tyrosine kinase inhibitors tyrphostins on a human squamous cell carcinoma in vitro and in nude mice," Aug. 15, 1991 *Cancer Res.* 51(16):4430-4435.

Zhang et al., "Hsp70 molecular chaperone facilitates endoplasmic reticulum-associated protein degradation of cystic fibrosis transmembrane conductance regulator in yeast," May 2001 *Mol. Biol. Cell* 12(5):1303-1314.

Zheng and Gierasch, "Signal sequences: the same yet different," Sep. 20, 1996 *Cell* 86(6):849-852.

Zheng and Nicchitta, "Structural determinants for signal sequence function in the mammalian endoplasmic reticulum," Dec. 17, 1999 *J. Biol. Chem.* 274(51):36623-36630.

Zheng et al., "Endosomes, glycosomes, and glycosylphosphatidylinositol catabolism in *Leishmania major*," Oct. 1, 2004 *J. Biol. Chem.* 279(40):42106-42113. Available online on Jul. 14, 2004.

Zheng et al., "Intracellular glycosylphosphatidylinositols accumulate on endosomes: toxicity of alpha-toxin to *Leishmania major*," Mar. 2005 *Eukaryot. Cell* 4(3):556-566.

Zheng et al., "Phosphotyrosine proteomic study of interferon α signaling pathway using a combination of immunoprecipitation and immobilized metal affinity chromatography," Jun. 2005 *Mol. Cell Proteomics* 4(6):721-730. Available online on Jan. 19, 2005.

Zhou and Xu, "Structural determinants of SecB recognition by SecA in bacterial protein translocation," Nov. 2003 *Nat. Struct. Biol.* 10(11):942-947. Available online on Sep. 28, 2003.

Zhu et al., "EGFR tyrosine kinase inhibitor AG1478 inhibits cell proliferation and arrests cell cycle in nasopharyngeal carcinoma cells," Aug. 10, 2001 *Cancer Lett.* 169(1):27-32.

de la Canal, et al. "Synthesis of Dolichol Derivatives in Trypanosmatids Characterization of Enzymatic Patterns," 1987. Journal of Biological Chemistry. pp. 11128-11133.

El Moudni et al., "Purification and Characterization of N-Acetylglucosaminidase from *Trypanosoma cruzi*," 1996. Experimental Parasitology, 83, 167-173. Article No. 0063.

Vidugiriene et al. "The GPI Anchor of Cell-Surface Proteins Is Synthesized on the Cytoplasmic Face of the Endoplasmic Reticulum," 1994. Journal of Cell Biology, 127(2):333-341.

Akita and Sliwkowski, "Preclinical studies with Erlotinib (Tarceva)," Jun. 2003 *Semin. Oncol.* 30(3 Supp. 7):15-24.

Bennett et al., "Cytochrome oxidase inhibition: a novel animal model of Alzheimer's disease," Apr.-Jun. 1992 *J. Geriatr. Psychiatry Neurol.* 5(2):93-101.

Berridge et al., "Tetrazolium dyes as tools in cell biology: new insights into their cellular reduction," 2005 *Biotechnol. Ann. Rev.* 11:127-152.

Blagosklonny et al., "Geldanamycin selectively destabilizes and conformationally alters mutated p53," Sep. 7, 1995 *Oncogene* 11(5):933.

Bolen, "Nonreceptor tyrosine protein kinases," Aug. 1993 *Oncogene* 8(8):2025-2031.

Bulgaru et al., "Erlotinib (Tarceva®): a promising drug targeting epidermal growth factor receptor tyrosine kinase," Jun. 2003 *Exp. Rev. Anticancer Ther.* 3(3):269-279.

Caplan et al., "YDJ1p facilitates polypeptide translocation across different intracellular membranes by a conserved mechanism," Dec. 24, 1992 *Cell* 71(7):1143-1155.

Chan et al., "Selective inhibition of the growth of ras-transformed human bronchial epithelial cells by emodin, a protein-tyrosine kinase inhibitor," Jun. 30, 1993 *Biochem. Biophys. Res. Comm.* 193(3):1152-1158.

Chan et al., "Three new flavonoids and antiallergic, anti-inflammatory constituents from the heartwood of *Dalbergia odorifera*," Mar. 1998 *Planta. Med.* 64:153-158.

Chirico et al., "70K heat shock related proteins stimulate protein translocation into microsomes," Apr. 28, 1988 *Nature* 332(6167):805-810.

Corbett et al., "Response of transplantable tumors of mice to anthracenedione derivatives alone and in combination with clinically useful agents," May 1982 *Cancer Treatment Reports* 66(5):1187-1200.

Cross, "Identification, purification and properties of clone-specific glycoprotein antigens constituting the surface coat of *Trypanosoma brucei*," Dec. 1975 *Parasitol.* 71(3):393-417.

Crowley et al., "Secretory proteins move through the endoplasmic reticulum membrane via an aqueous, gated pore," Aug. 12, 1994 *Cell* 78(3):461-471.

Dewji, "Early phase I data on an irreversible pan-erb inhibitor: CI-1033. What did we learn?" Nov. 2004 *J. Chemother.* 16(Supp. 4):44-48.

Fradelizi et al., "Quantitative measurement of proteins by western blotting with Cy5™—mcoupled secondary antibodies," Mar. 1999 *Biotechniques* 26(3):484, 486, 488, 490, 492-494.

Gallagher, "One-dimensional SDS gel electrophoresis of proteins," Chapter 6: Unit 6.1 in *Current Protocols in Cell Biology*; John Wiley & Sons: Hoboken, NJ. Dec. 2007. Supplement 37, pp. 6.1.1-6.1.38.

Gorlich et al., "A mammalian homolog of SEC61p and SECYp is associated with ribosomes and nascent polypeptides during translocation," Oct. 30, 1992 *Cell* 71(3):489-503.

Hamid, "Emerging treatments in oncology: focus on tyrosine kinase (erbB) receptor inhibitors," Jan.-Feb. 2004 *J. Am. Pharm Assoc.* 44(1):52-58.

Hammarton et al., "The cell cycle of parasitic protozoa: potential for chemotherapeutic exploitation," 2003 *Prog. Cell Cycle Res.* 5:91-101.

Hansen et al., "In vitro protein translocation across the yeast endoplasmic reticulum: ATP-dependent posttranslational translocation of the prepro-α-factor," May 9, 1986 *Cell* 45(3):397-406.

Hellwig et al., "Altersetin, a new antibiotic from cultures of endophytic *Alternaria* spp. Taxonomy, fermentation, isolation, structure elucidation and biological activities," Oct. 2002 *J. Antibiot* (Tokyo) 55(10):881-892.

Hirumi and Hirumi, "In vitro cultivation of *Trypanosoma conolense* bloodstream forms in the absence of feeder cell layers," Apr. 1991 *Parasitol.* 102(Pt 2):225-236.

Meydan et al., "Inhibition of acute lymphoblastic leukaemia by a Jak-2 inhibitor," Feb. 15, 1996 *Nature* 379(6566):645-648.

O'Dell et al., "Long-term potentiation in the hippocampus is blocked by tyrosine kinase inhibitors," Oct. 10, 1991 *Nature* 353(6344):558-560.

Rusch and Kendall, "Protein transport via amino-terminal targeting sequences: common themes in diverse systems," Oct.-Dec. 1995 *Mol Membr. Biol.* 12(4):295-307.

Ryan et al., "Overall signal sequence hydrophobicity determines the in vivo translocation efficiency of a herpesvirus glycoprotein," Feb. 1993 *Virus Genes* 7(1):5-21.

Schwartz et al., "Induction of the differentiated phenotype in human colon cancer cells is associated with the attenuation of subcellular tyrosine phosphorylation," 1995 *Oncol. Res.* 7(6):277-287.

Shimizu and Hendershot, "Organization of the functions and components of the endoplasmic reticulum," Chapter 4 in *Molecular Aspects of the Stress Response: Chaperones, Membranes and Networks*. Csermely and Vigh (Eds.) Landes Bioscience and Springer Science + Business Media: Boston, MA; 2007. Title page and pp. 37-46.

Simon and Blobel, "A protein-conducting channel in the endoplasmic reticulum," May 3, 1991 *Cell* 65(3):371-380.

Sugie et al., "CJ-21,058, a new SecA inhibitor isolated from a fungus," Jan. 2002 *J. Antibiot* (Tokyo) 55(1):25-29.

Umezawa et al., "Inhibition of epidermal growth factor-induced DNA synthesis by tyrosine kinase inhibitors," Jan. 29, 1990 *FEBS Lett.* 260(2):198-200.

Vesonder et al., "Equisetin, an antibiotic from *Fusarium equiseti* NRRL 5537, identified as a derivative of N-methyl-2,4-pyrrollidone," Jul. 1979 *J. Antibiot.* (Tokyo) 32(7):759-761.

Vickerman, "Developmental cycles and biology of pathogenic trypanosomes," Apr. 1985 *Br. Med. Bull.* 41(2):105-114.

Walter and Blobel, "Preparation of microsomal membranes for cotranslational protein translocation," 1983 *Methods Enzymol.* 96:84-93.

Wheeler-Alm and Shapiro, "Glycosome-associate tyrosine-phosphorylated protein in *Trypanosoma brucei*," Dec. 1993 *Trop. Med. Parasitol.* 44(4):281-284.

Wiedmann et al., "*Xenopus* oocytes can secrete bacterial β-lactamase," 1984 *Nature* 309:637-639.

Wilks, "Protein tyrosine kinase growth factor receptors and their ligands in development, differentiation, and cancer," 1993 *Adv. Cancer Res.* 60:43-73.

Woods-Ignatoski, "Immunoprecipitation and western blotting of phosphotyrosine-containing proteins," 2001 *Methods Mol. Bio.* 124:39-48.

Yamaki et al., "Inhibition of c-*myc* gene expression in murine lymphoblastoma cells by geldanamycin and herbimycin, antibiotics of benzoquinoid ansamycin group," Apr. 1989 *J. Antibiot.* (Tokyo) 42(4):604-610.

CI-1033 (Canertinib®) product website [online]. Selleck Chemicals Co., Ltd.: London, Ontario, Canada. Copyright 2009 [retrieved on May 18, 2009]. Retrieved from the Internet: <http://www.selleckchem.com/ProductDetail.asp?ProdId=S1019>; 2 pgs.

Clemons et al., "Structural insight into the protein translocation channel," Aug. 2004 *Curr. Opin. Struct. Biol.* 14(4):390-396. Available online on Jul. 21, 2004.

Connolly et al., "Access of proteinase K to partially translocated nascent polypeptides in intact and detergent-solubilized membranes," Feb. 1989 *J. Cell Biol.* 108(2):299-307.

Cowman and Crabb, "Functional genomics: identifying drug targets for parasitic diseases," Nov. 2003 *Trends Parasitol.* 19(11):538-543.

Cushman et al., "Synthesis and protein-tyrosine kinase inhibitory activities of flavonoid analogues," Feb. 1991 *J. Med. Chem.* 34(2):798-806.

Cyr and Douglas, "Differential regulation of Hsp70 subfamilies by the eukaryotic DnaJ homologue YDJ1," Apr. 1, 1994 *J. Biol. Chem.* 269(13):9798-9804.

Dai et al., "Discovery of N-(4-(3-amino-1H-indazol-4-yl)phenyl)-N'-(2-fluoro-5-methylphenl)urea (ABT-869), a 3-aminoindazole-based orally active multitargeted receptor tyrosine kinase inhibitor," Apr. 5, 2007 *J. Med. Chem.* 50(7):1584-1597. Available online on Mar. 8, 2007.

Dardonville et al., "DNA binding affmity of bisguanidine and bis(2-aminoimidazoline) derivativeswith in vivo antitrypanosomal activity," Jun. 15, 2006 *J. Med. Chem.* 49(12):3748-3752. Available online on May 23, 2006.

Das et al., "2-aminothiazole as a novel kinase inhibitor template. Structure-activity relationship studies toward the discovery of N-(2-chloro-6-methylphenyl)-2-[[6-[4-(2-hydroxyethyl)-1-piperazinyl)]-2-methyl-4-pyrimidinyl]amino)]-1,3-thiazole-5-carboxamide (dasatinib, BMS-354825) as a potent pan-Src kinase inhibitor," Nov. 16, 2006 *J. Med. Chem.* 49(23):6819-6823. Available online on Oct. 24, 2006.

De Clercq, "Current lead natural products for the chemotherapy of human immunodeficiency virus (HIV) infection," Sep. 2000 *Med. Res. Rev.* 20(5):323-349.

De Koning, "Transporters in African trypanosomes: role in drug action and resistance," May 1, 2001 *Int. J Parastiol.* 31(5-6):512-521.

Del Rayo Camacho et al., "In vitro activity of Triclisia patens and some bisbenzylisoquinoline alkaloids against *Leishmania donovani* and *Trypanosoma brucei brucei*," Aug. 2002 *Phytother. Res.* 16(5):432-436.

Denny, "The 4-anilinoquinazoline class of inhibitors of the erbB family of receptor tyrosine kinases," Jan.-Feb. 2001 *Farmaco* 56(1-2):51-56.

Detimary et al., "Two sites of glucose control of insulin release with distinct dependence on the energy state in pancreatic B-cells," Feb. 1, 1994 *Biochem J.* 297(Pt 3):455-461.

Docampo and Moreno, "Current chemotherapy of human African trypanosomiases," Jun. 2003 *Parasitol. Res.* 90(Supp. 1):S10-13. Available online on Nov. 23, 2002.

Doud et al., "Titration of protein transport activity by incremental changes in signal peptide hydorphobicity," Feb. 9, 1993 *Biochem.* 32(5):1251-1256.

Dovey et al., "Biogenesis of glycosomes on *Trypanosoma brucei*: an in vitro model of 3-phosphoglycerate kinase import," Apr. 1988 *PNAS* 85(8):2598-2602.

Driessen et al., "The structural basis of protein targeting and translocation in bacteria," Jun. 2001 *Nat. Struct. Biol.* 8(6):492-498.

Duffy, Joshua, "Protein translocation into the endoplasmic reticulum of *Trypanosoma brucei*," Doctoral Thesis; University of Georgia: Athens, GA. Dec. 2008.

El-Sayed and Donelson, "African tyrpanosomes have differentially expressed genes encoding homologues of the Leishmania GP63 surface protease," Oct. 17, 1997 *J. Biol. Chem.* 272(42):26742-26748.

Ellis et al., "Preclinical analysis of the analinoquinazoline AG1478, a specific small molecule inhibitor of EGF receptor tyrosine kinase," May 14, 2006 *Biochem Pharmacol.* 71(10):1422-1434. Available online on Mar. 7, 2006.

Fairlamb, "Chemotherapy of human African trypanosomiases: current and future prospects," Nov. 2003 *Trends Parasitol.* 19(11):488-494.

Faltynek et al., "Damnacanthal is a highly potent, selective inhibitor of p56lck tyrosine kinase activity," Sep. 26, 1995 *Biochemistry* 34(38):12404-12410.

Fekkes et al., "Preprotein transfer to the *Escherichia coli* translocase requires the co-operative binding of SecB and the signal sequence to SecA," Sep. 1998 *Mol. Microbiol.* 29(5):1179-1190.

Fewell et al., "Identification of an inhibitor of hsc70-mediated protein translocation and ATP hydrolysis," Jan. 12, 2001 *J. Biol. Chem.* 276(2):910-914. Available online on Oct. 17, 2000.

Fewell et al., "Small molecule modulators of endogenous and co-chaperone-stimulated Hsp70 ATPase activity," Dec. 3, 2004 *J. Biol. Chem.* 279(49):51131-51140. Available online on Sep. 23, 2004.

Fong et al., "SU5416 is a potent and selective inhibitor of the vascular endothelial growth factor receptor (Flk-1/KDR) that inhibits tyrosine kinase catalysis, tumor vascularization, and growth of multiple tumor types," Jan. 1, 1999 *Cancer Res.* 59(1):99-106.

Fry et al., "A specific inhibitor of the epidermal growth factor receptor tyrosine kinase," Aug. 19, 1994 *Science* 265(5175):1093-1095.

Fukazawa et al., "Specific inhibition of cytoplasmic protein tyrosine kinases by herbimycin A in vitro," Oct. 9, 1991 *Biochem. Pharmacol.* 42(9):1661-1671.

Garcia and Walter, "Full-length prepro-alpha-factor can be translocated across the mammalian microsomal membrane only if translation has not terminated," Apr. 1988 *J. Cell Biol.* 106:1043-1048.

Garrison et al., "A substrate-specific inhibitor of protein translocation into the endoplasmic reticulum," Jul. 14, 2005 *Nature* 436:285-289.

Gazit et al., "Tyrphostins I: synthesis and biological activity of protein tyrosine kinase inhibitors," Oct. 1989 *J. Med. Chem.* 32(10):2344-2352.

Gazit et al., "Tyrphostins. 2. Heterocyclic and alpha-substituted benzylidenemalononitrile tyrphostins as potent inhibitors of EGF receptor and ErbB2/ney tyrosine kinases," Jun. 1991 *J. Med. Chem.* 34(6):1896-1907.

Gelb and Hol, "Drugs to combat tropical protozoan parasites," Jul. 19, 2002 *Science* 297(5580):343-344.

Gelb et al., "Protein farnesyl and N-myristoyl transferases: piggyback medicinal chemistry targets for the development of antitrypanosomatid and antimalarial therapeutics," Feb. 2003 *Mol. Biochem. Parasitol.* 126(2):155-163.

George et al., "Antikinetoplastid antimitotic activity and metabolic stability of dinitroaninline sulfonamides and benzamides," Aug. 15, 2006 *Bioorg. Med. Chem.* 14(16):5699-5710. Available online on May 3, 2006.

Ghosh et al., "Structure-based design of potent inhibitors or EGF-receptor tyrosine kinase as anti-cancer agents," Oct. 1999 *Anticancer Drug Des.* 14(5):403-410.

Gilmore et al., "Protein Translocation Across the Endoplasmic Reticulum. I. Detection in the Microsomal Membrane of a Receptor for the Signal Recognition Particle," Nov. 1982 *J. Cell. Biol.* 95(2 Pt 1):463-469.

gleevec® (imatinib mesylate) product website "How Gleevec® works," [online]. Novartis Oncology; East Hanover, NJ. Copyright 2009 [retrieved on Apr. 28, 2009]. Retrieved from the Internet: <http://www.gleevec.com/info/ag/index.jsp?print=yes>; 1 pg.

Goldshmidt et al., "Role of protein in translocation pathways across the endoplasmic reticulum in *Trypanosoma brucei*," Nov. 14, 2008 *J. Biol. Chem.* 283(46):32085-32098. Available online on Sep. 2, 2008.

Green et al., "Inhibitors of tumor progression loci-2 (Tpl2) kinase and tumor necrosis factor alpha (TNF-alpha) production: selectivity and in vivo antiinflammotry activity of novel 8-substituted-4-anilino-6-aminoquinoline-3-carbonitriles," Sep. 20, 2007 *J. Med. Chem.* 50(19):4728-4745. Available online on Aug. 23, 2007.

Gridelli et al., "Sorafenib and sunitinib in the treatment of advanced non-small cell lung cancer," Feb. 2007 *Oncologist* 12(2):191-200.

Gull, "The cell biology of parasitism in *Trypanosoma brucei*: insights and drug targets form genomic approaches?" 2002 *Curr. Pharm. Des.* 8(4):241-256.

Haeuptle et al., A tripartite structure of the signals that determine protein insertion into the endoplasmic reticulum membrane, Apr. 1989 *J. Cell. Biol.* 108(4):1227-1236.

Hanke et al., "Discovery of a novel, potent, and Src family-selective tyrosine kinase inhibitor. Study of Lck- and FynT-dependent T cell activation," Jan. 12, 1996 *J. Biol. Chem.* 271(2):695-701.

Harant et al., "The translocation inhibitor CAM741 interferes with vascular cell adhesion molecule 1 signal peptide insertion at the translocon," Oct. 13, 2006 *J. Biol. Chem.* 281(41):30492-30502. Available online on Aug. 16, 2006.

Harant et al., "Inhibition of vascular endothelial growth factor cotranlsational translocation by the cyclopeptolide CAM741," Jun. 2007 *Mol. Pharmacol.* 71(6):1657-1665. Available online on Mar. 16, 2007.

Hegde and Bernstein, "The surprising complexity of signal sequences," Oct. 2006 *Trends Biochem. Sci.* 31(10):563-571. Available online on Aug. 21, 2006.

Hennequin et al., Novel 4-anilinoquinazolines with C-6 carbon-linked side chains: synthesis and structure-activity relationship of a series of potent, orally active, EGF receptor tyrosine kinase, May 15, 2006 *Bioorg. Med. Chem. Lett.* 16(10):2672-2676. Available online on Mar. 3, 2006.

Heymach et al., "Epidermal growth factor receptor inhibitors in development for the treatment of non-small cell lung cancer," Jul. 15, 2006 *Clin.Cancer Res.* 12(14 Pt 2):4441s-4445s.

Himpens et al., "Modulation of nucleocytosolic [Ca2+] gradient in smooth muscle by protein phosphorylation," Aug. 1994 *FASEB J.* 8(11):879-883.

Hirumi and Hirumi, "Axenic culture of African trypanosome bloodstream forms," Feb. 1994 *Parasitol. Today* 10(2):80-84.

Holkeri et al., "Dissection of the translocation and chaperoning functions of yeast BiP/Kar2p in vivo," Mar. 1998 *J. Cell Sci.* 111(Pt 6):749-757. Available online on Feb. 23, 1998.

Hubbard and Till, "Protein tyrosine kinase structure and function," 2000 *Ann. Rev. Biochem.* 69:373-398.

Innis et al., "DNA sequencing with Thermus aquaticus DNA polymerase and direct sequencing of polymerase chain reaction-ampled DNA," Dec. 1988 *PNAS* 85(24):9436-9440.

International Preliminary Report on Patentability issued on Feb. 10, 2009, in PCT/US2007/017555; 6 pgs.

International Preliminary Report on Patentability issued on May 26, 2009, in PCT/US2007/024319; 6 pgs.

Nwaka and Hudson, "Innovative lead discovery strategies for tropical diseases," Nov. 2006 *Nat. Rev. Drug. Discov.* 5(11):941-955. Available online on Oct. 13, 2006.

Nyrén and Strid, "The effect of equestin on energy-linked reactions in *Rhodospirillium rubrum* chromatophores," Feb. 1, 1989 *Arch. Biochem. Biophys.* 268(2):659-666.

O'Farrell et al., "SU11248 is a novel FLT3 tyrosine kinase inhibitor with potent activity in vitro and in vivo," May 1, 2003 *Blood* 101(9):3597-3605. Available online on Jan. 16, 2003.

Ohmichi et al., "The tyrosine kinase inhibitor tyrphostin blocks the cellular actions of nerve growth factor," May 4, 1993 *Biochem.* 32(17):4650. Available online on May 1, 1993.

Okamoto et al., "Expression of constitutively activated EGFRvIII in non-small cell lung cancer," Jan. 2003 *Cancer Sci.* 94:(1)50-56.

Oliver et al., "Azide-resistant mutants of *Escherichia coli* alter the SecA protein, an azide-sensitive component of the protein export machinery," Nov. 1990 *PNAS* 87(21):8227-8231.

Oliver et al., "Inhibition of mast cell FceR1-mediated signaling and effector function by the Syk-selective inhibitor, piceatannol," Nov. 25, 1994 *J. Biol. Chem.* 269(47):29697-29703.

Oliver et al., "The Sec61 complex is essential for the insertion of proteins into the membrane of the endoplasmic reticulum," Apr. 3, 1995 *FEBS Lett.* 362:126-130.

Onoda et al., "Isolation of a novel tyrosine kinase inhibitor, lavendustin A, from *Streptomyces griseolavendus*," Nov.-Dec. 1989 *J. Nat. Prod.* 52(6):1252-1257. Available online on Nov. 1, 1989.

Osherov et al., "Selective inhibition of the epidermal growth factor and HER2/neu receptors by tyrphostins," May 25, 1993 *J. Biol. Chem.* 268(15):11134-11142.

Ouellette, "Biochemical and molecular mechanisms of drug resistance in parasites," Nov. 2001 *Trop. Med. Int. Health* 6(11):874-882.

Panzner et al., "Posttranslational protein transport in yeast reconstituted with a purified complex of Sec proteins and Kar2p," May 19, 1995 *Cell* 81(4):561-570.

Park et al., "AEE788, a dual tyrosine kinase receptor inhibitor, inducses endothelial cell apoptosis in human cutaneous squamous cell carcinoma xenografts in nude mice," Mar. 1, 2005 *Clin. Cancer Res.* 11(5):1963-1973.

Parsons et al., "Distinct patterns of tyrosine phosphorylation during the life cycle of *Trypanosoma brucei*," Apr. 1990 *Mol. Biochem. Parasitol.* 45(2):241-248.

Parsons et al., "Protein kinases in divergent eukaryotes: identification of protein kinase activities regulated during trypanosome development," Apr. 1, 1993 *PNAS* 90(7):2656-2660.

Parsons et al., "*Trypanosoma congolense*: developmental regulation of protein kinases and tyrosine phosphorylation during the life cycle," May 1995 *Exp. Parasitol.* 80(3):507-514.

Patham et al., "Post-translational import of protein into the endoplasmic reticulum of a trypanosome: an in vitro system for discovery of anti-trypanosomal chemical entities," Apr. 15, 2009 *Biochem. J.* 419(2):507-517. Available online on Feb. 5, 2009.

Pays and Nolan, "Expression and function of surface proteins in *Trypaosoma brucei*," Mar. 1, 1998 *Mol. Biochem. Parasitol.* 91:3-36.

Pink et al., "Opportunities and challenges in antiparasitic drug discovery," Sep. 2005 *Nat. Rev. Drug Discov.* 4(9):727-740.

Plath et al., "Signal sequence recognition in posttranslational protein transport across the yeast ER membrane," Sep. 18, 1998 *Cell* 94(6):795-807.

Priest and Hajduk, "*Trypanosoma brucei* cytochrome $c_1$ is imported into mitochondria along an unusual pathway," Apr. 25, 2003 *J. Biol. Chem.* 278(17):15084-15094. Available online on Feb. 10, 2003.

"Protein Tyrosine Kinase Inhibitors," product datasheet. CALBIOCHEM® CALBIOCHEM-NOVABIOCHEM Corporation: San Diego, CA; copyright unknown. Available online [retrieved May 13, 2009]. Retrieved from the Internet: <http://www.emdbiosciences.com/SharedImages/TechnicalLiterature/1_CB0611_ptk.pdf>; 4 pgs.

Ramirez et al., "Heterologous expression of a *Trypanosoma cruzi* surface glycoprotein (gp82) in mammalian cells indicates the existence of different signal sequence requirements and processing," Nov.-Dec. 1999 *J. Eukaryot. Microbiol.* 46(6):557-565.

Ranta et al., "Reduced viability of human vascular endothelial cells cultured on Matrigel™," Jul. 1998. *J. Cell. Physiol.* 176(1):92-98.

Rapoport et al., "Protein transport across the eukaryotic endoplasmic reticulum and bacterial inner membranes," 1996 *Ann. Rev. Biochem.* 65:271-303.

Rapoport, "Protein translocation across the eukaryotic endoplasmic reticulum and bacterial plasma membranes," Nov. 29, 2007 *Nature* 450(7170):663-669.

Robinson et al., "The protein tyrosine kinase family of the human genome," Nov. 20, 2000 *Oncogene* 19(49):5548-5557.

Roskoski, "STI-571: an anticancer protein-tyrosine kinase inhibitor," Oct. 3, 2003 *Biochem. Biophys. Res. Comm.* 309(4):709-717.

Rudolph et al., "Determination of copy number of c-Myc protein per cell by quantitative Western blotting," Apr. 10, 1999 *Anal. Biochem* 269(1):66-71.

Rugo et al., "Phase I trial of the oral antiangiogenesis agent AG-013736 in patients with advanced solid tumors: pharmacokinetic and clinical results," Aug. 20, 2005 *J. Clin. Oncol.* 23(24):5474-5483. Available online on Jul. 18, 2005.

Rutkowski et al., "Signal sequences initiate the pathway of maturation in the endoplasmic reticulum lumen," Aug. 8, 2003 *J. Biol. Chem.* 278(32):30365-30372. Available online one May 27, 2003.

Ryan et al., "Intragenic reversion mutations that improve the export of maltose-binding protein in *Escherichia coli* malE signal sequence mutants," Mar. 5, 1986 *J. Biol. Chem.* 261(7):3389-3395.

Ryan and Edwards, "Systematic introduction of proline in a eukaryotic signal sequence suggests asymmetry within the hydrophobic core," Nov. 17, 1995 *J. Biol. Chem.* 270(46):27876-27879.

Saperstein et al., "Design of a selective insulin receptor tyrosine kinase inhibitor and its effect on glucose uptake and metabolism in intact cells," Jun. 27, 1989 *Biochemistry* 28(13):5694-5701. Available online on Jun. 1, 1989.

Sato et al., "A synthetic peptide corresponding to residues 137 to 157 of p60$^{v-src}$ inhibits tyrosine-specific protein kinases," Sep. 28, 1990 *Biochem. Biophys. Res. Comm.* 171(3):1152-1159.

Schatz and Dobberstein, "Common principles of protein translocation across membranes," Mar. 15, 1996 *Science* 271(5255):1519-1526.

Schmidt and Kiser, "SecA: the ubiquitous component of preprotein translocase in prokaryotes," Oct. 1999 *Microbes Infect.* 1(12):993-1004.

Selzer et al., "Cysteine protease inhibitors as chemotherapy: lessons from a parasite target," Sep. 28, 1999 *PNAS* 96(20):11015-11022.

Shawver et al., "Smart drugs: tyrosine kinase inhibitors in cancer therapy," Mar. 2002 *Cancer Cell* 1(2):117-123.

Sheader et al., "Variant surface glycoprotein RNA interference triggers a precytokinesis cell cycle arrest in African trypanosomes," Jun. 14, 2005 *PNAS* 102(24):8716-8721. Available online on Jun. 3, 2005.

Shushan et al., "The AG1478 tyrosine kinase inhibitor is an effective suppressor of leiomyoma cell growth," Sep. 2004 *Hum. Reprod.* 19(9):1957-1967. Available online on Jun. 17, 2004.

Simon et al., "Increased bioavailability of intravenous versus oral CI-1033, a pan erbB tyrosine kinase inhibitor: results of a phase I pharmcokinetic study," Aug. 1, 2006 *Clin. Cancer Res.* 12(15):4645-4651.

Sinyangwe et al., "Trypanocidal drug resistance in eastern province of Zambia," Jan. 30, 2004 *Vet. Parasitol.* 119(2-3):125-135. Available online on Jan. 13, 2004.

Smaill et al., "Tyrosine kinase inhibitors. 18. 6-substituted 4-anilinoquinazolines and 4-anilinopyrido[3,4-*d*]pyrimidines as soluble, irreversible inhibitors of the epidermal growth factor receptor," Feb. 1, 2001 *J. Med. Chem.* 44(3):429-440. Available online on Dec. 30, 2000.

Stanton et al., "Cysteine-less glycosylphosphatidylinositol-specific phospholipase C is inhibited competitively by a thiol reagent: evidence for glyco-mimecry by *p*-chloromercuriphenylsulphonate," 2002 *Biochem. J.* 366(pt. 1):281-288. Available online on May 15, 2002.

Stanton et al., "AUG-proximal nucleotides regulate protein synthesis in *Leishmania tropica*," Aug. 2006 *Mol. Microbiol.* 61(3):691-703. Available online on Jun. 20, 2006.

Steeghs et al., "Small molecule tyrosine kinase inhibitors in the treatment of solid tumors: an update of recent developments," Feb. 2007 *Ann. Surg. Oncol.* 14(2):942-953. Available online on Nov. 14, 2006.

Steff et al., "Detection of a decrease in green fluorescent protein fluorescence for the monitoring of cell death: an assay amenable to high-throughput screening technologies," Dec. 1, 2001 *Cytometry* 45(4):237-243.

Steverding et al., "Transferrin-binding protein complex is the receptor for transferrin uptake in *Trypanosoma brucei*," Dec. 1995 *J. Cell Biol.* 131(5):1173-1182.

Steverding and Scory, "*Trypanosoma brucei*: unexpected azide sensitivity of bloodstream forms," Oct. 2004 *J. Parasitol.* 90(5):1188-1190.

Stewart et al., "Trypanocidal activity of melamine-based nitroheterocycles," May 2004 *Antimicrob. Agents Chemother.* 48(5):1733-1738.

Stone, "FLT3 target practice," Aug. 15, 2004 *Blood* 104(4):915-916.

Strawn et al., "Flk-1 as a target for tumor growth inhibition," Aug. 1, 1996 *Cancer Res.* 56(15):3540-3545.

Subramanya et al., "Regulated cleavage of intracellular glycosylphosphatidylinositol in a trypanosome. Peroxisome-to-endoplasmic reticulum translocation of a phospholipase C," May 2006 *FEBS J.* 273(10):2110-2126.

Subramanya et al., "Glycosylphosphatidylinositol-specific phospholipase C regulates transferrin endocytosis in the African trypanosome," Feb. 1, 2009 *Biochem. J.* 417(3):685-694. Available online on Sep. 11, 2008.

SU5614 product datasheet [online]. CALBIOCHEM: San Diego, CA; last revised on Oct. 5, 2007. Available online [retrieved on May 18, 2009]. Retrieved from the Internet: <http://www.emdbiosciences.com/Products/pds.asp?catno=572632>; 1 pg.

SUTENT® (sunitib malate) product website [online]. Pfizer Oncology: New York, NY; Copyright 2007 [retrieved on May 13, 2009]. Retrieved from the Internet: <http://www.sutent.com/>; 2 pgs.

International Search Report and Written Opinion of the International Searching Authority issued on Jun. 17, 2008, in PCT/US2007/017555; 11 pgs.

International Search Report and Written Opinion of the International Searching Authority issued on Nov. 10, 2008, in PCT/US2007/024319; 9 pgs.

Izard and Kendall, "Signal peptides: exquisitely designed transport promoters," Sep. 1994 *Mol. Microbiol.* 13 (5):765-773.

Johnson and Hunter, "Kinomics: methods for deciphering the kinome," Jan. 2005 *Nat. Methods* 2(1):17-25. Available online on Dec. 21, 2004.

Johnson and van Waes, "The translocon: a dynamic gateway at the ER membrane," 1999 *Ann. Rev. Cell Dev. Biol.* 15:799-842.

Jonassen et al., "Finding flexible patterns in unaligned protein sequences," Aug. 1995 *Protein Sci.* 4(8): 1587-1595.

Jungnickel and Rapoport, "A posttargeting signal sequence recognition event in the endoplasmic reticulum membrane," Jul. 28, 1995 *Cell* 82(2):261-270.

Kaiser et al., "Many random sequences functionally replace the secretion signal sequence f yeast invertase," Jan. 16, 1987 *Science* 235(4786):312-317.

Kantarjian et al., "Nilotinib in imatinib-resistant CML and Philadelphia chromosome-positive ALL," Jun. 15, 2006 *New Engl. J. Med.* 354(24):2542-2551.

Kim et al., "An orally administered multitarget tyrosine kinase inhibitor, SU11248, is a novel potent inhibitor of thyroid oncogenic RET/papillary thyroid cancer kinases," Oct. 2006 *J. Clin. Endocrin. Metab.* 91(10):4070-4076. Available online on Jul. 18, 2006.

Knight and Shokat, "Features of selective kinase inhibitors," Jun. 24, 2005 *Chem. Biol.* 12(6):621-637.

Knott and Robinson, "The secA inhibitor, azide, reversibly blocks the translocation of a subset of proteins across the chloroplast thylakoid membrane," Mar. 18, 1994 *J. Biol. Chem.* 269(11):7843-7846.

Konrad et al., "Glucose-induced tyrosine phosphorylation of p125 in beta cells and pancreatic islets. A novel proximal signal in insulin secretion," Sep. 27, 1996 *J. Biol. Chem.* 271(39):24179-24186.

Kovalenko et al., "Selective platelet-derived growth factor receptor kinase blockers reverse sis-transformation," Dec. 1, 1994 *Cancer Res.* 54:6106-6114.

Kroll and Waltenberger, "The vascular endothelial growth factor receptor KDR activates multiple signal transduction pathways in porcine aortic endothelial cells," Dec. 19, 1997 *J. Biol. Chem.* 272(51):32521-32527.

Kumar et al., "Small molecule approach to studying protein tyrosine phosphatase," Jan. 2005 *Methods* 35(1):9-21.

Kwon et al., "Potent and specific inhibition of p60$^{v-src}$ protein kinase both in vivo and in vitro by radicicol," Dec. 15, 1992 *Cancer Res.* 52(24):6926-6930.

Laforet et al., "Signal peptide subsegments are not always functionally interchangeable. M13 procoat hydrophobic core fails to transport alkaline phosphatase in *Escherichia coli*," Aug. 25, 1989 *J. Biol. Chem.* 264(24):14478-14485.

Letts and Zimmerman, "Polypeptide synthesis with microsomes from pressure-treated *Tetrahymena*," 1970 *J. Protozool.* 17(4):593-596.

Levitzki, "Tyrphostins—potential antiproliferative agents and novel molecular tools," Sep. 1, 1990 *Biochem. Pharmacol.* 40(5):913-918.

Levitzki and Gilon, "Tyrphostins as molecular tools and potential antiproliferative drugs," May 1991 *Trends Pharmacol. Sci.* 12(5):171-174.

Levitzki, "Tyrphostins: tyrosine kinase blockers as novel antiproliferative agents and dissectors of signal transduction," Nov. 1992 *FASEB J.* 6(14):3275-3282.

Levitzki and Gazit, "Tyrosine kinase inhibition: an approach to drug development," Mar. 24, 1995 *Science* 267(5205):1782-1788.

Levitzki and Mishani, "Tyrphostins and other tyrosine kinase inhibitors," 2006 *Ann. Rev. Biochem.* 75:93-109.

Ling et al., "Metabolism and excretion of erlotinib, a small molecule inhibitor of epidermal growth factor receptor tyrosine kinase, in healthy male volunteers," Mar. 2006 *Drug Metab. Dispos.* 34(3):420-426. Available online on Dec. 28, 2005.

Linggi and Carpenter, "ErbB receptors: new insights on mechanisms and biology," Dec. 2006 *Trends Cell Biol.* 16(12):649-656. Available online on Nov. 7, 2006.

Liu et al., "RNA interference of signal peptide-binding protein SRP54 elicits deleterious effects and protein sorting defects in trypanosomes," Dec. 6, 2002 *J. Biol. Chem.* 277(49)47348-47357. Available online on Sep. 19, 2002.

Liu et al., "Synthesis and biological evaluation of substituted 6-alkynyl-4-anilinoquinazoline derivatives as potent EGFR inhibitors," Nov. 15, 2007 *Bioorg. Med. Chem. Lett.* 17(22):6373-6377. Available online on Aug. 28, 2007.

Lustig et al., "Down-regulation of the trypanosomatid signal recognition particle affects the biogenesis of polytopic membrane proteins but not of signal peptide-containing proteins," Oct. 2007 *Eukaryot. Cell* 6(10):1865-1875. Available online on Aug. 22, 2007.

Lyall et al., "Tyrphostins inhibit epidermal growth factor (EGF)-receptor tyrosine kinase activity in living cells and EGF-stimulated cell proliferation," Aug. 25, 1989 *J. Biol. Chem.* 264(24):14503-14509.

Lyman and Scheckman, "Interaction between BiP and Sec63p is required for the completion of protein translocation into the ER of *Saccharomyces cerevisiae*," Dec. 1, 1995 *J. Cell Biol.* 131(5):1163-1171.

Martoglio and Dobberstein, "Snapshots of membrane-translocating proteins," Apr. 1996 *Trends Cell Biol.* 6(4):142-147.

Martoglio and Dobberstein, "Signal sequences: more than just greasy peptides," Oct. 1998 *Trends Cell Biol.* 8(10):410-415.

Matlack et al., "Protein translocation: tunnel vision," Feb. 6, 1998 *Cell* 92(3):381-390.

Matoba and Ogrydziak, "Another factor besides hydrophobicicty can affect signal peptide interaction with signal recognition particle," Jul. 24, 1998 *J. Biol. Chem.* 273(30):18841-18847.

McClellan et al., "Specific molecular chaperone interactions and an ATP-dependent conformational change are required during post-translational protein translocation into the yeast ER," Dec. 1998 *Mol. Biol. Cell* 9(12):3533-3545.

McClellan and Brodsky, "Mutation of the ATP-binding pocket of *SSA1* indicates that a functional interaction between Ssa1p and Ydj1p is required for post-translational translocation into the yeast endoplasmic reticulum," Oct. 2000 *Genetics* 156(2):501-512.

McConville et al., "Secretory pathway of trypanosomatid parasites," Mar. 2002 *Microbiol. Mol. Biol. Rev.* 66(1):122-154.

McKerrow, "Parasitic infections-molecular diagnosis and rational drug design," Sep. 1996 *Biologicals* 24(3):207-208.

Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Jan. 2003 *Clin. Cancer Res.* 9(1):327-337.

Mensa-Wilmot, Kojo; University of Georgia faculty webpage [online] University of Georgia Center for Drug Discovery [retrieved on May 4, 2009]. Retrieved from the Internet: <http://www.uga-cdd.org/facultydetail.php?id=43>; 2 pgs.

Mensa-Wilmot, Kojo; University of Georgia faculty webpage [online] University of Georgia Department of Cellular Biology [retrieved on May 4, 2009]. Retrieved from the Internet: <http://www.uga.edu/cellbio/mensa-wilmot.html>; 4 pgs.

Mesa-Wilmot, Kojo "Endoplasmic Reticulum of Trypanosomatids," Grant Abstract, Grant No. 1RO3AI053086-01 [online]. National Institute of Allergy and Infectious Diseases, National Institutes of Health. Project dates Sep. 30, 2002 to Sep. 29, 2004 [retrieved on May 4, 2009]. Retrieved from the Internet: <http://crisp.cit.nih.gov/crisp/CRISP_LIB.getdoc?textkey=6556407&p_grant_num=1R03AI053086-01&p_query=&ticket=93590487&p_audit_session_id=463086249&p_keywords=>; 2 pgs.

Mesa-Wilmot, Kojo "Endoplasmic Reticulum of Trypanosomatids," Grant Abstract, Grant No. 5RO3AI053086-02 [online]. National Institute of Allergy and Infectious Diseases, National Institutes of Health. Project dates Sep. 30, 2002 to Sep. 29, 2004 [retrieved on May 4, 2009]. Retrieved from the Internet: <http://crisp.cit.nih.gov/crisp/CRISP_LIB.getdoc?textkey=6660348&p_grant_num=5R03AI053086-02&p_query=&ticket=93590487&p_audit_session_id=463086249&p_keywords=>; 2 pgs.

Merkel et al., "Inhibition of EGF-induced vasoconstriction in isolated rabbit aortic rings with the tyrosine kinase inhibitor RG50864," May 14, 1993 *Biochem. Biophys. Res. Comm.* 192(3):1319-1326.

Miller et al., "SecB modulates the nucleotide-bound state of SecA and stimulates ATPase activity," Apr. 23, 2002 *Biochem.* 41(16):5325-5332. Available online on Mar. 29, 2002.

Mitra et al., "Co- and post-translational translocation through the protein-condi=ucting channel: analogous mechanisms at work?" Nov. 2006 *Nat. Struct. Mol. Biol.* 13(11):957-964. Available online on Nov. 3, 2006.

Mohammadi et al., "Structure of the tyrosine kinase domain of fibroblast growth factor receptor in complex with inhibitors," May 9, 1997 *Science* 276(5314):955-960.

Mustafa et al., "Tyrosine kinases are required for interferon-γ-stimulated proliferation of *Trypanosoma brucei brucei*," Mar. 1997 *J. Infect. Dis.* 175(3):669-673.

Naula et al., "Protein kinases as drug targets in trypanosomes and *Leishmania*," Dec. 30, 2005 *Biochim. Biophys. Acta* 1754(1-2):151-159. Available online on Sep. 8, 2005.

NEXAVAR® (sorafenib) product website [online] Onyx Pharmaceuticals, Inc.: Emeryville, CA; and Bayer HealthCare Pharmaceuticals, Inc.: Leverkusen, Germany. Copyright 2008 [retrieved on May 13, 2009]. Retrieved from the Internet: <http://www.nexavar-us.com/scripts/pages/en/home/index.php>; 2 pgs.

"Nexavar significantly extends overall survival by 44% in liver cancer patients," Jun. 4, 2007 Onyx Pharmaceuticals, Inc. press release. Available online [retrieved on Nov. 16, 2007]. Retrieved from the Internet: <http://www.onyx-pharm.com/wt/page/pr_1180935729>; 3 pgs.

Ng et al., "Signal sequences specify the targeting route to the endoplasmic reticulum membrane," Jul. 1, 1996 *J. Cell Biol.* 134(2):269-278.

Ngosuwan et al., "Roles of cytosolic Hsp70 and Hsp40 molecular chaperones in post-translational translocation of presecretory proteins into the endoplasmic reticulum," Feb. 28, 2003 *J. Biol. Chem.* 278(9):7034-7042. Available online on Dec. 19, 2002.

Nielsen et al., "Identification of prokaryotic and eukaryotic signal peptides and prediction of their cleavage sites," Jan. 1997 *Protein Eng.* 10(1):1-6.

Novogrodsky et al., "Prevention of lipopolysaccharide-induced lethal toxicity by tyrosine kinase inhibitors," May 27, 1994 *Science* 264(5163):1319-1322.

Nwaka and Ridley, "Virtual drug discovery and development for neglected diseases through public-private partnerships," Nov. 2003 *Nat. Rev. Drug Discov.* 2(11):919-928.

\* cited by examiner

Figure 2
A
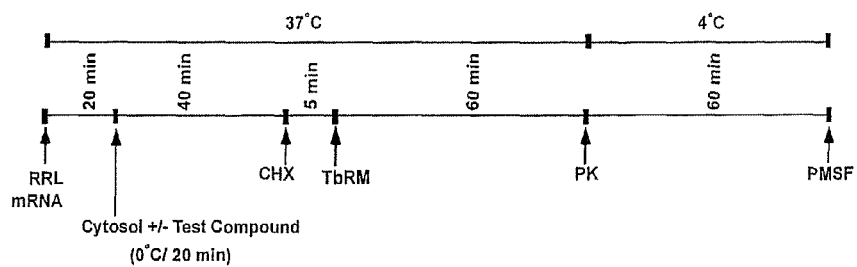
B
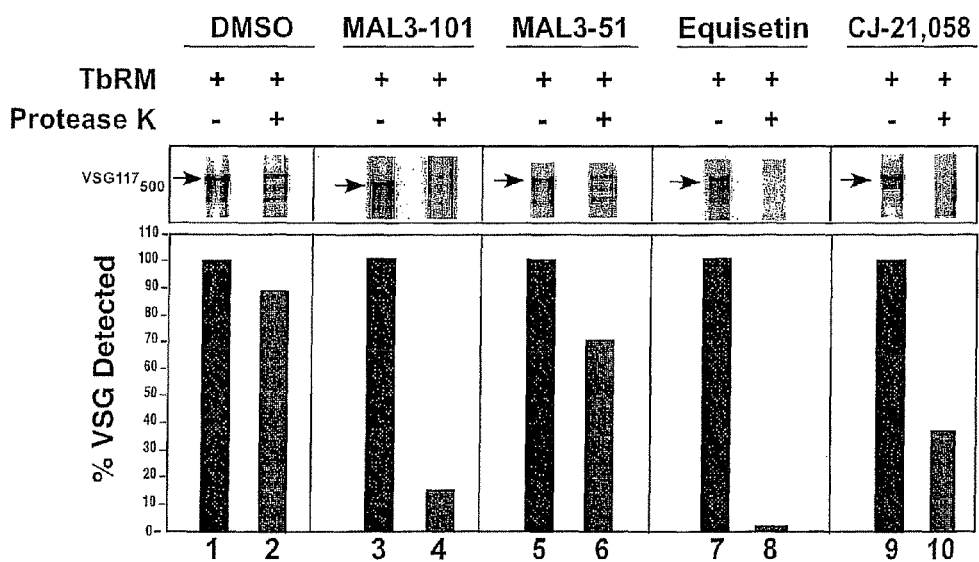

Figure 3
A
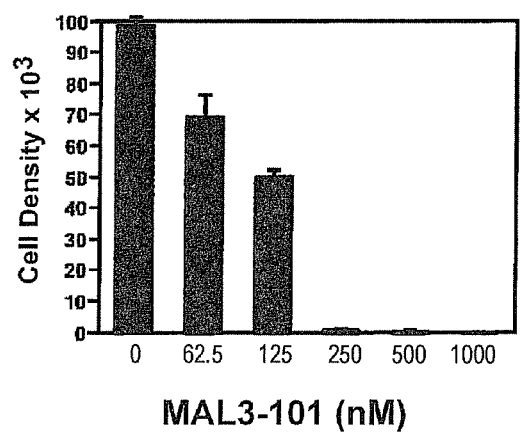
B
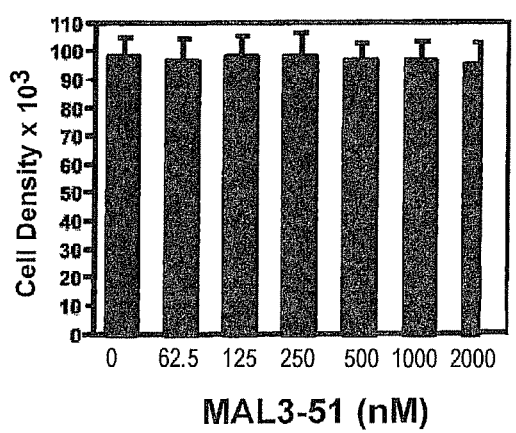
C
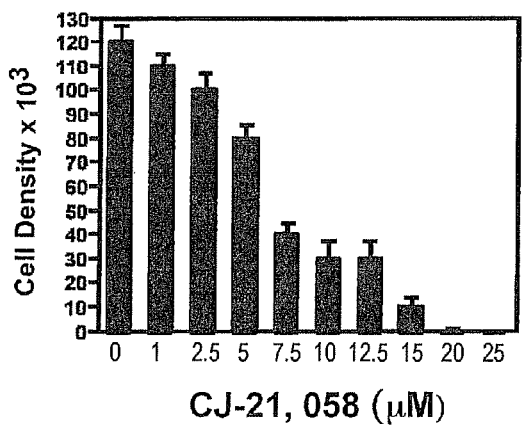
D
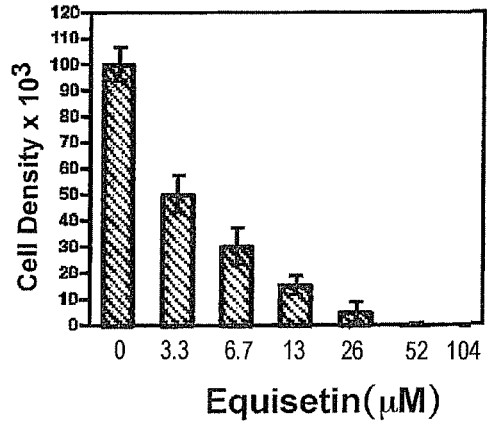

Figure 4
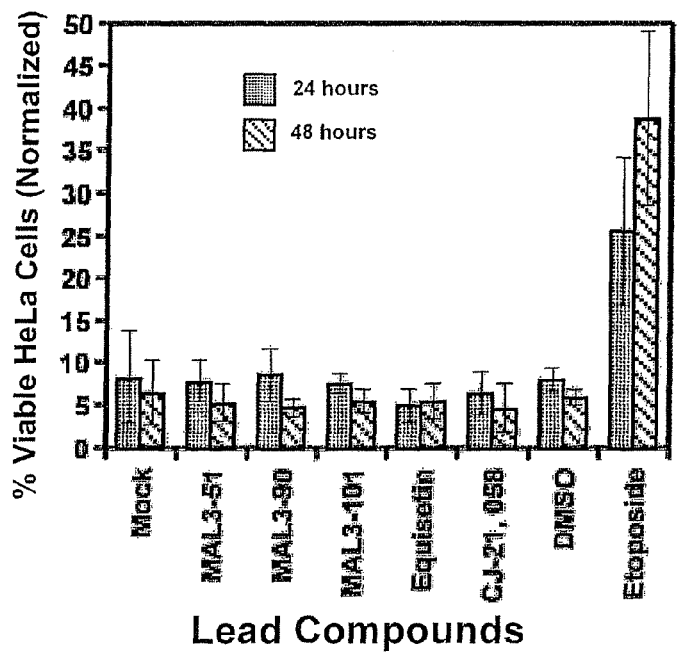
A
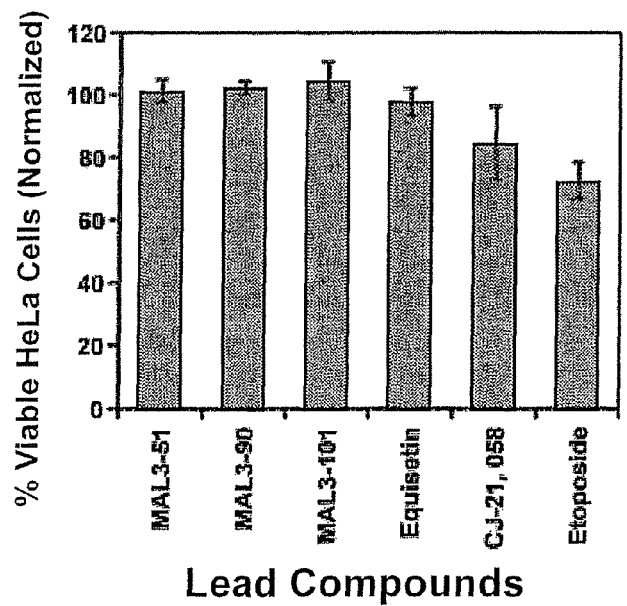
B

C.
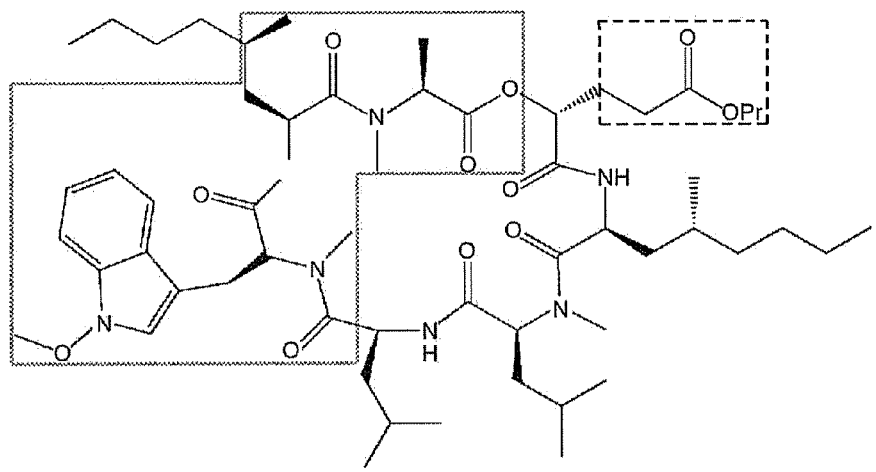
CAM741
D.
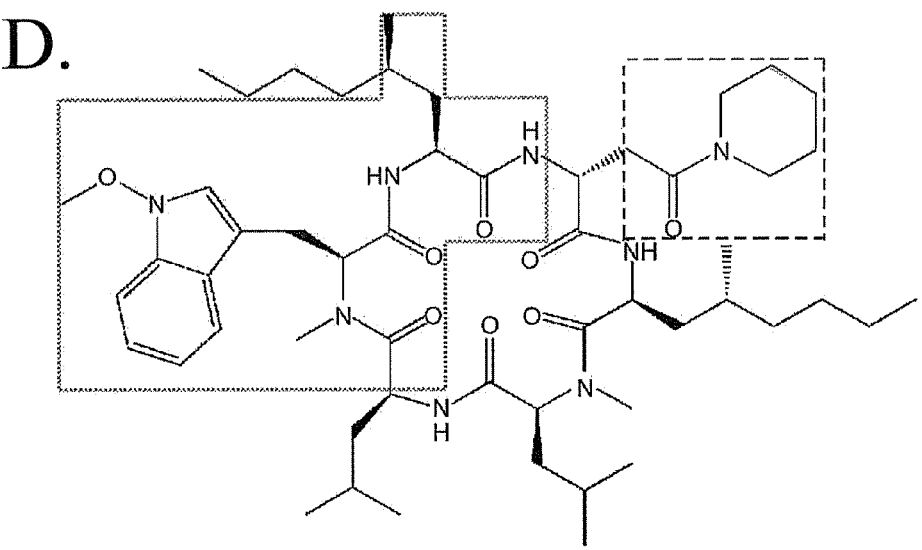
NFI028
Fig. 6

Figure 7
A
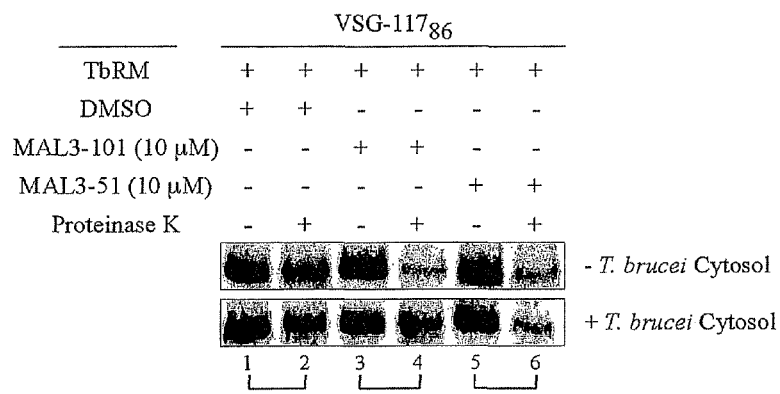
B
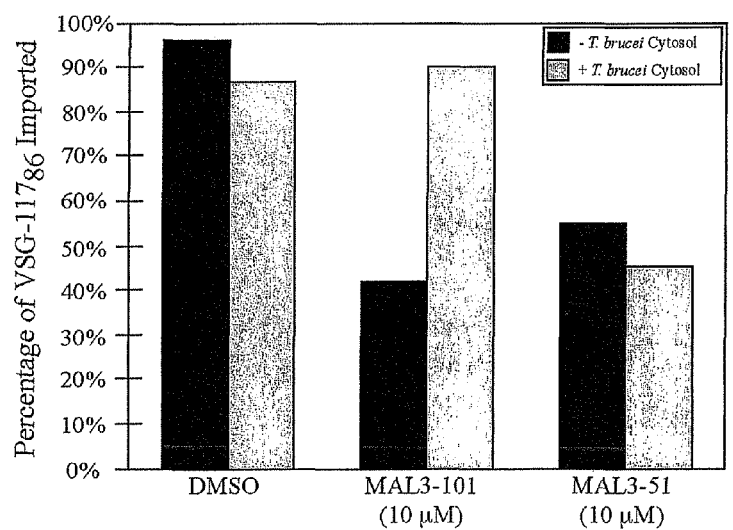

Figure 8
A
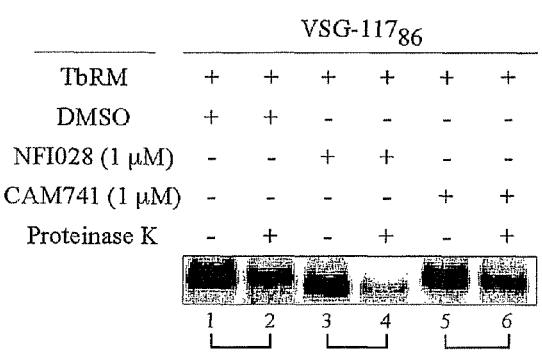
B
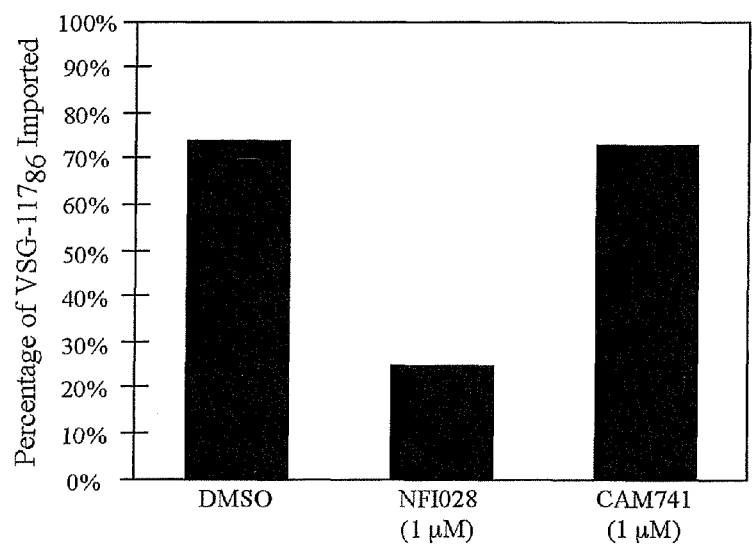

Figure 8
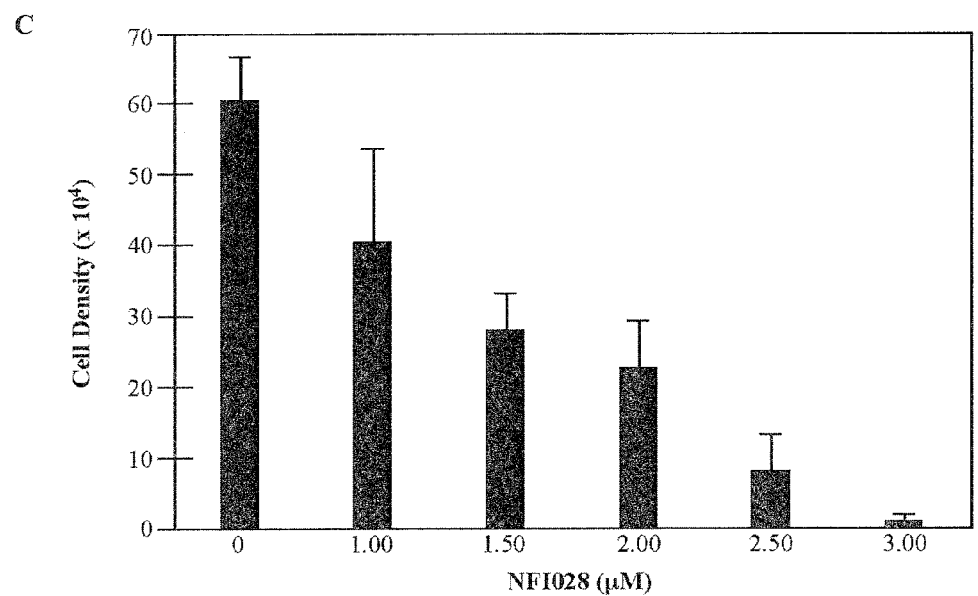
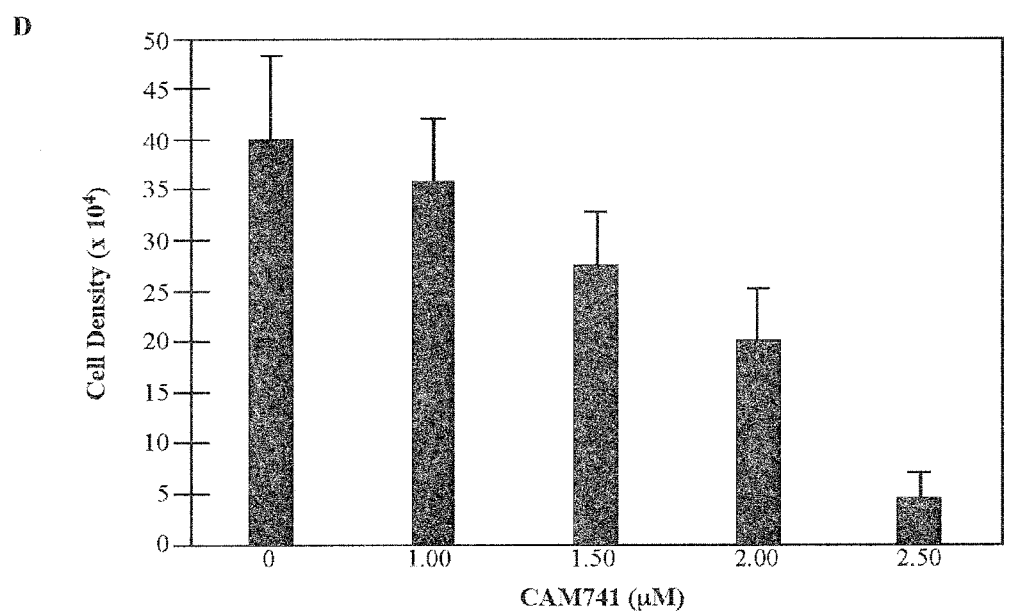

Figure 9
A
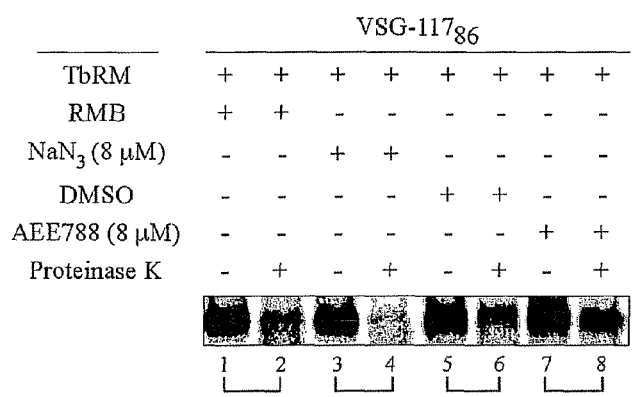
B
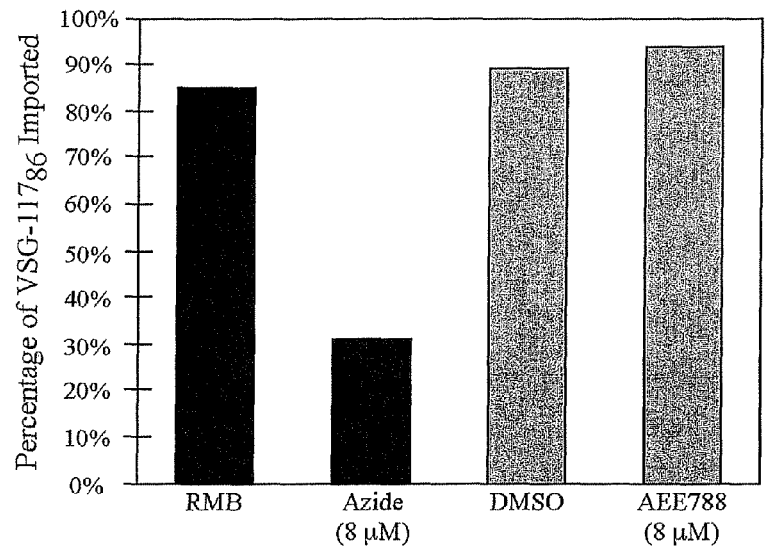

| | VSG-117₈₆ | | | | | | | | | | | |
|---|---|---|---|---|---|---|---|---|---|---|---|---|
| TbRM treated with RMB | + | + | − | − | − | − | − | − | − | − | − | − |
| TbRM treated with NaN₃ (8 µM) | − | − | + | + | − | − | − | − | − | − | − | − |
| TbRM treated with DMSO | − | − | − | − | + | + | − | − | − | − | − | − |
| TbRM treated with NFI028 (1 µM) | − | − | − | − | − | − | + | + | − | − | − | − |
| TbRM treated with Valinomycin (0.5 µM) | − | − | − | − | − | − | − | − | + | + | − | − |
| TbRM treated with EtOH | − | − | − | − | − | − | − | − | − | − | + | + |
| Proteinase K | − | + | − | + | − | + | − | + | − | + | − | + |
| | 1 | 2 | 3 | 4 | 5 | 6 | 7 | 8 | 9 | 10 | 11 | 12 |

D

Bar chart showing Percentage of VSG-117₈₆ Imported:
- RMB: ~91%
- NaN₃ (8 µM): ~94%
- DMSO: ~88%
- NFI028 (1 µM): ~78%
- Valinomycin (0.5 µM): ~77%
- EtOH: ~79%

|  | TbRM | − | − | + | + |
|---|---|---|---|---|---|
|  | Proteinase K | − | + | − | + |
| A | VSG-117$_{86}$ | | | | |
| B | (Gly)$_4$-VSG-117$_{86}$ | | | | |
| C | (Ser)$_4$-VSG-117$_{86}$ | | | | |
| D | (Ala)$_7$-VSG-117$_{86}$ | | | | |
| E | (Ala)$_6$-Ile12-VSG-117$_{86}$ | | | | |
| F | (Ala)$_4$-VSG-117$_{86}$ | | | | |

Lanes: 1  2   3  4

B

Bar chart — Kyte-Doolittle Hydrophobicity Units (left axis) and Percentage of VSG Imported (right axis) for: VSG-117$_h$, (Gly)$_4$-VSG-117$_h$, (Ser)$_4$-VSG-117$_h$, (Ala)$_7$-VSG-117$_h$, (Ala)$_6$-Ile12-VSG-117$_h$, (Ala)$_4$-VSG-117$_h$.

Legend: Peak Hydrophobicity; Percent VSG Import

Figure 12

| TbRM | − | − | + | + |
|---|---|---|---|---|
| Proteinase K | − | + | − | + |

A

A  VSG-117$_{86}$
B  (Ala)$_4$-VSG-117$_{86}$
C  Scrambled (Ala)$_4$-VSG-117$_{86}$
D  (Ser)$_4$-VSG-117$_{86}$
E  Scrambled (Ser)$_4$-VSG-117$_{86}$
F  (Ala)$_4$-Tyr9-VSG-117$_{86}$ 1  2  3  4

B

Bar chart: Kyte-Doolittle Hydrophobicity Units (left axis, 0–2.5) and Percentage of VSG Imported (right axis, 0%–100%) for: VSG-117$_h$, (Ala)$_4$-VSG-117$_h$, Scrambled (Ala)$_4$-VSG-117$_h$, (Ser)$_4$-VSG-117$_h$, Scrambled (Ser)$_4$-VSG-117$_h$, (Ala)$_4$-Tyr9-VSG-117$_h$.

Legend: ■ Peak Hydrophobicity; ▨ Percent VSG Import

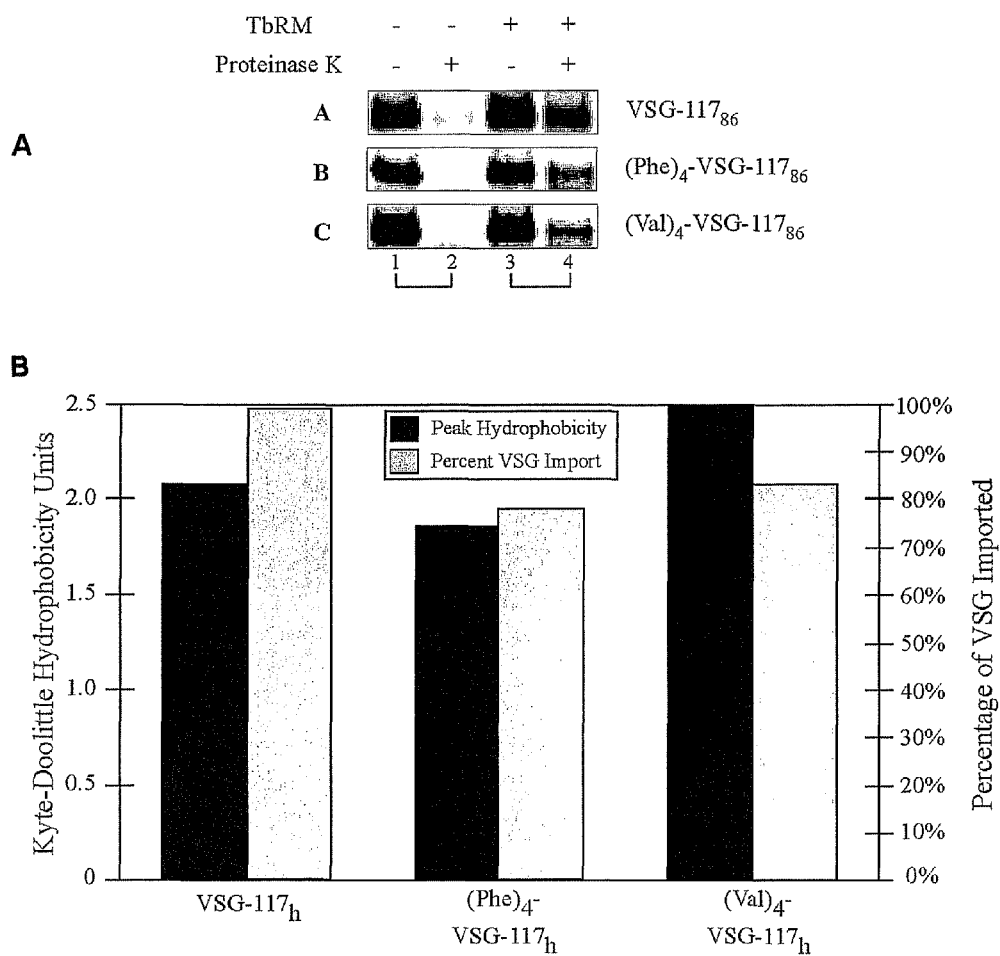

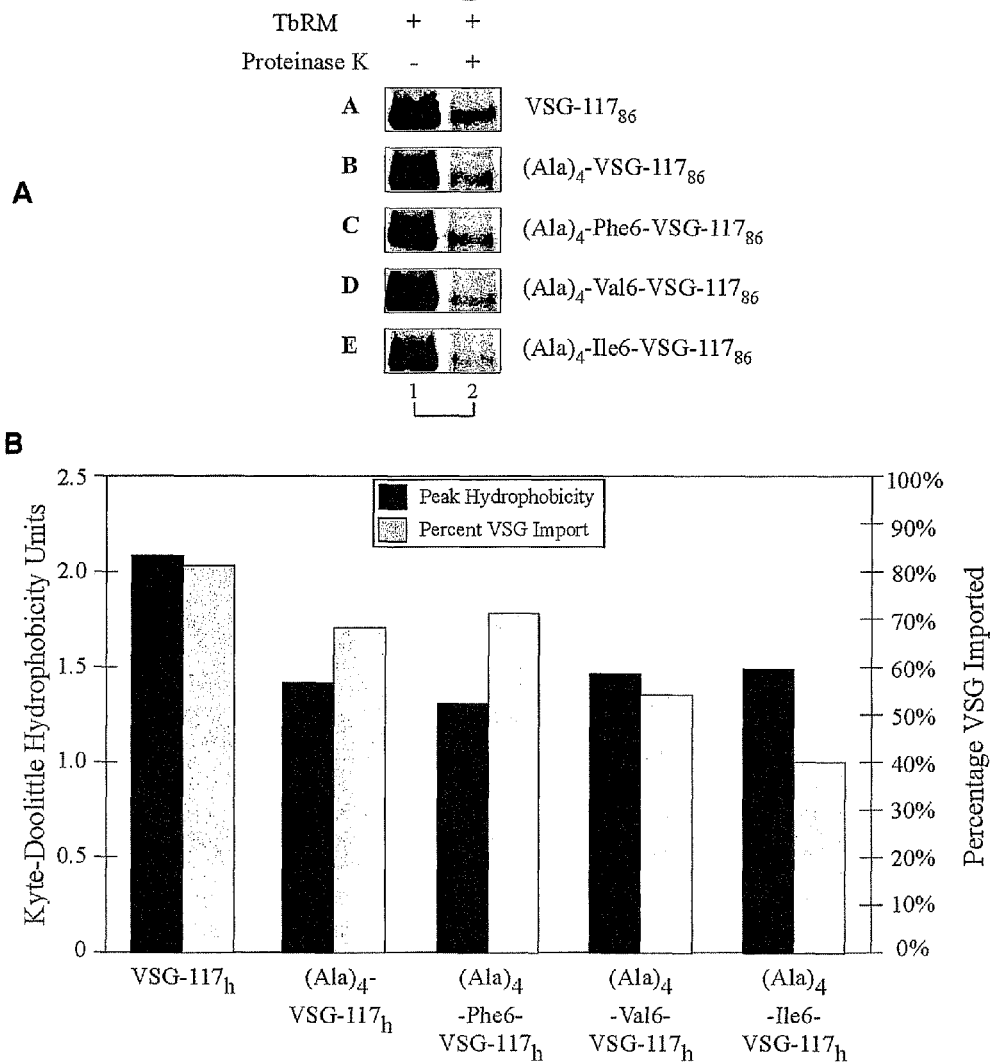

Fig. 15

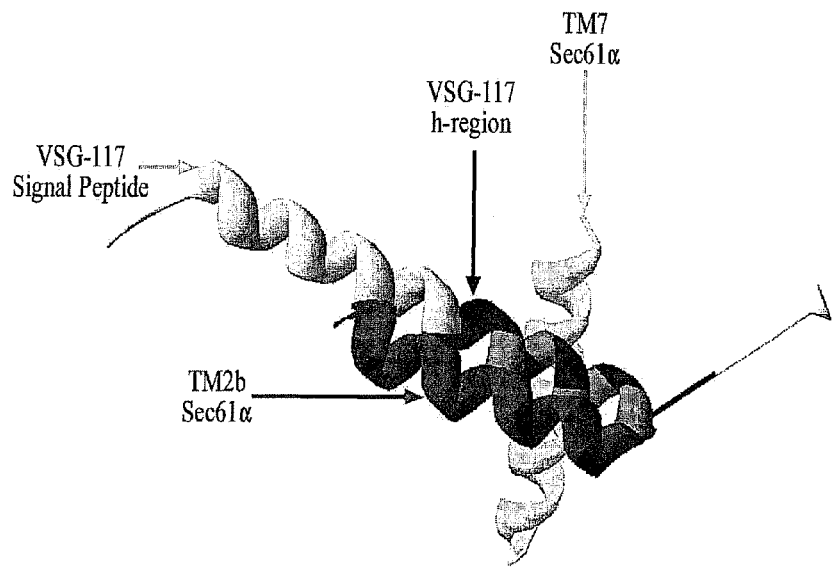
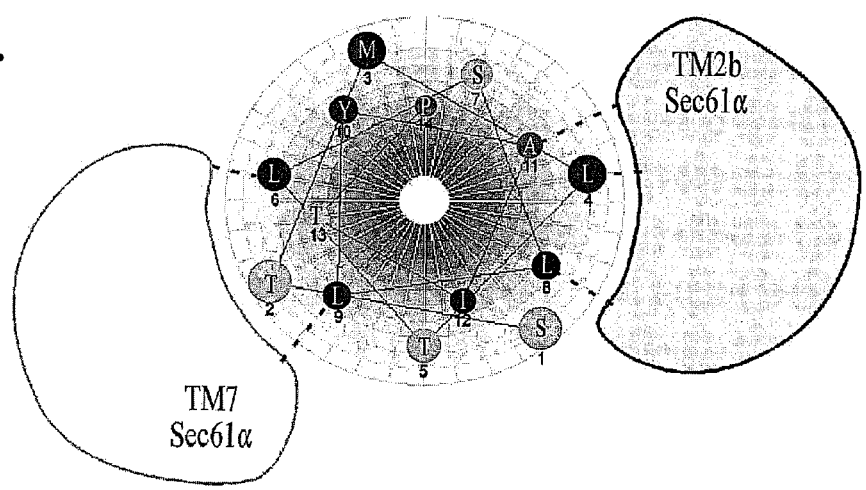
Fig. 16

Figure 17
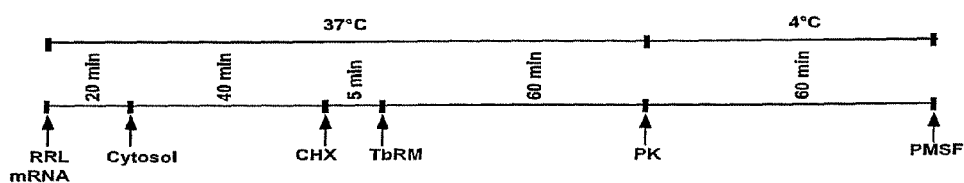
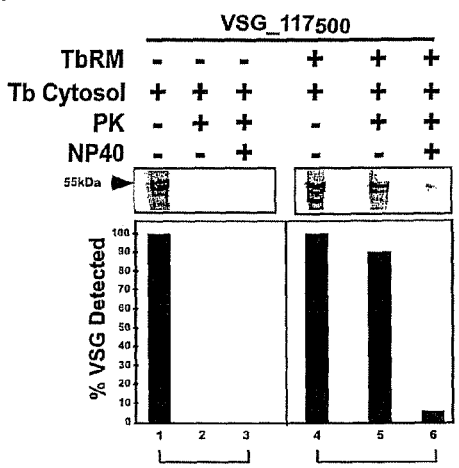
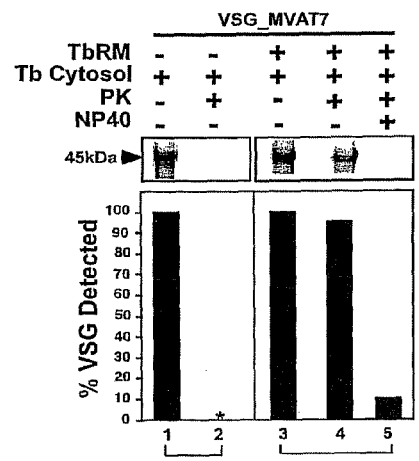
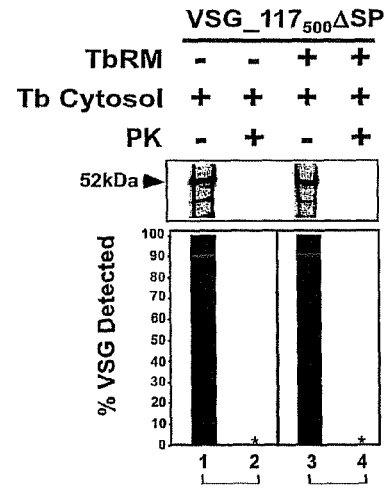

Figure 18
A
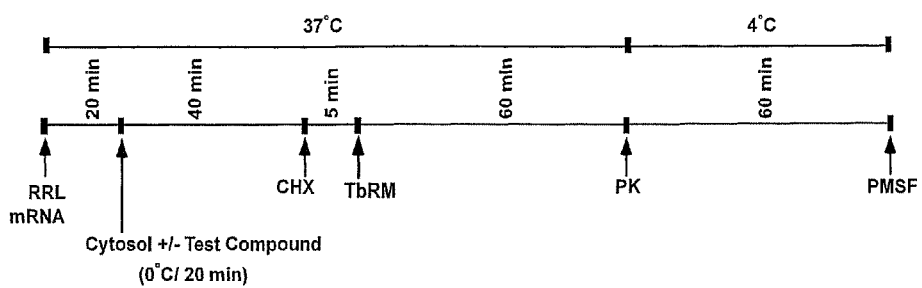
B
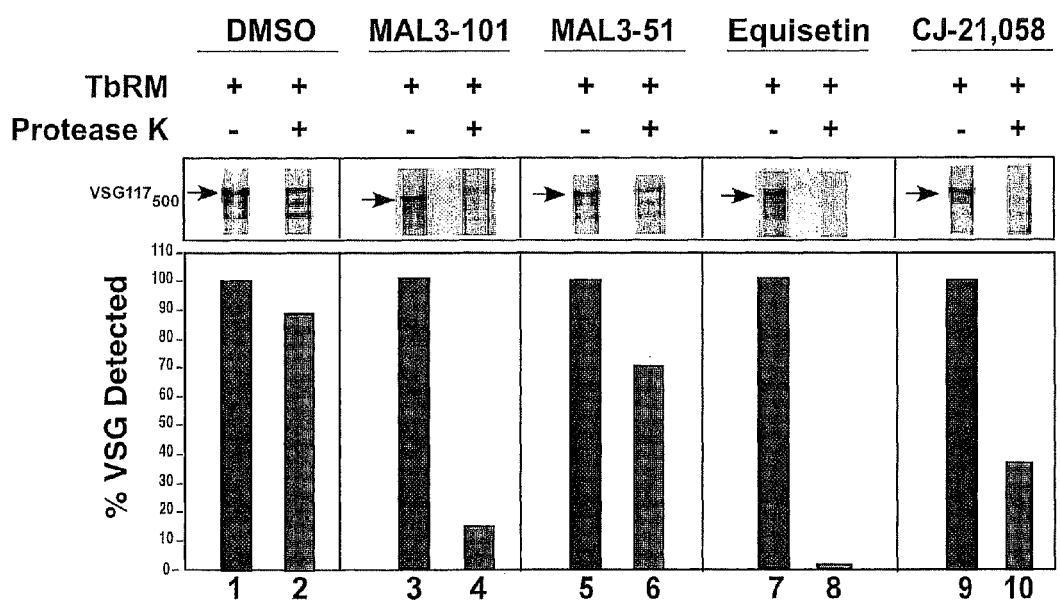

Figure 19
A
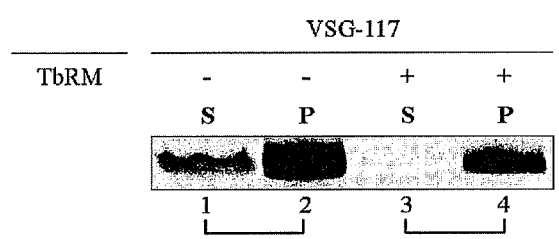
B
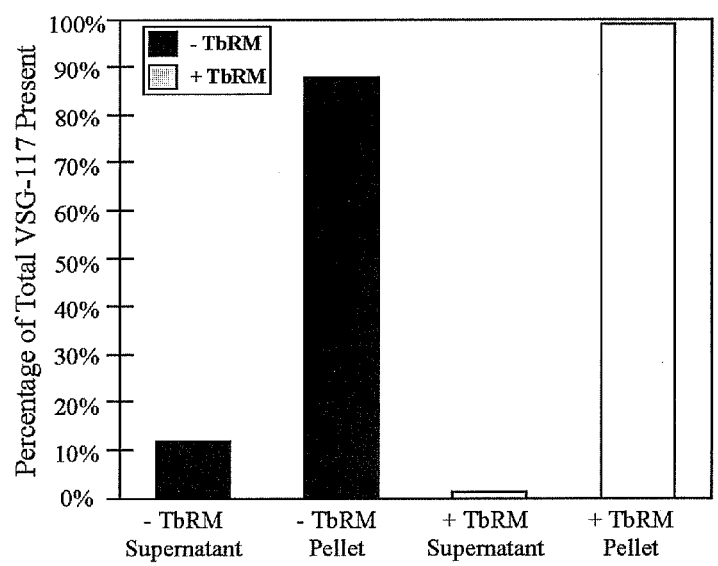

Figure 19
C
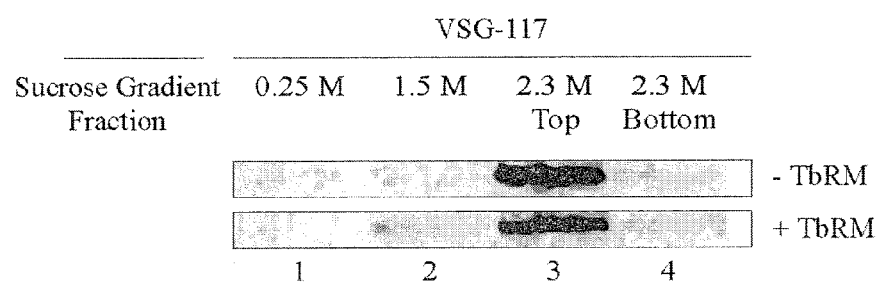
D
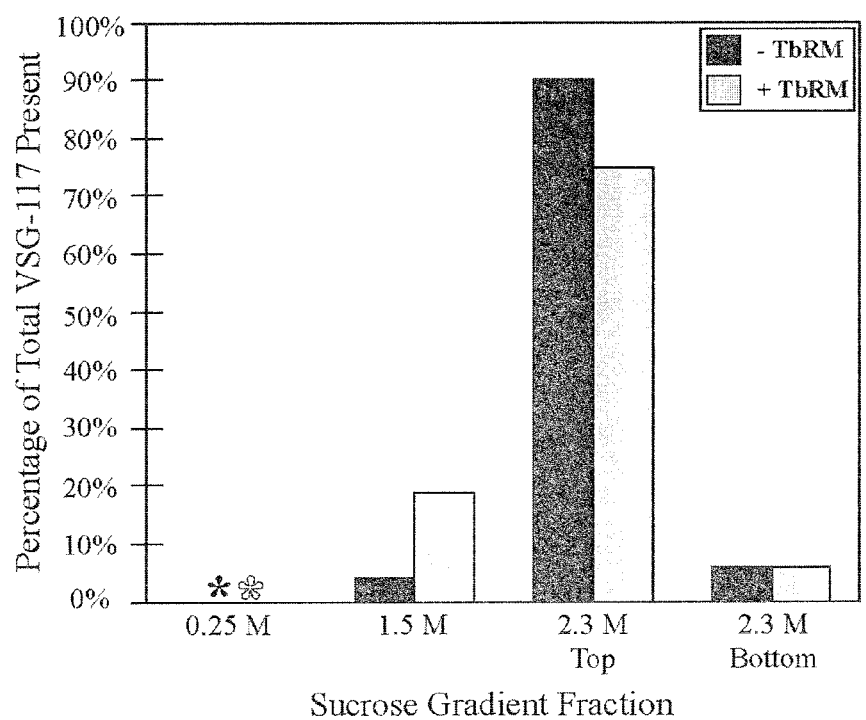

ial Application Ser. No. 61/094,457, filed Sep. 5, 2008; all of which are incorporated herein by reference in their entireties.

SEQUENCE LISTING

<160> NUMBER OF SEQ ID NOS: 26

<210> SEQ ID NO 1
<211> LENGTH: 59
<212> TYPE: DNA
<213> ORGANISM: artificial
<220> FEATURE:
<223> OTHER INFORMATION: synthetic oligonucleotide primer

<400> SEQUENCE: 1

```
ccctaatacg actcactata gggaggaggg tttttaccat ggactgccat acaaaggag    59
```

<210> SEQ ID NO 2
<211> LENGTH: 48
<212> TYPE: DNA
<213> ORGANISM: artificial
<220> FEATURE:
<223> OTHER INFORMATION: synthetic oligonucleotide primer

<400> SEQUENCE: 2

```
cgaacaacga agggggttctt atagtgcgta gattcgtagc ttcgtttc    48
```

<210> SEQ ID NO 3
<211> LENGTH: 127
<212> TYPE: DNA
<213> ORGANISM: artificial
<220> FEATURE:
<223> OTHER INFORMATION: synthetic oligonucleotide primer

<400> SEQUENCE: 3

```
taatacgact cactataggg aggagggttt ttaccatgga ctgccataca aaggagacac    60
tggggtcaca caatggaggc gatcaacgat gttcacacta tcattcttct acttcatcac   120
tccagcg                                                            127
```

<210> SEQ ID NO 4
<211> LENGTH: 47
<212> TYPE: DNA
<213> ORGANISM: artificial
<220> FEATURE:
<223> OTHER INFORMATION: synthetic oligonucleotide primer

<400> SEQUENCE: 4

```
cgaacaacga agggggttctt atagtgcgta gatcgtagct tcgtttc    47
```

<210> SEQ ID NO 5
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 5

Ser Thr Met Leu Thr Leu Ser Leu Leu Tyr Ala Ile Thr Pro
1               5                   10

<210> SEQ ID NO 6
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 6

Ser Thr Met Gly Thr Leu Ser Gly Gly Tyr Gly Ile Thr Pro
1               5                   10

<210> SEQ ID NO 7
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 7

Ser Thr Met Ser Thr Leu Ser Ser Ser Tyr Ser Ile Thr Pro
1               5                   10

```
<210> SEQ ID NO 8
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 8

Ser Thr Ala Ala Thr Ala Ser Ala Ala Tyr Ala Ala Thr Pro
1               5                   10

<210> SEQ ID NO 9
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 9

Ser Thr Ala Ala Thr Ala Ser Ala Ala Tyr Ala Ile Thr Pro
1               5                   10

<210> SEQ ID NO 10
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 10

Ser Thr Met Ala Thr Leu Ser Ala Ala Tyr Ala Ile Thr Pro
1               5                   10

<210> SEQ ID NO 11
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 11

Ala Ser Leu Thr Ala Met Ala Thr Ser Ala Tyr Ile Thr Pro
1               5                   10

<210> SEQ ID NO 12
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 12

Ser Ser Leu Thr Ser Met Ser Thr Ser Ser Tyr Ile Thr Pro
1               5                   10

<210> SEQ ID NO 13
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 13

Ser Thr Met Ala Thr Leu Ser Ala Tyr Ala Ala Ile Thr Pro
1               5                   10
```

```
<210> SEQ ID NO 14
<211> LENGTH: 4
<212> TYPE: PRT
<213> ORGANISM: artificial
<220> FEATURE:
<223> OTHER INFORMATION: amino acid sequence of h-motif
<220> FEATURE:
<221> NAME/KEY: misc_feature
<222> LOCATION: (3)..(3)
<223> OTHER INFORMATION: Xaa can be any amino acid

<400> SEQUENCE: 14

Leu Leu Xaa Ala
1

<210> SEQ ID NO 15
<211> LENGTH: 4
<212> TYPE: PRT
<213> ORGANISM: artificial
<220> FEATURE:
<223> OTHER INFORMATION: amino acid sequence of h-motif
<220> FEATURE:
<221> NAME/KEY: misc_feature
<222> LOCATION: (2)..(2)
<223> OTHER INFORMATION: Xaa can be any amino acid

<400> SEQUENCE: 15

Leu Xaa Leu Leu
1

<210> SEQ ID NO 16
<211> LENGTH: 6
<212> TYPE: PRT
<213> ORGANISM: artificial
<220> FEATURE:
<223> OTHER INFORMATION: amino acid sequence of h-motif
<220> FEATURE:
<221> NAME/KEY: misc_feature
<222> LOCATION: (2)..(4)
<223> OTHER INFORMATION: Xaa can be any amino acid

<400> SEQUENCE: 16

Leu Xaa Xaa Xaa Leu Leu
1               5

<210> SEQ ID NO 17
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 17

Ser Thr Met Phe Thr Leu Ser Phe Phe Tyr Phe Ile Thr Pro
1               5                   10

<210> SEQ ID NO 18
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 18

Ser Thr Met Val Thr Leu Ser Val Val Tyr Val Ile Thr Pro
1               5                   10

<210> SEQ ID NO 19
<211> LENGTH: 14
<212> TYPE: PRT
```

```
<213> ORGANISM: artificial
<220> FEATURE:
<223> OTHER INFORMATION: amino acid sequence of VSG-117(h) construct

<400> SEQUENCE: 19

Ser Thr Met Ala Thr Phe Ser Ala Ala Tyr Ala Ile Thr Pro
1               5                   10

<210> SEQ ID NO 20
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 20

Ser Thr Met Ala Thr Val Ser Ala Ala Tyr Ala Ile Thr Pro
1               5                   10

<210> SEQ ID NO 21
<211> LENGTH: 14
<212> TYPE: PRT
<213> ORGANISM: artificial
<220> FEATURE:
<223> OTHER INFORMATION: amino acid sequence of VSG-117(h) construct

<400> SEQUENCE: 21

Ser Thr Met Ala Thr Ile Ser Ala Ala Tyr Ala Ile Thr Pro
1               5                   10

<210> SEQ ID NO 22
<211> LENGTH: 56
<212> TYPE: DNA
<213> ORGANISM: artificial
<220> FEATURE:
<223> OTHER INFORMATION: synthetic oligonucleotide primer

<400> SEQUENCE: 22
taatacgact cactataggg aggagggttt ttaccatgga ctgccataca aaggag        56

<210> SEQ ID NO 23
<211> LENGTH: 47
<212> TYPE: DNA
<213> ORGANISM: artificial
<220> FEATURE:
<223> OTHER INFORMATION: synthetic oligonucleotide primer

<400> SEQUENCE: 23
cgaacaacga agggttctt atagtgcgta gatcgtagct tcgtttc                   47

<210> SEQ ID NO 24
<211> LENGTH: 61
<212> TYPE: DNA
<213> ORGANISM: artificial
<220> FEATURE:
<223> OTHER INFORMATION: synthetic olignucleotide primer

<400> SEQUENCE: 24
ccctaatacg actcactata gggaggaggg tttttaccat ggccacactg agaaaggttg    60
c                                                                    61

<210> SEQ ID NO 25
<211> LENGTH: 27
<212> TYPE: DNA
<213> ORGANISM: artificial
<220> FEATURE:
<223> OTHER INFORMATION: synthetic oligonucleotide primer
```

```
<400> SEQUENCE: 25
catcatcatt tcctaaaaaa gcaaggc                                              27

<210> SEQ ID NO 26
<211> LENGTH: 59
<212> TYPE: DNA
<213> ORGANISM: artificial
<220> FEATURE:
<223> OTHER INFORMATION: synthetic oligonucleotide primer

<400> SEQUENCE: 26
ccctaatacg actcactata gggaggaggg tttttaccat gtcaacaaga gtccaacaa           59
```

TRYPANOSOME MICROSOME SYSTEM AND USES THEREOF

CONTINUING APPLICATION DATA

This application is a continuation-in-part of International Application No. PCT/US2007/017555, filed Aug. 7, 2007, which claims the benefit of U.S. Provisional Application Ser. No. 60/836,045, filed Aug. 7, 2006; further this application claims the benefit of U.S. Provisional Application Ser. No. 61/094,457, filed Sep. 5, 2008; all of which are incorporated herein by reference in their entireties.

GOVERNMENT FUNDING

The present invention was made with government support under Grant No. AI053086, awarded by the National Institutes of Health. The Government has certain rights in this invention.

BACKGROUND

Human African trypanosomiasis (HAT) occurs in 36 countries in Sub-Saharan Africa, threatening an estimated 60 million people with debilitating disease. No vaccines are available for prevention of infection by *Trypanosoma brucei*, which causes trypanosomiasis. Without chemotherapeutic treatment, *T. brucei* kills infected humans. Currently, there are only four drugs approved for the treatment of HAT. All are quite toxic and cause serious side effects and in some cases death (reviewed by Fairlamb, 2003, *Trends Parasitol;* 19(11): 488-94; and Barrett et al., 2007, *Br J Pharmacol;* 152(8): 1155-71). And drug resistance is of concern (for review, see Docampo and Moreno, 2003, *Parasitol Res;* 90 Supp 1:S10-3). Consequently, there is a strong need for better chemotherapeutic options for the treatment of trypanosomiasis. In addition, additional new drugs must be developed, in order to prepare for possible emergence of drug resistance in the parasites (de Koning, 2001, *Int J Parasitol;* 31(5-6):512-22; Ouellette, 2001, *Trop Med Int Health;* 6(11):874-82; and Sinyangwe et al., 2004, *Vet Parasitol;* 119(2-3):12-35).

Unique to *T. brucei* is the expression of a variable surface glycoprotein (VSG) coat on the cell surface, which undergoes constant variation in order to evade the humoral immune system and host antibodies. It is thought that recombination from a repertoire of greater that 1,000 VSG genes is responsible for the vast diversity of the parasite, and its effectiveness in immune evasion. This "antigenic variation" allows *T. brucei* to survive in the host blood stream by evading immune response. VSGs arrive at the plasma membrane after entering the secretory pathway at the endoplasmic reticulum (ER) (McConville et al., 2002, *Microbiol Mol Biol Rev;* 66(1):122-54). The transferrin receptor and nucleobase/nucleoside transporters are other proteins that localize to the plasma membrane after signal peptide dependent import into the ER. Thus, movement of proteins into the ER is crucial for targeting of cell surface receptors and nutrient transporters, as well as for the biogenesis of the Golgi complex, lysosomes, endosomes and the inner nuclear membrane. From the perspective of eukaryotic pathogen control, small molecules that selectively interfere with translocation of proteins into the ER hold promise for treatment of disease because they could block delivery of many proteins to the plasma membrane and as a result compromise viability of parasites. There is a need for efficient, cost-effective assays for identifying drug targets that interfere with protein translocation in trypanosomes.

SUMMARY OF THE INVENTION

The present invention includes a cell free preparation of protozoan microsomes, wherein the cell free preparation of protozoan microsomes translocate a polypeptide into the microsome. In some embodiments, the cell free preparation of protozoan microsomes is the resuspended pellet of a low sped spin of about 5,000 g to about 20,000 g of a protozoan lysate. In some embodiments, the translocated polypeptide is a secreted polypeptide or a plasma membrane polypeptide. In some embodiments the translocated polypeptide is protected from exogenous detergent.

The present invention includes a method of preparing a cell free preparation of protozoan microsomes wherein the cell free preparation of protozoan microsomes translocate a polypeptide into the microsome. In some embodiments, the cell free preparation of protozoan microsomes is the resuspended pellet of a low sped spin of about 5,000 g to about 20,000 g of a protozoan lysate.

The present invention includes a method of endoplasmic reticulum (ER) translocation of a polypeptide using a cell free preparation of protozoan microsomes. In some embodiments, the cell free preparation of protozoan microsomes is the resuspended pellet of a low sped spin of about 5,000 g to about 20,000 g of a protozoan lysate.

The present invention includes a method of screening for an agent that modulates the ER translocation of a polypeptide in a protozoan, the method including contacting a cell free preparation of protozoan microsomes with an agent, and monitoring ER translocation of a polypeptide. In some embodiments, the cell free preparation of protozoan microsomes is the resuspended pellet of a low sped spin of about 5,000 g to about 20,000 g of a protozoan lysate.

The present invention includes a method of screening for an agent for the treatment and/or prevention of a protozoan infection, the method including contacting a cell free preparation of protozoan microsomes with an agent, and monitoring ER translocation of a polypeptide, wherein a modulation in the ER translocation of the polypeptide indicates the agent is a candidate for the treatment of a protozoan infection. In some embodiments, the cell free preparation of protozoan microsomes is the resuspended pellet of a low sped spin of about 5,000 g to about 20,000 g of a protozoan lysate.

The present invention includes a method of screening for an agent that kills, inhibits the growth, and/or inhibits the reproduction of a protozoan, the method including contacting a cell free preparation of protozoan microsomes with an agent, and monitoring ER translocation of a polypeptide, wherein a modulation in the ER translocation of the polypeptide indicates the agent is a candidate agent that kills, inhibits the growth, and/or inhibits the reproduction of a protozoan. In some embodiments, the cell free preparation of protozoan microsomes is the resuspended pellet of a low sped spin of about 5,000 g to about 20,000 g of a protozoan lysate.

The present invention includes a method of treating a protozoan infection in a subject, the method including administering to the subject an effective amount of an agent that modulates the ER translocation of a polypeptide in a cell free preparation of protozoan microsomes. In some embodiments, the cell free preparation of protozoan microsomes is the resuspended pellet of a low sped spin of about 5,000 g to about 20,000 g of a protozoan lysate.

The present invention includes a method of killing, inhibiting the growth and/or inhibiting the reproduction of a protozoan, the method including contacting the protozoan with an agent that modulates the ER translocation of a polypeptide in a cell free preparation of protozoan microsomes. In some embodiments, the cell free preparation of protozoan microsomes is the resuspended pellet of a low sped spin of about 5,000 g to about 20,000 g of a protozoan lysate.

In some embodiments of the methods of the present invention, modulation is a decrease or inhibition in the ER translocation of the polypeptide.

The present invention includes a cell free preparation of protozoan cytosol, wherein the preparation of protozoan cytosol is the supernatant of a high speed spin of greater than 20,000 g of a protozoan lysate, wherein the protozoan cytosol preparation demonstrates the ability to facilitate the translocation of a plasma membrane polypeptide into a cell free preparation of protozoan microsomes. In some embodiments, a high speed spin is greater than 20,000 g. In some embodiments, the cell free preparation of protozoan microsomes is the resuspended pellet of a low sped spin of about 5,000 g to about 20,000 g of a protozoan lysate.

In some embodiments of the methods, cell free preparations, agents, and compositions of the present invention, the protozoan is of the genus *Trypanosoma*. In some embodiments of the methods, cell free preparations, agents, and compositions of the present invention, the protozoan is *T. cruzi, T. brucei, T.b. gambiense*, or *T.b. rhodesiense*. In some embodiments of the methods, cell free preparations, agents, and compositions of the present invention, the protozoan is of the genus *Leishmania*.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

FIG. 1A is a flowchart of protocol for post-translational import of VSG__117$_{86}$. The various steps and temperatures are depicted. The translation product for VSG__117$_{86}$ is presented along with [$^{14}$C] methylated protein markers (Amersham). FIG. 1B shows the import of VSG__117$_{86}$ into *T. brucei* microsomes (TbRM). VSG__117$_{86}$ mRNA was translated in rabbit reticulocyte lysate and then treated with cycloheximide. Reaction mixtures were incubated with TbRM, followed by proteinase K digestion for 60 minutes on ice. Proteins were resolved by SDS-PAGE and detected by phosphorimaging. Lane 1 is untreated VSG__117$_{86}$; lane 2 is VSG__117$_{500}$ treated with proteinase K; lane 3 is VSG__117$_{86}$ translocated in presence of TbRM; lane 4 is VSG__117$_{86}$ translocated in presence of TbRM but treated with proteinase K; and lane 5 is VSG__117$_{86}$ translocated in presence of TbRM and then permeabilized with 2% NP40 during proteinase K digestion. Rectangular brackets underneath sets of bars denote those data points that were directly compared for quantitation, and the asterisks denote instances where no proteins were detected.

FIGS. 2A and 2B show the effect of protein translocation inhibitors on TbRM. FIG. 2A presents the protocol used for import of VSG__117$_{500}$. In FIG. 2B, SG__117$_{500}$ mRNA was translated in rabbit reticulocyte lysate with 1.5 equivalents *T. brucei* cytosol (pretreated with MAL3-101 (0.3 µM), MAL3-51 (1 µM), CJ21,058 (20 µM) or equisetin (50 µM)) for 60 minutes. The reaction mixtures were treated with cycloheximide (50 µg/ml, final concentration) and incubated with TbRM (one equivalent). The mixture was incubated for 60 minutes at 37° C. and digested with proteinase K digestion (30 µg/ml, final concentration) for 60 minutes on ice. Proteins were resolved by SDS-PAGE and detected by phosphorimaging. In lanes 1 and 2, TbRM were pretreated with DMSO. Lane 1 is untreated VSG__117$_{500}$ with TbRM; lane 2 is VSG__117$_{500}$ incubated with TbRM and treated with proteinase K. In lanes 3 and 4 TbRM were pretreated with MAL3-101. Lane 3 is VSG__117$_{500}$ incubated with TbRM; lane 4 is VSG__117$_{500}$ incubated with TbRM and then treated with proteinase K. In lanes 5 and 6 TbRM pretreated with MAL3-51. Lane 5 is VSG__117$_{500}$ incubated with TbRM; lane 6 is VSG__117$_{500}$ incubated with TbRM and then treated with proteinase K. In lanes 7 and 8 TbRM were pretreated with CJ-21,058). Lane 7 is VSG__117$_{500}$ incubated with TbRM; lane 8 is VSG__117$_{500}$ incubated with ThRM and then treated with proteinase K. In lanes 9 and 10 TbRM were pretreated with equisetin). Lane 9 is VSG__117$_{500}$ incubated with TbRM; lane 10 is VSG__117$_{500}$ incubated with TbRM and then treated with proteinase K.

FIGS. 3A to 3D demonstrate the trypanocidal effect of protein translocation blockers (PTBs). Blood stream form *T. brucei* CA427 were grown in HMI-9 media to the cell density of $10^6$. The cells were then transferred to 96 well plates with the addition of different concentrations of MAL3-101, MAL3-51, CJ-21,058 or equisetin. In controls, DMSO was added. Cell density was calculated at the end of 24 hours, and the graph was plotted. FIG. 3A demonstrates the trypanocidal effect of MAL3-101. FIG. 3B demonstrates the trypanocidal effect of MAL3-51. FIG. 3C demonstrates the trypanocidal effect of CJ-21,058. FIG. 3D demonstrates the trypanocidal effect of equisetin.

FIGS. 4A and 4B demonstrate the effect of anti-trypanosome compounds on a human HeLa Cells. HeLa cells, treated with DMSO, MAL3-101, MAL3-51, CJ-21,058 or equisetin, were subject to a propidium iodide viability assay and analyzed by flow cytometry.

FIG. 5A is MAL3-101; FIG. 5B is MAL3-51; FIG. 5C is CJ-21,058; and FIG. 5D is equisetin.

FIG. 7A demonstrates the effects of MAL3-101 and MAL3-51 (10 µM) on VSG-117$_{86}$ import into *T. brucei* microsomes in the absence or presence of *T. brucei* cytosol. VSG-117$_{86}$ mRNA was translated in rabbit reticulocyte lysate in the absence or presence of *T. brucei* cytosol for 1 hour at 37° C., and then cycloheximide was added to stop protein synthesis. TbRM (1 equivalent) and MAL3-101 (10 µM), MAL3-51 (10 µM), or an equal volume of DMSO was added to the samples on ice, and the mixture was incubated at 37° C. for 1.5 hours for translocation of VSG-117$_{86}$ into the microsomes. Reaction mixtures were treated with proteinase K (PK) for one hour on ice. Proteolysis was terminated with PMSF. Proteins were precipitated with ammonium sulfate, pelleted by centrifugation, resuspended in SDS-PAGE sample buffer, and resolved by Tris-Tricine SDS-PAGE. Gel images were obtained with a phosphorimager and analyzed with Quantity-One software. Reaction mixtures for odd numbered lanes contained TbRM, but not proteinase K; even numbered lanes contained TbRM and proteinase K. Brackets denote lanes that were compared to obtain percentage of VSG-117$_{86}$ import values. FIG. 7B is a graphical representation of data from FIG. 7A. Quantitation of percent VSG import may not correspond to gel image because control lanes (VSG detected in the presence of TbRM without proteinase K) were adjusted to pixel saturation. In FIG. 7C, the effect of MAL3-101 on *T. brucei* growth.

FIGS. 8A to 8D. Effects of NFI028 and CAM741 on import of VSG-117$_{86}$ into *T. brucei* microsomes. FIG. 8A demonstrates the import of VSG-117$_{86}$ into *T. brucei* microsomes in the presence of NFI028 or CAM741 (1 µM). VSG-117$_{86}$ mRNA was translated in rabbit reticulocyte lysate in the presence of *T. brucei* cytosol for one hour at 37° C., and then protein synthesis was stopped by the addition of cycloheximide. TbRM (1 equivalent) and NFI028 or CAM741 (1 µM) or an equal volume of DMSO was added to the translation mixture on ice, and incubated at 37° C. for 1.5 hours. Reaction mixtures were treated with proteinase K (PK) on ice for one hour. Proteolysis was terminated with PMSF. Proteins were precipitated with ammonium sulfate, pelleted, resuspended in SDS-PAGE sample buffer, and resolved by Tris-Tricine SDS-PAGE. Images of radiolabeled proteins were obtained with a phosphorimager and quantitated with Quantity-One software. Samples depicted in odd numbered lanes contained TbRM, but were not treated proteinase K. Reaction mixtures shown in even numbered lanes contained TbRM and were treated with proteinase K. Brackets denote lanes that were compared to each other in order to obtain percentage of VSG-117$_{86}$ import values. FIG. 8B is a graphical representation of data from FIG. 8A. FIG. 8C demonstrates the effect of NFI028 on growth of *T. brucei*. FIG. 8D demonstrates the effect of CAM741 on *T. brucei*.

FIGS. 9A to 9D. Effects of azide, AEE788, and valinomycin on VSG-117$_{86}$ import into *T. brucei* microsomes. FIG. 9A demonstrates the import of VSG-117$_{86}$ into TbRM in the presence of sodium azide or AEE788. VSG-117$_{86}$ mRNA was translated in rabbit reticulocyte lysate in the presence of *T. brucei* cytosol for one hour at 37° C. Cycloheximide was added to stop proteins synthesis. TbRM (1 equivalent) and sodium azide (8 µM), AEE788 (8 µM), an equal volume of microsome buffer (RMB) or DMSO was added to the samples on ice, and the mixtures were incubated at 37 C for 1.5 hours. Reaction mixtures were treated with proteinase K (PK) on ice for one hour. Proteolysis was terminated with PMSF. Proteins were precipitated with ammonium sulfate, pelleted, resuspended in SDS-PAGE sample buffer, and resolved by Tris-Tricine SDS-PAGE. Images of radiolabeled proteins were obtained with a phosphorimager and quantitated with Quantity-One software. Brackets show lanes that were compared to each other in order to obtain percentage of VSG-117$_{86}$ imported into TbRM. Lanes 1, 3, 5, & 7 were treated with TbRM, but not proteinase K. Lanes 2, 4, 6, & 8 were treated with TbRM and proteinase K. FIG. 9B is a graphical representation of data from FIG. 9A. FIG. 9C demonstrates VSG-117$_{86}$ import into TbRM pre-treated with sodium azide, NFI028, or valinomycin was tested using a protocol similar to that described in FIG. 9A, but with the following changes. TbRM that had been pre-incubated for one hour on ice with control buffer (RMB) (lanes 1 and 2), sodium azide (8 µM) (lanes 3 and 4), an equal volume of DMSO (lanes 5 and 6), NFI028 (1 µM) (lanes 7 and 8), valinomycin (0.5 µM) (lanes 9 and 10), or an equal volume of 100% ethanol (lanes 11 and 12) was added to the reaction mixtures and incubated at 37° C. for 1.5 hours. Reaction mixtures depicted in odd lanes contained TbRM, but were not treated with proteinase K; even lanes contained TbRM and were treated with proteinase K. FIG. 9D is a graphical representation of data from panel FIG. 9C.

FIGS. 10A and 10B demonstrate import into *T. brucei* microsomes and hydrophobicity properties of VSG-117$_{86}$, (Gly)$_4$-VSG-117$_{86}$, (Ser)$_4$-VSG-117$_{86}$, (Ala)$_7$-VSG-117$_{86}$, (Ala)$_6$-Ile$_{12}$-VSG-117$_{86}$, and (Ala)$_4$-VSG-117$_{86}$ h-Regions. FIG. 6A demonstrates the import of VSG-117$_{86}$ ("A"), (Gly)$_4$-VSG-117$_{86}$ ("B"), (Ser)$_4$-VSG-117$_{86}$ ("C"), (Ala)$_7$-VSG-117$_{86}$ ("D"), (Ala)$_6$-Ile$_{12}$-VSG-117$_{86}$ ("E"), and (Ala)$_4$-VSG-117$_{86}$ ("F") into *T. brucei* microsomes. mRNAs of VSG-117 variants truncated to 86 amino acids were translated in rabbit reticulocyte lysate. Translation was stopped with cycloheximide, and the translation mixture was supplemented with *T. brucei* microsomes (TbRM), allowing translocation to occur for 1.5 hours at 37° C. Translocation was stopped by incubation of the sample on ice, and import of the protein was tested with proteinase K (PK) digestion on ice for one hour. The samples were precipitated with ammonium sulfate, resolved on Tris-Tricine gels, and analyzed with a phosphorimager and Quantity One software. Gels pictured are representative results. In FIG. 10A (panels "A"-"F"), Lane 1 is no TbRM, no PK; lane 2 is no TbRM, with PK; lane 3 is with TbRM, no PK; and lane 4 is with TbRM, with PK. Brackets denote lanes that were compared to obtain percentage of VSG imported into TbRM. In FIG. 10B peak hydrophobicity values (black bars) were obtained by Kyte-Doolittle hydrophobicity analysis (window=7 amino acids), using LASERGENE (DNASTAR) (version 4.0.3). Percentage of VSG imported (gray bars) from data in FIG. 10A, panels "A"-"F," was calculated by dividing the amount of the residual VSG detected after protease treatment (lane 4) by the amount of the VSG detected after the addition of TbRM with no protease treatment (lane 3) and multiplying the quotient by 100. Quantitation of percent VSG import may not correspond to gel image because control lanes (VSG detected in the presence of TbRM without proteinase K) were adjusted to pixel saturation.

FIG. 11A panel "A" is a time course of importing VSG-117$_{86}$ into TbRM and FIG. 11A panel "B" is a time course of importing (Ala)$_4$-VSG-117$_{86}$ into TbRM. mRNAs of VSG-117's truncated to 86 amino acids were translated in rabbit reticulocyte lysate. Translation was stopped with cycloheximide, and the translation mixture was supplemented with TbRM and incubated at 37° C. In FIG. 11A, translocation was allowed to occur for 0.25 hours (lanes 1 and 2), 0.5 hours (lanes 3 and 4), 1.0 hour (lanes 5 and 6), 1.5 hours (lanes 7 and 8), or 2.0 hours (lanes 9 and 10). Translocation was stopped by incubating the sample on ice. VSG import into TbRM was tested with proteinase K (PK) digestion on ice for one hour. Reaction mixtures were precipitated with ammonium sulfate, resolved on Tris-Tricine gels, and analyzed with a phosphorimager and Quantity One software. Gels pictured are representative results. Lanes 1, 3, 5, 7, and 9 are TbRM present, no PK treatment; lanes 2, 4, 6, 8, and 10 are TbRM present, PK present. Brackets denote lanes that were compared to obtain percentage of VSG imported into TbRM. FIG. 11B is a graphical representation of data in panels A and B of FIG. 11A. Percentage of VSG imported was calculated by dividing the amount of the residual VSG detected after protease treatment by the amount of the VSG detected after the addition of ThRM without protease treatment, and multiplying the quotient by 100.

FIGS. 12A and 12B demonstrate that the rearrangement of h-region sequences affects VSG translocation into TbRM mRNAs of VSGs translated in rabbit reticulocyte lysate. Translation was stopped with cycloheximide. TbRM was added. The mixtures were incubated at 37° C. for 1.5 hours. Import of VSG-117$_{86}$ into TbRM was tested by proteinase K (PK) digestion on ice for one hour. Proteins in the reaction mixture were precipitated with ammonium sulfate, resolved on Tris-Tricine gels, and analyzed with a phosphorimager and Quantity One software. Gels pictured are representative results. In FIG. 12A panels "A"-"F," Lane 1 is no TbRM, no PK; lane 2 is no TbRM, with PK; lane 3 is with TbRM, no PK; lane 4 is with TbRM, with PK. Brackets denote lanes that were compared to obtain percentage of VSG imported into TbRM for each study. h-Regions studied in FIG. 12A were VSG-117$_{86}$ ("A"), (Ala)$_4$-VSG-117$_{86}$ ("B"), scrambled (Ala)$_4$-VSG-117$_{86}$ ("C"), (Ser)$_4$-VSG-117$_{86}$ ("D"), scrambled (Ser)$_4$-VSG-117$_{86}$ ("E"), and (Ala)$_4$-Tyr$_9$-VSG-117$_{86}$ ("F"). FIG. 12B presents peak hydrophobicity values (black bars) obtained by Kyte-Doolittle hydrophobicity analysis (window=7 amino acids), using LASERGENE (DNASTAR) (version 4.0.3). Percentage of VSG imported into TbRM (gray bars) are from data in panels A-F; it was calculated by dividing the amount of the residual VSG detected after protease treatment by the amount of the VSG detected after addition of ThRM without protease treatment, and multiplying the quotient by 100.

FIGS. 13A and 13B demonstrate microsomal import and hydrophobicity properties of VSG-117$_{86}$, (Phe)$_4$-VSG-117$_{86}$, and (Val)$_4$-VSG-117$_{86}$. FIG. 13A presents import of VSG-117$_{86}$ ("A"), (Phe)$_4$-VSG-117$_{86}$ ("B"), and (Val)$_4$-VSG-117$_{86}$ ("C") into *T. brucei* microsomes. mRNAs of VSG-117 variants were translated in rabbit reticulocyte lysate. Translation was stopped with cycloheximide. The reaction mixtures were supplemented with TbRM, and incubated at 37° C. for 1.5 hours. Translocation into TbRM was stopped by incubation of the samples on ice, and import of VSG was tested by proteinase K (PK) digestion on ice for one hour. The samples were precipitated with ammonium sulfate, proteins were resolved on Tris-Tricine gels, and analyzed with a phosphorimager and Quantity One software. Gels pictured are representative results. In FIG. 13A panels "A"-"C," Lane 1 is no TbRM, no PK; lane 2 is no TbRM, with PK; lane 3 is with TbRM, no PK; lane 4 is with TbRM, with PK. Brackets denote pairs of lanes that were compared to obtain percentage of VSG imported into TbRM in each set. In FIG. 13B peak hydrophobicity values (black bars) were obtained by Kyte-Doolittle hydrophobicity analysis (window=7 amino acids), using LASERGENE (DNASTAR) (version 4.0.3). Percentage of VSG imported (gray bars) was calculated from data in FIG. 13A panels A-C by dividing the amount of the residual VSG detected after protease treatment by the amount of the VSG detected after addition of TbRM without protease treatment, and multiplying the quotient by 100.

FIGS. 14A and 14B demonstrate the effect of replacing leucine at h-region position six with phenylalanine, valine, or isoleucine on the translocation of VSG into TbRM. FIG. 14A demonstrates the import of VSG-117$_{86}$ ("A"), (Ala)$_4$-VSG-117$_{86}$ ("B"), (Ala)$_4$-Phe$_6$-VSG-117$_{86}$ ("C"), (Ala)$_4$-Val$_6$-VSG-117$_{86}$ ("D"), and (Ala)$_4$-Ile$_6$-VSG-117$_{86}$ ("E") into *T. brucei* microsomes. mRNAs of VSG-117 were translated in rabbit reticulocyte lysate. Translation was stopped with cycloheximide, and the translation mixture was supplemented with TbRM, followed by incubation at 37° C. for 1.5 hours. Translocation was stopped by incubation of the reaction mixture on ice, and import of proteins was tested by proteinase K (PK) digestion on ice for one hour. Proteins were precipitated with ammonium sulfate, resolved on Tris-Tricine gels, and analyzed with a phosphorimager and Quantity One software. Gels pictured are representative results. In FIG. 14A panels "A"-"E," Lane 1 is with TbRM, no PK; and lane 2 is with TbRM, with PK. Brackets denote pairs of lanes that were compared in order to obtain percentage of VSG imported into TbRM. In FIG. 14B peak hydrophobicity values (black bars) were obtained by Kyte-Doolittle hydrophobicity analysis (window=7 amino acids), using LASERGENE (DNASTAR) (version 4.0.3). Percentage of VSG imported (gray bars) was calculated from data in FIG. 14A panels A-E by dividing the amount of the residual VSG detected after protease treatment by the amount of the VSG detected after addition of TbRM without protease treatment, and multiplying the quotient by 100.

FIG. 15 presents a helical wheel analysis of VSG-117 h-region. The helical wheel model of VSG-117 h-region was generated with LASERGENE (DNASTAR) (Protean Module, version 4.0.3). Arrows indicate h-region "identity components" (IC1, IC2, IC3, IC4, and IC5) in the VSG-117 h-region (see Table 3).

FIG. 16A is a top view of a VSG-117 signal peptide embedded within a *T brucei* Sec61 translocon model. FIG. 16B is a top view. FIG. 16C is a side view of a VSG-117 signal peptide placed between TM2b and TM7 of *T. brucei* Sec61α (TbSec61α). FIG. 16D shows *T. brucei* VSG-117 h-region α-helix interacting with TM2b and TM7 of *T. brucei* Sec61α(not drawn to scale). It is predicted that the h-region of a VSG signal peptide forms an α-helix, and uses h-motif identity components to interact with TM2b and TM7 of TbSec61α. Side-chains of "identity components" of the h-motif are positioned to interact with TM2b and/or TM7 of TbSec61α. The h-motif "identity components" displayed here are from VSG-117 (L4, L6, L8, L9, and A11), and the TbSec61 translocon is a "homology model" of the *T. brucei* Sec61 translocon based on the X-Ray crystal structure from *Methanococcus jannaschii* (Van den Berg et al., 2004, *Nature;* 427:36-44).

FIGS. 17A to 17D demonstrates cell-free protein import into *T. brucei* ER membranes. FIG. 17A is a flow chart of the protocol for post-translational Import of full length VSG. Depicted are the various steps, duration and temperatures at which reactions took place. FIG. 17B demonstrates the import of full length VSG_117 into TbRM. VSG_117 mRNA was translated in rabbit reticulocyte lysate for 15 minutes and then cycloheximide (50 μg/ml, final concentration) was added. Cytosol from *T. brucei* was also added to all reactions. Reaction mixtures were incubated with TbRM (one equivalent) for 45 minutes (37° C.) followed by proteinase K digestion (300 μg/ml, final concentration) on ice for 60 minutes. Proteins were resolved by SDS-PAGE and detected by phosphorimaging. Lane 1 is VSG_117 translated in reticulocyte lysate; lane 2 is VSG_117 digested with proteinase K; lane 3 is VSG_117 digested with proteinase K in the presence of NP-40 (2%); lane 4 is VSG_117 incubated with TbRM; lane 5 is VSG_117 incubated with TbRM and digested with proteinase K; lane 6 is VSG_117 translocated into TbRM and then permeabilized with 2% NP-40 during proteinase K digestion. FIG. 17C demonstrates translocation of VSG_MVAT7 into TbRM. Lane 1 is VSG_MVAT7 translated in reticulocyte lysate; lane 2 is VSG_MVAT7 produced in reticulocyte lysate and digested with proteinase K. Lane 3 is VSG_MVAT7 incubated with TbRM; lane 4 is VSG_MVAT7 incubated with TbRM and then challenged with proteinase K;

lane 5 is VSG_MVAT7 incubated with TbRM, permeabilized with NP-40 (2%), and digested with proteinase K. FIG. 17D demonstrates that a signal peptide is required for VSG_ $117_{500}$ ΔSP translocation. VSG_$117_{500}$ΔSP mRNA was translated in a rabbit reticulocyte lysate with T brucei cytosol (1.5 equivalents) for 60 minutes, and treated with cycloheximide (50 μg/ml, final concentration). VSG_$117_{500}$ΔSP was incubated with TbRM (one equivalent) for 60 minutes at 37° C. and digested with proteinase K (120 μg/ml, final concentration) for 60 minutes on ice. Proteins were separated by SDS-PAGE and radiolabeled polypeptides were detected by phosphorimaging. Lane 1 is untreated VSG_$117_{500}$ΔSP; lane 2 is VSG_$117_{500}$ΔSP treated with proteinase K; lane 3 is VSG_$117_{500}$ΔSP incubated with TbRM; lane 4 is VSG_$117_{500}$ΔSP incubated with TbRM and treated with proteinase K. Rectangular brackets underneath sets of bars denote those data points that were directly compared for quantification, and the asterisks denote instances where no signal was detected.

FIGS. 18A and 18B. MAL3-101, equisetin, and CJ-21,058 inhibit VSG translocation into TbRM. FIG. 18A presents the protocol used for import of VSG_117. In FIG. 18B, VSG_117 mRNA was translated in rabbit reticulocyte lysate with 1.5 equivalents *T. brucei* cytosol pretreated with MAL3-101 (3 μM), MAL3-51 (10 μM), CJ-21,058 (20 μM) or equisetin (50 μM)) for 60 minutes. The reaction mixtures received cycloheximide (50 μg/ml, final concentration) and were incubated with TbRM (one equivalent). After incubation at 37° C. for 60 minutes, reaction mixtures were transferred to an ice-water bath and treated with proteinase K (30 μg/ml, final concentration) for 60 minutes. Proteins were resolved by SDS-PAGE and detected by phosphorimaging. Lane 1 is VSG_117 incubated with TbRM; lane 2 is VSG_117 digested with proteinase K after incubation with TbRM; lane 3 is VSG_117 incubated with MAL3-101 in the presence of TbRM; lane 4 is VSG_117 and TbRM incubated with MAL3-101 and then digested with proteinase K; lane 5 is VSG_117 incubated with MAL3-51 and TbRM; lane 6 is VSG_117 incubated with TbRM in the presence of equisetin; lane 7 is VSG_117 incubated with ThRM; lane 8 is VSG_117 incubated with equisetin and digested with proteinase K; lane 9 is VSG_117 incubated with CJ-21,058 and TbRM; lane 10 is VSG_117 incubated with TbRM and CJ-21,058 and digested with proteinase K. For quantitation, each proteasedigested sample was compared to a control experiment containing the drug but without protease addition. Thus, lane 2 is compared with lane 1 while lane 4 is compared to lane 3, and so on.

FIGS. 19A to 19D. VSG_117 bound to ThRM is Resistant to Carbonate Extraction and Floats on a Sucrose Cushion. FIG. 19A presents SDS-PAGE of carbonate extraction of VSG-117 in the absence or presence of TbRM. Lanes 1 and 2 represent VSG-117 carbonate extraction without TbRM. Lanes 3 and 4 represent VSG-117 carbonate extraction with TbRM present. "S" denotes proteins precipitated from the supernatant of the 230,000×g step while "P" represents proteins recovered from the 230,000×g centrifugation step. Brackets denote lanes that were compared to obtain a percentage to total VSG-117 present. FIG. 19B is a quantitation of data in FIG. 19A; the percentage of total VSG-117 present is expressed as the amount of VSG detected in a single lane divided by the sum of the amount of VSG detected in the supernatant and pellet lanes. FIG. 19C presents Tris-Tricine SDS-PAGE after he floatation of VSG-117 in the absence (top panel) or presence (bottom panel) of TbRM. Lane 1 represents proteins obtained from the 0.25 M sucrose layer; lane 2 represents proteins obtained from the 1.5 M sucrose layer; lane 3 represents proteins obtained from the top 2.3 M sucrose layer; and lane 4 represents proteins recovered from the bottom 2.3 M sucrose layer and those protein pelleted from the 100,000×g centrifugation step. FIG. 19D is a quantitation of the data in FIG. 19C. Percentage of total VSG-117 present is expressed as the amount of VSG detected in a single lane divided by the sum of VSG detected in lanes 1-4. "*" Represents 0% VSG-117 detected.

DETAILED DESCRIPTION OF PREFERRED EMBODIMENTS OF THE INVENTION

Figure 1:
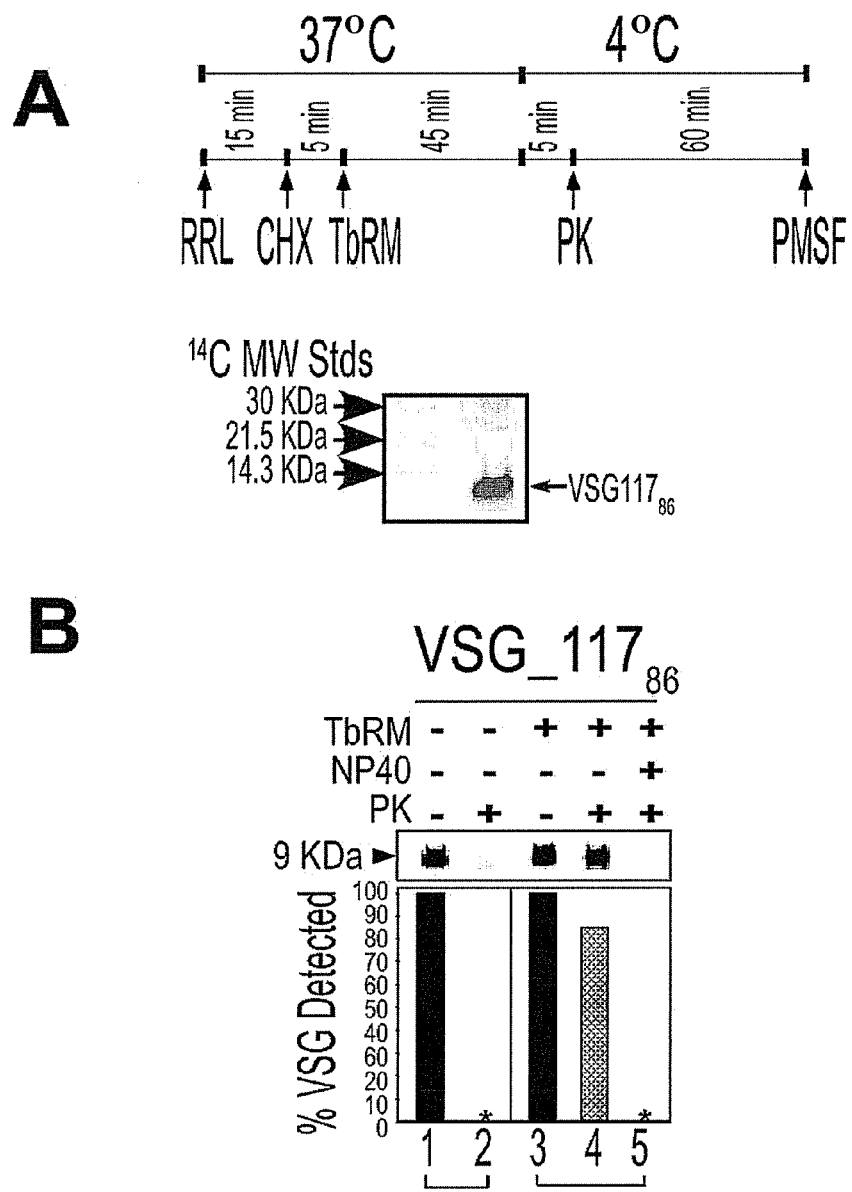
FIGS. 1A and 1B demonstrate cell-free protein import into *T. brucei* endoplasmic reticulum (ER) membranes.

The present invention provides cell free preparations of protozoan microsomes, wherein the cell free preparation of protozoan microsomes demonstrate the ability to translocate a protozoan polypeptide into the microsome, methods of preparing cell free preparations of protozoan microsomes, and methods of using cell free preparations of protozoan microsomes. As used herein, a microsome is a small vesicle that is derived from fragmented endoplasmic reticulum (ER). Microsomes may be prepared from a lysate of protozoan cells. Microsomes may be purified and isolated from other cellular components, such as, for example, unbroken cells, other cellular organelles, nuclei, mitochondria, soluble enzymes, and/or other soluble proteins of the cellular cytosol.

The protozoan microsomes of the present invention may be prepared from any of a variety of protozoa, including, for example, kinetoplastid protozoa, such as for example, protozoa of the *Blastocrithidia, Crithidia, Endotrypanum, Herpetomonas, Leishmania, Leptomonas, Phytomonas, Trypanosoma*, and *Wallaceina* genera. In preferred embodiments, the protozoan is of the genus *Trypanosoma*, including, but not limited to, *T. cruzi, T. brucei, T.b. gambiense*, and *T.b. rhodesiense*. In some embodiments, the protozoan is of the genus *Leishmania*, including, for example, *Leishmania major*. Notable trypanosomal diseases include trypanosomiasis (African Sleeping Sickness and South American Chagas Disease, caused by species of *Trypanosoma*) and leishmaniasis (caused by species of *Leishmania*).

The purified and isolated microsomes of the present invention demonstrate the capability of translocating polypeptides across the endoplasmic reticulum (ER). In some embodiments, the polypeptide is a polypeptide of protozoan origin or is a polypeptide of non-protozoan origin, with a translocation signal sequence of protozoan origin. Translocated polypeptides may be, for example, plasma membrane polypeptides or soluble polypeptides. Translocation of a polypeptide into the microsome may be assayed by any of a variety of methods, including, but not limited to, protection of the translocated polypeptide from proteinase, protection of the polypeptide from endogenous detergent, and/or loss of protease protection after detergent permeabilization of the microsome.

To prepare cell free microsomes, protozoan cells may be obtained by any of the many methods known to the skilled artisan. Protozoan cells may be treated in a manner to disrupt the protozoan cells, so that the protozoan cell membrane is broken open. This process is known as homogenization of the protozoan cell or preparation of a protozoan cell lysate. Protozoan cells may be homogenized by any of a variety of methods, including, but not limited to, osmotic alteration, mechanical disruption, sonification, enzymatic digestion, detergent-based cell lysis, or a combination of two or more of these methods. Methods of mechanical disruption include, but are not limited to, dounce homogenization, mortars, pestles, nitrogen burst methods, french pressure cell press and pumped-fluid processors.

Microsomes may be concentrated and separated from other cellular organelles by differential centrifugation of a protozoan cell lysate to sediment out unbroken cells, nuclei, mitochondria, and other cellular organelles, whereas soluble cytosolic proteins and microsomes remain in the supernatant. Such centrifugation may be a low speed centrifugation at a speed of less than about 5,000 g, including, but not limited to, for example, about 1,000 g, about 2,000 g, about 3,000 g, about 4,000 g, about 5,000 g, or less, or about 2,000 to about 4,000 g.

Microsomes may be separated from soluble cytosolic proteins by differential centrifugation to sediment out the microsomes formed by fragments of ER membrane, whereas the soluble cytosolic proteins remain in the supernatant and the microsomes are found in the pellet. Such microsomes may be pelleted by a speed of about 5,000 g to about 20,000 g. Such microsomes may be pelleted at a speed of about 5,000 g, about 10,000 g, or about 12,000 g to about 14,000 g, about 16,000 g, about 18,000 g, or about 20,000 g. The pelleted microsomes may be resuspended, for example, in a resuspension solution. Such a buffer may be isotonic and/or pH buffered.

Centrifugation is a process that involves the use of the centrifugal force for the separation of mixtures and is widely used in industry and laboratory settings. More-dense components of the mixture migrate away from the axis of the centrifuge. Chemists and biologists may increase the effective gravitational force on a test tube so as to more rapidly and completely cause the precipitate ("pellet") to gather on the bottom of the tube. The remaining solution is properly called the "supernate" or "supernatant liquid." Protocols for centrifugation typically specify the amount of acceleration to be applied to the sample or a rotational speed such as revolutions per minute (rpm). The acceleration is often quoted in multiples of "g," the acceleration due to gravity at the Earth's surface. This distinction is important because two rotors with different diameters running at the same rotational speed will subject samples to different accelerations. The acceleration can be calculated as the product of the radius and the square of the angular velocity using the formula:

$$g = RCF = 0.00001118 \times r \times N^2,$$

where r=rotational radius (centimeter, cm) and N=rotating speed (revolutions per minute, r/min). To avoid having to perform a mathematical calculation every time, nomograms for converting RCF to rpm for a given rotor of a given radius are widely available.

The present invention also includes a purified cytosol preparation of the supernatant from which microsomes have been removed. This cytosol preparation may be subject to additional centrifugation and/or purification procedures. For example, such a cytosol preparation may the supernatant of a high speed of greater than 20,000 g, including, but not limited to, speeds of about 65,000×g, about 75,000 g, about 100,000 g, about 120,000 g, about 180,000 g, and about 200,000 g. This cytosol preparation may include purified soluble cytosolic proteins that facilitate the translocation of a polypeptide across a microsome.

The present invention includes any of the microsomes, methods of making microsomes, and methods of making cytosol preparations described herein, including, but not limited to, any of those described in the Examples included herewith.

For example, *T. brucei* microsomes, also referred to herein as "TbRM," may be prepared by obtaining blood stream trypanosomes from the blood of infected rats. Trypanosomes may be mechanically broken by homogenization, for example, with a dounce homogenizer. A homogenization buffer of about 250 mM Sucrose, about 50 mM HEPES-KOH, about 50 mM KOAc, about 6 mM Mg(OAc)$_2$, about 1 mM EDTA, about 1 mM DTT, about 1 µg/ml TLCK, about 5 µg/ml leupeptin, and about 0.5 mM PMSF (final concentrations) may be used. The homogenized trypanosome lysate may be centrifuged in a low speed spin of less than about 5,000 g to remove unbroken cells, nuclei, mitochondria, and other cellular organelles. The supernatant of the low speed spin, containing the protozoan microsomes may then be centrifuged at a higher speed, for example, about 5,000 to about 20,000 g, to pellet the microsomes. Microsomes may be resuspended in, for example, rough microsome buffer (RMB) of about 250 mM Sucrose, about 50 mM HEPES-KOH, about 50 mM KOAc, about 6 mM Mg(OAc)$_2$, about 1 mM DTT, about 0.5 µg/ml TLCK, and about 2.5 µg/ml leupeptin. Microsome concentration may be determined, for example, by measuring absorbance at 260 nm. Concentration of microsomes may be adjusted (with, for example, RMB) to $OD_{260}$ nanometers (nm) of 50. In some aspects, one equivalent of TbRM has an $OD_{260}$ of 50 nm.

The present invention also includes a purified cytosol preparation of the supernatant from which microsomes have been removed. This cytosol preparation may be subject to additional centrifugation and/or purification procedures. For example, the supernatant obtained during the preparation of TbRM described above may be centrifuged at a speed greater than 20,000 g. The resulting supernatant may be further concentrated by ultrafiltration. Concentration of the cytosol preparation may be adjusted (with 0.1% SDS) to $OD_{280}$ nanometers (nm) of 50. In some aspects, one equivalent of cytosol has an $OD_{280}$ of 50 nm. The cytosol preparation may be quick-frozen in liquid nitrogen, and stored at −80° C. Such purified cytosol preparations may be added to a cell free microsome preparation to increase, improve or facilitate the translocation of polypeptides. The translocation of larger polypeptides may, in particular, be enhanced by the addition of such a cytosol preparation.

Signal peptides for translocation across the endoplasmic reticulum are essential for protein traffic through the secretory system in eukaryotes, including protozoans. In addition, lumenal proteins of the ER, Golgi complex, lysosomes and plasma membrane proteins with exoplasmic domains depend on signal peptides for correct intracellular targeting. Parasite surface proteins are critical for the uptake of nutrients, such as, for example, iron, signal transduction, and cell viability. Therefore, an understanding of how proteins arrive at the plasma membrane of a protozoan is important for understanding viability and virulence in these organisms.

In *T. brucei*, an eukaryote that causes human African trypanosomiasis, the defining features of signal peptides are not known and the ER protein translocation machinery has not been fully characterized. Signal peptides of T brucei are not compatible with the canine microsomal protein import system (Al-Qahtani et al., 1998, Biochem J; 331:521-529 and Ramirez et al., 1999, *J Eukaryot Microbiol;* 46(6):557-65) that is widely used to study translocation of proteins into eukaryote ER (Connolly et al., 1989, *J Cell Biol;* 108(2):299-307). For example, in a canine microsomal system, signal peptides from *T. brucei*, namely VSG_117, VSG_221, VSG_MVAT7 and BiP, fail to direct ER import of proteins. In control experiments, pp MF and *E. coli* β-lactamase were imported into the canine microsomes. Replacement of the signal sequence of VSG_117 with a signal sequence from pp MF led to import of the *T. brucei* protein by canine microsomes. Thus, the trypanosome signal peptide is incompatible with the canine ER protein import machinery. Further, trypanosomatid proteins expressed in human and insect cells are mistargeted. Attempts to secrete recombinant *L. major* gp63 from insect Sf9 cells failed. When the trypanosomatid signal sequence was replaced with a baculovirus signal peptide, gp63 was secreted. When gp82 from *T. cruzi* was expressed in murine Vero cells the protein was not targeted to the plasma membrane where it is normally found in the parasite. Replacement of the *T. cruzi* signal peptide with a signal sequence from influenza virus hemagglutinin targeted gp82 to the plasma membrane of Vero cells. Thus, both in vitro and in vivo, trypanosomatid signal peptides seem to be incompatible with ER protein translocation systems in other eukaryotes.

The cell free microsome preparation of the present invention may be used in methods translocating protozoan polypeptides across the microsomal ER membrane. The diversity and nonequivalence of signal sequences in vertebrate is receiving attention (Martoglio and Dobberstein, 1998, *Trends Cell Biol;* 8(10):410-5; Rutkowski et al., 2003, *J Biol Chem;* 278(32):30365-72; Hegde and Bernstein, 2006, *Trends Biochem Sci;* 31(10):563-712006; Harant et al., 2006, *J Biol Chem;* 281(41):30492-502; and Besemer et al., 2005, *Nature;* 436(7048):290-3). Since trypanosome and vertebrate signal sequences and ER translocation mechanisms have intrinsic differences (Al-Qahtani et al., 1998, *Biochem J;* 331:521-529), the *T. brucei* ER protein import pathway provides a target for drug discovery.

The novel cell free microsome system for trypanosome ER protein import of the present invention is prepared from membranes from *T. brucei* (TbRM) and is able, unlike canine microsomes, to import proteins with trypanosome signal peptides. Thus, the cell free microsystem of the present invention provides for the identification and characterization of *T. brucei* signal sequences and other protozoan species. The present invention includes polypeptides including T brucei signal sequences, including, but not limited to, any of the peptide sequences set forth in Example 7. Protein translocation of secretory proteins into the endoplasmic reticulum (ER) in eukaryotes enables polypeptide entry into the secretory pathway, which is important for the viability of the human protozoan parasite *Trypanosoma brucei*. An N-terminal signal peptide of precursor proteins is essential for entry into the ER. A hydrophobic core, or h-region, of the signal peptide is required for signal peptide activity. h-Regions are thought to be composed of random hydrophobic amino acids, whose peak hydrophobicity governs activity of signal peptides. Example 7 re-evaluated these concepts using a trypanosome microsomal system for import of a variant surface glycoprotein, VSG-117 and found that h-region peak hydrophobicity alone does not dictate signal peptide activity. Moreover, this example identified conserved tri-component peptide motifs (including, L-L-x-[AILV], L-x(1,2)-L-[AILV], and L-x(2,3)-L-[AILPV]) in h-regions of *T. brucei* signal peptides.

The cell-free microsome translocation system of the present invention can be used to identify candidate drugs for the treatment and prevention of diseases caused by protozoa. As described in the examples included herewith, several small molecules, including two natural compounds of fungal origin, CJ-21,058 (Sugie et al., 2002, *J Antibiot (Tokyo);* 55(1):25-9) and equisetin, a SecA inhibitor (Vesonder et al., 1979, *J Antibiot (Tokyo);* 32(7):759-61), block import of a VSG polypeptide into TbRM, and killed *T. brucei*. Since trypanosome post-translational ER protein import may require molecular chaperones, inhibitors of Hsp70 were also tested. MAL3-101 (Fewell et al., 2004, *J Biol Chem;* 279(49): 51131-40) blocked protein translocation into TbRM and was trypanocidal at sub-micromolar concentrations. These studies establish the ER protein import pathway as a valid target for discovery of anti-trypanosome drugs, and presents the cell free microsome system of the present invention as system for performing focused screens of trypanocidal compounds that inhibit protein import into the ER.

The cell free microsome system of the present invention may be used for the screening and identification of agents for the treatment and/or prevention of a protozoan infection. Such cell free microsome systems may be used for the screening and identification of agents that kill, inhibit the growth, and/or inhibit the reproduction of a protozoan. For example, one may find new anti-trypanosome compounds by either screening chemical libraries or by rational drug design. In rational drug design, one aims to find small molecules that inhibit the function of proteins that are essential for parasite viability (McKerrow, 1996, *Biologicals;* 24(3):207-8; Barrett et al., 1999, *Trends Microbiol;* 7(2):82-8; Hammarton et al., 2003, *Prog Cell Cycle Res;* 5:91-101; Seizer et al., 1999, *Proc Natl Acad Sci USA;* 96(20):11015-22; Naula et al., 2005, *Biochim Biophys Acta;* 1754(1-2):151-9; and Gelb et al., *Mol Biochem Parasitol;* 126(2):155-63).

Assaying for such agents can include one or more of the following: preparing a microsome preparation, preparing a cytosol preparation, contacting a microsome preparation and/or a cytosol preparation with an agent, determining translocation into a microsome in the presence and absence of an agent, and/or evaluating the functional effects of the agent on activity. A wide variety of methods may be used to evaluate translocation, including, but not limited to, any of those described herein.

The cell free protozoan microsomes of the present invention demonstrate the capability of translocating polypeptides across the ER. As used herein, the term "polypeptide" refers to a polymer of amino acids linked by peptide bonds and does not refer to a specific length of a polymer of amino acids. Thus, for example, the terms peptide, oligopeptide, protein, and enzyme are included within the definition of polypeptide. A polypeptide may be, for example, an intact protozoan polypeptide, such as, for example, an intact VSG polypeptide, a truncated protozoan polypeptide, such as, for example, a truncated VSG polypeptide (including, for example, any of those described in the examples included herewith), a chimeric polypeptide, containing, for example, amino acid residues from two different species, such as, for example, trypanosome and human amino acid sequences, and altered polypeptides, in which selected amino acid residues have been changed, for example, by site directed mutagenesis.

As used herein, the term isolated means that a preparation that is either removed from its natural environment or synthetically derived, for instance by recombinant techniques, or chemically or enzymatically synthesized. An isolated polynucleotide denotes a polynucleotide that has been removed from its natural genetic milieu and is thus free of other extraneous or unwanted coding sequences, and is in a form suitable for use within genetically engineered protein production systems. When applied to a protein/polypeptide, the term isolated indicates that the protein is found in a condition other than its native environment. In a preferred form, the isolated protein is substantially free of other proteins.

The present invention includes agents that modulate ER translocation in a cell free protozoan microsome preparation. The present invention includes derivatives and analogs of such agents. As used herein the term "agent" includes both protein and non-protein moieties. In one embodiment, the agent is a small molecule. The agent may be derived from a library of low molecular weight compounds or a library of extracts from plants or other organisms. Such agents and derivatives and analogs thereof may be identified by any of the methods discussed herein. The present invention includes compositions of one or more such agents and/or derivatives and analogs thereof. A composition may be a pharmaceutical composition. A composition may include a pharmaceutically acceptable carrier. The term "pharmaceutically acceptable," as used herein, means that the compositions or components thereof so described are suitable for use in contact with human skin without undue toxicity, incompatibility, instability, allergic response, and the like. As used herein in vitro is in cell culture, ex vivo is a cell that has been removed from the body of a subject, and in vivo is within the body of a subject.

The present invention includes methods of treating or preventing a protozoan infection in a subject by administering to the subject an effective amount of an agent that modulates the ER translocation of a polypeptide in a cell free preparation of protozoan microsomes. Such an agent may be identified by the methods described herein. As used herein "treating" or "treatment" includes both therapeutic and prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. The present invention includes methods of treating or preventing a protozoan infection in a subject by administering to the subject an effective amount of MAL3-101, CJ-21,058, AEE788, equisetin, CAM741, NF 1028, and/or derivatives thereof.

The present invention includes methods of killing, inhibiting the growth of, and/or inhibiting the reproduction of a protozoan by contacting the protozoan with an agent modulates the ER translocation of a polypeptide in a cell free preparation of protozoan microsomes. Such an agent may be identified by any of the methods described herein. A modulation of ER translocation includes a reduction in the rate of ER translocation, an inhibition of ER translocation. In some aspect, a modulation of ER translocation is the halting or prevention of ER translocation. In some aspect, a modulation of ER translocation is an increase in the rate of ER translocation, an enhancement in ER translocation. As used herein, the term "inhibit" means prevent, decrease, or reverse. In some embodiments, modulation is an increases, activation, or stimulation of ER translocation. The present invention includes methods of killing, inhibiting the growth of, and/or inhibiting the reproduction of a protozoan by contacting the protozoan with MAL3-101, CJ-21,058, AEE788, equisetin, CAM741, NF 1028, and/or derivatives thereof.

The present invention is illustrated by the following examples. It is to be understood that the particular examples, materials, amounts, and procedures are to be interpreted broadly in accordance with the scope and spirit of the invention as set forth herein. For any method disclosed herein that includes discrete steps, the steps may be conducted in any feasible order. And, as appropriate, any combination of two or more steps may be conducted simultaneously.

EXAMPLES

Example 1

Preparation of T. brucei Microsomes

To prepare T. brucei microsomes (TbRM), blood stream trypanosomes were obtained from the blood of infected rats, and purified by DE-52 chromatography. Cells ($1\times10^{10}$) were resuspended in 5 milliliter (ml) of homogenization buffer (made up of 250 mM Sucrose, 50 mM HEPES-KOH, 50 mM KOAc, 6 mM Mg(OAc)$_2$, 1 mM EDTA, 1 mM DTT, 1 µg/ml TLCK, 5 µg/ml leupeptin, 0.5 mM PMSF (final concentrations). Two and half ml of resuspended cells were added to pre-chilled dounce homogenizer where they were lysed with 80 strokes of a pestle (specially selected for its tight-fitting to the homogenizer) on ice. After a one minute rest, another after 80 strokes was administered with the pestle. Homogenized cells were recovered and kept on ice while the remaining 2.5 ml of resuspended cells were being broken. Both sets of homogenized lysates were pooled and centrifuged (2,000 rpm, 10 min, 4° C.) in microfuge tubes. The supernatants were pooled, aliquoted into new microfuge tubes, and centrifuged at 12,000 rpm for 20 min at 4° C., and each pellet was resuspended in 50 µl (total volume) of fresh rough microsome buffer (RMB) (250 mM Sucrose, 50 mM HEPES-KOH, 50 mM KOAc, 6 mM Mg(OAc)$_2$, 1 mM DTT, 0.5 µg/ml TLCK, 2.5 µg/ml leupeptin). The T. brucei microsome (TbRM) concentration was determined by measuring absorbance at 260 nm. Concentration of TbRM was adjusted (with RMB) to OD$_{260}$ nanometers (nm) of 50, aliquoted, quick frozen in liquid nitrogen, and stored at −80° C. One equivalent of TbRM has an OD$_{260}$ of 50 µm. Supernatant from the 12,000 rpm centrifugation was also saved.

Various unique properties distinguish T. brucei from canine pancreas microsomal system. Protein import into the endoplasmic reticulum has been studied extensively in vitro using a canine microsomal system (reviewed in Martoglio and Dobberstein, 1996, Trends Cell Biol; 6:142-147 and Walter and Blobel, 1983, Methods Enzymol; 96:84-93). Canine microsomes import protein co-translationally. They cannot import pre-synthesized protein. Consequently, there is no hard evidence that canine ER protein import requires cytoplasmic chaperones (such as, for example, Hsp70 and Hsp40). Finally, canine microsomal import system cannot recognize trypanosome signal peptides (Al-Qahtani et al., 1998, Biochem J; 331:521-529).

In contrast to the canine microsomal system, T. brucei microsomes (ThRM) of the present invention depend on trypanosome signal peptides to translocate protein into the endoplasmic reticulum (ER). Further, import of protein into TbRM can occur post-translationally, unlike the canine pancreatic system. Finally, translocation of full-length protein into TbRM requires cytosol from the parasite, and is inhibited by a small molecule that interferes with Hsp70 function, suggesting that Hsp40 is crucial for import of protein into TbRM.

Example 2

Endoplasmic Reticulum Protein Import as a Target for Anti-Trypanosome Drug Discovery Caused by Trypanosoma brucei, human African trypanosomiasis is an emerging disease for which new drugs are needed. As an extracellular parasite in its vertebrate host, expression of proteins, including variant surface glycoprotein (VSG) on the plasma membrane is crucial for establishment and maintenance of an infection. Transport of the majority of proteins to the plasma membrane involves translocation into the endoplasmic reticulum (ER). Prevention of protein import into the parasite ER would be an effective target for the discovery of new anti-trypanosome compounds. In this example, a microsomal system that imports a model VSG__117 (VSG__117$_{86}$) substrate was developed. This in vitro system was used in a focused screen to identify small molecules that block import of proteins into the microsomes from

*T. brucei* (TbRM). Protein translocation blockers were then tested for anti-trypanosome effects. MAL3-101, an inhibitor of Hsp40-regulated Hsp70 ATPase, blocked import of VSG__117$_{86}$ into TbRM. Similarly, equisetin and CJ-21,058 also inhibited import of VSG__117$_{86}$ into TbRM. In tests of trypanocidal activity, all compounds that blocked protein import into TbRM were toxic to trypanosomes. The concentrations at which fifty percent of parasites were killed ($IC_{50}$) were 125 nM for MAL3-101, 3.3 µM for equisetin, and 7 µM for CJ-21,058. MAL3-101 and equisetin did not have discernible effects on human HeLa cells at concentrations that killed *T. brucei*. These observations establish TbRM protein import as a rapid assay for anti-trypanosome drug discovery. Drugs, including small molecule drugs, may be screened in the TbRM protein import system of the present invention to identify those that inhibit protein import into the microsomes and potentially kill the parasite. The TbRM protein import system of the present invention will identify lead compounds for anti-trypanosome drug discovery. TbRM protein import system of the present invention has identified MAL3-101, equisetin, and CJ-21,058 as lead compounds for anti-trypanosome drug discovery.

Materials and Methods

Reagents and chemicals. Plasmid pVSG__117 (Bangs, et al., 1986, J Cell Biol; 103:255-263) was provided by Dr. J. Bangs (University of Wisconsin, Madison). CJ-21,058 and equisetin were gifts from Pfizer Inc., (New York, N.Y.). Rabbit reticulocyte lysate (RRL) and methionine/cysteine-free amino acid mixture was purchased from Promega (Madison, Wis.). [$^{35}$S]Redivue Promix™ was purchased from Amersham Biosciences (Piscataway, N.J.), etoposide was purchased from Sigma (St. Louis, Mo.), and propidium iodide was purchased from Invitrogen (Carlsbad, Calif.). Ampliscribe™ T7 in vitro transcription kit was purchased from Epicentre Technologies (Madison, Wis.).

DNA Templates and RNA Synthesis in vitro. DNA template (one µg) was transcribed using the Ampliscribe™ T7 kit (Epicentre Technologies) following the manufacturer's protocol. A template for in vitro transcription was obtained by PCR using the forward primer ccctaatacg actcactata gggaggaggg tttttaccat ggactgccat acaaaggag (SEQ ID NO: 1), which contains a T7 promoter (italicized), and a translation enhancer (bolded) (Al-Qahtani and Mensa-Wilmot, 1996, *Nucleic Acids Res;* 24:1173-1174). The first 21 nucleotides of the VSG__117 coding sequence are in regular style font. The reverse primer for VSG__117$_{86}$ was cgaacaacga aggggttctt atagtgcgta gattcgtagc ttcgtttc (SEQ ID NO:2), and includes a HinfI site and nucleotides 78-86 of the coding region of VSG__117. One µl (1MBU) of RNase free DNase I was added to the reaction and allowed to incubate at 37° C. for 15 minutes (1 MBU digests 1 µg of pUC19 DNA in 10 minutes). An equal volume of TE-saturated phenol/chloroform was then added to the reaction, which was vortexed, and centrifuged (13,200 rpm, 15 minutes) at 4° C. The aqueous phase was withdrawn, combined with an equal volume of chloroform, vortexed and centrifuged (15 minutes, 13,200 rpm, 4° C.). To this aqueous phase 0.3M sodium acetate (final concentration) and precipitated with ethanol at −20° C. overnight. The precipitate was recovered by centrifugation (13,200 rpm, 4° C. for 15 minutes), rinsed with 70% ethanol, air-dried and dissolved 40 ml of nuclease free water. The RNA concentration was determined by measuring the absorbance at 260 nm, and confirmed by analysis with agarose gel electrophoresis and ethidium bromide staining.

Preparation of *T. brucei* microsomes (TbRM). Blood stream trypanosomes were obtained from the blood of infected rats, and purified by DE-52 chromatography. Cells ($1 \times 10^{10}$) were resuspended in 5 ml of homogenization buffer (made up of 250 mM Sucrose, 50 mM HEPES-KOH, 50 mM KOAc, 6 mM Mg(OAc)$_2$, 1 mM EDTA, 1 mM DTT, 1 µg/ml TLCK, 5 µg/ml leupeptin, 0.5 mM PMSF (final concentrations). Two and half ml of resuspended cells were added to pre-chilled dounce homogenizer where they were lysed with 40 strokes of a pestle (specially selected for its tight-fitting to the homogenizer) on ice. After a one minute rest, another after 40 strokes was administered with the pestle. Homogenized cells were recovered and kept on ice while the remaining 2.5 ml of resuspended cells were being broken. Both sets of homogenized lysates were pooled and centrifuged (2,000 rpm, 10 minutes, 4° C.) in microfuge tubes. The supernatants were pooled, aliquoted into new microfuge tubes, and centrifuged at 12,000 rpm for 20 minutes at 4° C., and pellets resuspended in 40 µl (total volume) of fresh rough microsome buffer (RMB) (250 mM Sucrose, 50 mM HEPES-KOH, 50 mM KOAc, 6 mM Mg(OAc)$_2$, 1 mM DTT, 0.5 µg/ml TLCK, 2.5 µg/ml leupeptin). The *T. brucei* microsome (TbRM) concentration was determined by measuring absorbance at 260 nm. Concentration of TbRM was adjusted (with RMB) to $OD_{260}$ nm of 50, aliquoted, quick frozen in liquid nitrogen, and stored at −80° C. One equivalent of TbRM has an $OD_{260}$ of 50). Supernatant from the 12,000 rpm centrifugation was also saved.

Preparation of cytosol from *T. brucei*. The supernatant obtained during the preparation of TbRM described above was centrifuged at 65,000×g (60 minutes, 4° C., Beckman TLA 100.3 rotor). Two milliliters of the resulting supernatant was concentrated twenty-fold by ultrafiltration with a Centricon-10 filter (Amicon). The retentate was retrieved, an aliquot was diluted 50-fold with 0.1% SDS, and the $OD_{280}$ obtained. One equivalent of cytosol has an $OD_{280}$ of 50. Aliquots were quick-frozen in liquid nitrogen, and stored at −80° C.

Protein import into TbRM. Two micrograms (µg) of RNA encoding a truncated substrate (e.g., VSG__117$_{86}$) was translated in 40111 of a reaction mixture containing 20 µl rabbit reticulocyte lysate, 60 µM amino acid mixture (-Met, -Cys), and 2.4 µCi [$^{35}$S]Promix. The reaction was incubated at 37° C. for 15 minutes. Cycloheximide (50 µg/ml, final concentration) was used to stop further translation, and the mixture was divided into two portions. *T. brucei* microsomes (ThRM) (1 equivalent) was added to one aliquot, and to the other portion an equal volume of RM buffer was added. The reactions were incubated at 37° C. for 45 minutes for protein import into TbRM to take place post-translationally.

Each reaction mixture was divided into three (each 10 µl) and treated with one of the following on ice for one hour: (I) RM buffer; (ii) 30 µg/ml protease K; (iii) nonidet P-40 (NP-40) (2%, final concentration) followed by protease K (30 µg/ml, final concentration). PMSF (20 mM final concentration) was added to stop protease K digestion. Samples were precipitated with an equal volume of cold (NH$_4$)$_2$SO$_4$ sulphate (saturated) and resolved by sodium dodecyl sulfate-polyacrylamide gel electrophoresis (SDS-PAGE) (4% total acrylamide, 3% cross linker in tricene-HCl system) (Fekkes et al., 1998, *Mol Microbiol;* 29(5):1179-90). The gels were dried, and radioactive polypeptides detected with a phosphorimager (Molecular Imager FX, (BioRad). Data bands were quantitated with QuantityOne software (BioRad), and graphs were plotted with DeltaGraph (Red Rock software).

Cell culture. Blood stream form *T. brucei* CA427 was cultured in HMI-9 medium (Hirumi and Hirumi, 1994, *Parasitol Today;* 10:80-84) to a maximum density of $10^6$/ml. For use in drug sensitivity studies, cells were seeded at $10^{-4}$/ml, and one hundred microliters added to each well of a 96-well plate, with or without test compounds at stated concentrations, as discussed in Brief Descriptions of FIGS. 1-4. In controls, DMSO, the solvent for the compounds, was added. Cells were counted after 24 or 48 hours, using a hemocytometer, and the data graphed. All experiments were performed in triplicates.

HeLa cell line was maintained in RPMI-1640 supplemented with 10% bovine serum, 100 U/ml penicillin/streptomycin, and 2 mM L-glutamine at 37° C. in 5% $CO_2$.

HeLa cell viability assays. Propidium iodide exclusion assay (reviewed in Steff et al., 2001, *Cytometry*; 45(4):237-43 and Wigg et al., 2003, *Anal Biochem*; 317(1):19-25) was used to determine HeLa cell viability after drug treatment. Cells were plated at $1 \times 10^4$ cells per well (96 well plate) with or without addition of test compounds for the stated time periods, as described for FIGS. 1-4. Etoposide stock (2 mM in DMSO) was and diluted in RPMI 1640 to 100 µM immediately before use. Adherent cells were rinsed with phosphate buffered saline (PBS), trypsinized (37° C. for 5 minutes), pelleted (2,000 g, 2 minutes), resuspended in PBS (500 µl) containing propidium iodide (1 µg/ml), DAPI [4'-6-Diamidino-2-phenylindole] (5 µg/ml) and analyzed by flow cytometry on a Dakocytomation CyAn without gating. Single fluorophore controls were acquired prior to the collection of the experimental data.

Mitochondrial XTT reduction assays (Ranta et al., 1998, *J Cell Physiol*; 176(1):92-8 and Berridge et al., 2005, *Biotechnol Annu Rev*; 11:127-52) were performed as follows. HeLa cells were seeded in 96 well plates ($1 \times 10^4$ cells/well) (100 µl). At stated times, XTT dye (sodium 3,3-{1-[(phenylamino) carbonyl]-3,4-tetrazolium}-bis(4-methoxy-6-nitro) (25 µl of 1 mg/ml), and 5-methylphenzanium sulfate (25 µM, final concentration) were added to each well. Plates were incubated for two hours (37° C., 5% $CO_2$), and absorbance at 450 nm was read using a Versimax Tuneable Micro Plate Reader (Molecular Devices).

Results

*T. brucei* microsomes (TbRM) can import proteins post-translationally. Microsomes from canine pancreas are a model system used to study protein import into the ER of vertebrates and many other eukaryotes. However, ER signal sequences of *T. brucei* are not, in general, compatible with the protein import machinery of vertebrate ER (Al-Qahtani et al., 19998, Biochem J; 331:521-529 and Ramirez et al., 1999, *J Eukaryot Microbiol*; 46(6):557-65). Consequently, it was crucial, in order to study the biogenesis of trypanosome proteins such as $VSG\_117_{86}$, to develop a new protein import system using ER membranes from *T. brucei*. Two standard tests for successful microsomal ER protein import include proteinase (PK) protection of the translocated protein, and loss of protease protection after detergent permeabilization of microsomes (Connolly et al., 1989, *J Cell Biol*; 108(2):299-307). In the detergent permeabilization of microsomes test, detergent creates pores in the microsomal membranes that allow protease to access and digest imported proteins (Gelb et al., 2003, *Mol Biochem Parasitol*; 126(2):155-63).

A model trypanosome protein $VSG\_117_{86}$ was translated in rabbit reticulocyte lysate and cycloheximide was added to terminate protein synthesis. Subsequently, *T. brucei* microsomes (TbRM) was added, the mixture was incubated at 37° C. to facilitate protein import into TbRM, and reaction mixtures were (or were not) treated with proteinase K and/or detergent. See FIG. 1A for a flowchart of the experimental scheme. In the absence of TbRM, $VSG\_117_{86}$ was degraded by proteinase K (FIG. 1B, lane 2). TbRM protected $VSG\_117_{86}$ from proteinase K digestion (FIG. 1B, lane 4). Detergent permeabilization of TbRM resulted in proteinase K digestion of $VSG\_117_{86}$ (FIG. 1B, lane 5). From these data, it is concluded that $VSG\_117_{86}$ is imported post-translationally into TbRM. Signal peptide dependence of $VSG\_117_{86}$ translocation into TbRM was investigated. When the signal sequence was deleted from $VSG\_117_{86}$ the protein was not imported into TbRM.

From this example, it can be concluded that $VSG\_117_{86}$ is translocated into TbRM, a signal sequence is necessary for import of protein into TbRM, and import of $VSG\_117_{86}$ into TbRM occurs posttranslationally. Co-translational import of protein into TbRM could not be studied because the microsomes inhibit translation of protein.

A small molecule inhibitor of Hsp70-Hsp40 interaction blocks protein translocation into TbRM. Post-translational ER protein translocation in *Saccharomyces cerevisiae* and *E. coli* requires cytosolic chaperones. In the yeast *S. cerevisiae*, for example, Ssa1p (Hsp70) and co-chaperone Ydj1p (Hsp40) (Becker et al., 1996, *Mol Cell Biol*; 16(8):4378-86; Ngosuwan et al., 2003, *J Biol Chem*; 278(9):7034-42; and McClellan et al., 1998, *Mol Biol Cell*; 9(12): 3533-45) as well as Kar2p/BiP stimulate post-translational protein import (Lyman and Schekman, 1995, *J Cell Biol*; 131(5):1163-71; Panzner et al., 1995, *Cell*; 81(4):561-70; and Holkeri et al., 1998, *J Cell Sci*; 111:749-757). In *E. coli*, SecB and SecA chaperone protein secretion through the inner membrane (Zhou and Xu, 2003, *Nat Struct Biol*; 10(11):942-7; Ullers et al., 2004, *Proc Natl Acad Sci USA*; 101(20):7583-8; and Fekkes et al., 1998, *Mol Microbiol*; 29(5):1179-90), the topological equivalent of the eukaryote ER. Since protein import into *T. brucei* microsomes is post-translational the possibility that a trypanosome Hsp70 influenced protein translocation into TbRM was considered. Notably, the sequences of Ssa1p and a *T. brucei* cytosolic Hsp70 (Van der Ploeg et al., 1985, *Science*; 228(4706):1443-6) are 70% identical. To explore this concept, MAL3-101 was used as a small molecule inhibitor of Hsp40-mediated Hsp70 ATPase (Fewell et al., 2004, *J Biol Chem*; 279(49):51131-40) that inhibits import of prepro alpha-factor into microsomes from *S. cerevisiae*. *T. brucei* cytosol was pre-incubated with MAL3-101 (or an equal volume of DMSO), while VSG_117 mRNA was translated in a reticulocyte lysate. TbRM was then added post-translationally to the *T. brucei* cytosol-supplemented reticulocyte lysate, and after incubation, to promote import of protein into the microsomes, each mixture was treated with proteinase K. See FIG. 2A for flow chart of procedures.

In control reactions with DMSO in the reaction, TbRM imported 80% of $VSG\_117_{86}$, as measured by protection from proteinase K digestion (FIG. 2B, compare lanes 1, 2). In contrast, only 13% of $VSG\_117_{86}$ was translocated into TbRM when MAL3-101 was present (FIG. 2B, lanes 3, 4). In control experiments, MAL3-51 and MAL3-90 were examined. These data suggest that an Hsp70 family member is important for protein import into TbRM. More importantly, MAL3-101 is identified as a small molecule inhibitor of protein import into TbRM.

Equisetin and CJ-21,058 block protein translocation into TbRM. Post-translational protein secretion in *E. coli* is mediated by SecA (Watanabe and Blobel, 1993, *Proc Natl Acd Sci USA*; 90:9011-9015 and Knott and Robinson, 1994, *J Biol Chem*; 269(11):7843-6). CJ-21,058, isolated from the soil fungus CL47745, (Sugie et al., 2002, *J Antibiot (Tokyo)*; 55(1):25-9) is reported to inhibit of SecA. Speculating that CJ-21,058 might inhibit post-translational import of protein into TbRM, the effect of the compound was tested on $VSG\_117_{86}$ import into TbRM, following a protocol outlined in the description of FIG. 1A. CJ-21,058 (20 µM) inhibited translocation of VSG__117$_{86}$ into TbRM by 95% (FIG. 2B, compare lanes 7 and 8).

Equisetin, an analog of CJ-21,058, is produced by the soil fungus Fusarium heterosporum (Vesonder et al., 1979, *J Antibiot (Tokyo)*; 32(7):759-61). Since CJ-21,058 blocked protein translocation into TbRM, it was tested if equisetin had similar effects. Equisetin (25 µM) inhibited translocation of VSG__117$_{86}$ into TbRM by 95% (FIG. 2B, compare lanes 9 and 10). Hence, both CJ-21,058 and equisetin block VSG__117$_{86}$ translocation into TbRM.

TbRM protein translocation blockers (PTBs) are trypanocidal. Many important cell surface proteins in *T. brucei* enter the secretory pathway via the ER (Steverding et al., 1995, *J Cell Biol*; 131:1173-1182). Consequently, it is anticipated that preventing the movement of proteins into the ER would reduce the amount of cell surface proteins some of which perform vital physiological functions, and lead to parasite death. Therefore, compounds that blocked protein translocation into TbRM (such as protein translocation blockers (PTBs)) were tested for trypanocidal activity against cultured trypanosomes.

MAL3-101 killed *T. brucei* in dose-dependent fashion (FIG. 3A). Fifty percent of parasites were killed at 125 nM (IC$_{50}$), and one hundred percent of parasites were killed at 500 nM (IC$_{100}$). The related compound MAL3-51 lacked trypanocidal activity at concentrations as high as 5 mM (FIG. 3B). Similarly, MAL3-90 did not kill *T. brucei* at 3 mM.

Equisetin and CJ-21,058 exhibited anti-trypanosomal properties. Equisetin had an IC$_{50}$ of 3.3 µM (FIG. 3C). CJ-21,058 was also trypanocidal with an IC$_{50}$ of 7 µM (FIG. 3D). In control studies using two assays of human HeLa cell viability, the amount of drugs that killed all trypanosomes had no measurable effect on host cells (FIG. 4).

It is concluded that inhibition of import of protein into TbRM is associated with trypanocidal action. Thus, the in vitro protein import system of the present invention will be valuable for identifying compounds that can kill *T. brucei* blood stream form.

To obtain a sense of the effects of the newly discovered anti-trypanosome compounds on host (vertebrate) cells, the drugs were tested on human HeLa cells using concentrations that killed one hundred percent *T. brucei* (IC$_{100}$). No statistically significant differences were detected between drug-treated cells and control HeLa cells, using a cell viability assay based on propidium iodide exclusion (FIG. 4A). MAL3-101 (up to 10 mM) did not affect HeLa cell viability. Similarly, neither CJ-21,058 (20 µM) nor equisetin (26 µM) decreased viability of HeLa cells. In contrast, the positive control, etoposide, an inhibitor of topoisomerase II, produced significant cell death (FIG. 4A). Similar results were obtained with the XTT assay (FIG. 4B).

The data in FIGS. 1 to 4 are representative of many others performed that produced very similar results.

Discussion

Cell-free protein import into trypanosome ER membranes. An earlier study indicated that a signal peptide is important for secretion of a reporter protein in *T. brucei* (Bangs et al., 1996, *J Biol Chem*; 271:18387-18393). However, SRP is dispensable for protein entry into the secretory pathway (Liu et al., 2002, *J Biol Chem*; 277(49):47348-57), leading the authors of that study to propose the existence of an "alternative pathway" for protein entry into *T. brucei* ER. This example shows that *T. brucei* microsomes import proteins post-translationally (FIG. 1) in a signal sequence dependent manner. MAL3-101 an inhibitor of J-domain stimulated Hsp70 ATPase blocked import of VSG__117$_{86}$ into TbRM (FIG. 2), consistent with the likely participation of a *T. brucei* homolog of an Hsp70 (cytosolic or localized to the ER) in ER protein import.

The properties of protein import into TbRM are reminiscent of observations made with fingi microsomes. *S. cerevisiae* and *Candida maltosa* microsomes can import proteins post-translationally (Hansen et al., 1986, *Cell*; 45:397-406; Brodsky et al., 1995, *Proc Natl Acad Sci USA*; 92(21):9643-6; Brodsky et al., 1993, *J Cell Biol*; 120:95-102; and Wiedmann et al., 1988, *EMBO J*; 7(6):1763-8), and a soluble factor that stimulated import of alpha-mating factor into *S. cerevisiae* microsomes (Waters et al., 1986, *J Cell Biol*; 103(6 Pt 2): p. 2629-36) was identified as Hsp70 Ssa1p) (Ngosuwan et al., 2003, *J Biol Chem*; 278(9):7034-42; McClellan et al., 1998, *Mol Biol Cell*; 9(12):3533-45; and Chirico et al., 1988, *Nature*; 332(6167):805-10), which interacts specifically with the J-domain protein Hsp40 (Ydj1p) (Becker et al., 1996, *Mol Cell Biol*; 16(8):4378-86; McClellan et al., 1998, *Mol Biol Cell*; 9(12): 3533-45; and Cyr and Douglas, 1994, *J Biol Chem*; 269(13):9798-804). These data suggest that *T. brucei*, like the yeasts, can use a chaperone-dependent pathway for protein translocation into the ER.

Trypanosome secretory pathway as a target for drug discovery. Cell surface proteins, for example VSG (Pays and Nolan, 1998, *Mol. Biochem. Parasitol*; 91:3-36 and Sheader et al., 2005, *Proc Natl Acad Sci USA*; 102(24): 8716-21), transferrin receptors (Steverding et al., 1995, *J Cell Biol*; 131:1173-1182), nucleobase transporters, and GP63 (El-Sayed and Donelson, 1997, *J Biol Chem*; 272:26742-26748) are important for establishment and maintenance of trypanosomatid infections in humans. Movement of these proteins to the plasma membrane is dependent on initial entry into the parasite ER, following paradigms worked out in model eukaryotes (reviewed in Wickner and Schekman, 2005, *Science*; 310(5753):1452-6). The ER is a gateway for targeting of proteins to the Golgi, endosomes, lysosomes and plasma membrane.

Due to the large number of proteins that transit through the ER as part of their biogenesis, it seems plausible the small molecules that interfere with import of proteins into the ER of parasites may have potential as anti-parasite agents. Such inhibitors are likely to have pleiotropic effects on parasite viability by inhibiting the biogenesis of cell surface receptors, nutrient transporters, and protective surface proteins.

In vertebrates, protein import into the ER is co-translational and dependent on signal recognition particle (SRP) (Rapoport et al., 1996, *Annu Rev Biochem*; 65:271-303). In contrast, several protein in *T. brucei* are imported into the ER without SRP (Liu et al., 2002, *J Biol Chem*; 277(49):47348-57). Further, *T. brucei* VSG__117$_{86}$ and VSG MVAT7 can be imported into TbRM post-translationally (FIG. 1). Hence, both in vitro and in vivo data indicate that proteins can be imported into the ER of *T. brucei* post-translationally. In theory, mechanistic differences may exist between pathways used by vertebrate (hosts) and *T. brucei* to translocate proteins into the ER. If so, it is possible that compounds that interfere with post-translational ER protein import in *T. brucei* may compromise viability of the parasite without significant effect on vertebrate host cells, and become lead compounds for discovery of novel anti-trypanosome drugs. The complexity of the ER co-translational and post-translational protein translocation pathways (reviewed in Wickner and Schekman, 2005, *Science*; 310(5753): 1452-6) promises to offer multiple targets for drug discovery.

*T. brucei* ER protein translocation inhibitors (PTBs) are trypanocidal. Molecular chaperones (e.g., Hsp70, Kar2p (BiP), SecB, SecA) and co-chaperones (J-domain proteins Hsp40 and Sec63p) are important for post-translational protein import into the ER of eukaryotes, and for protein secretion in prokaryotes (for reviews see, Wickner and Schekman, 2005, *Science;* 310(5753):1452-6; Driessen et al., 2001, *Nat Struct Biol;* 8(6):492-8; and Mitra et al., 2006, *Nat Struct Mol Biol;* 13(11):957-64). The compound NSC 630668-R/1 (also called R/1) inhibits endogenous as well as Hsp40 stimulated Hsp70 activity (Fewell et al., 2004, *J Biol Chem;* 279(49): 51131-40). Further, R/1 also inhibits post-translational protein translocation into ER microsomes from *S. cerevesiae* (Fewell et al., 2004, *J Biol Chem;* 279(49):51131-40 and Fewell et al., 2001, *J Biol Chem;* 276(2):910-4). Using combinatorial chemistry approaches, analogs of R/1 have been produced, and designated as MAL3 series (Fewell et al., 2004, *J Biol Chem;* 279(49):51131-40). MAL3-101 and MAL3-39 inhibit Hsp40 mediated ATPase of Hsp70, and MAL3-101 inhibits post-translational translocation of α-mating factor into yeast microsomes (Fewell et al., 2004, *J Biol Chem;* 279(49):51131-40).

Figure 5:
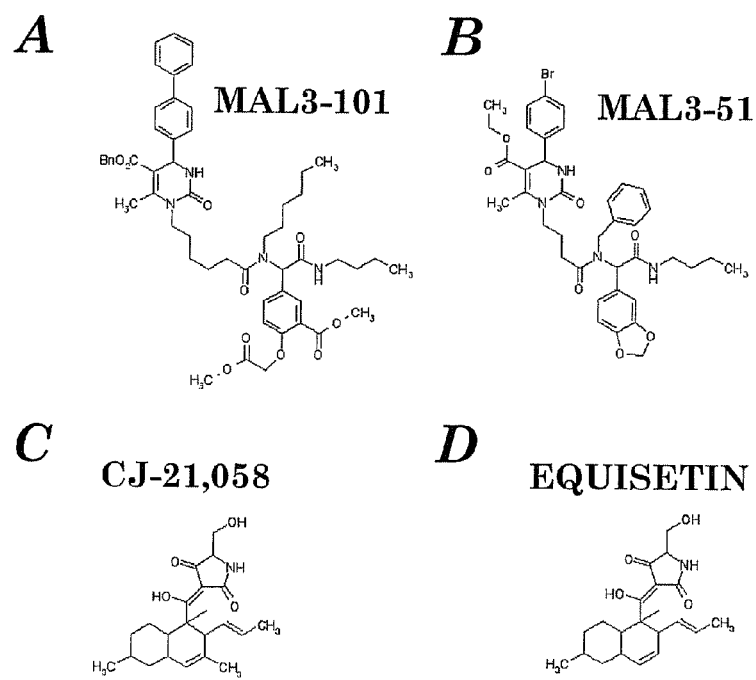
FIGS. 5A to 5D presents the chemical structures of MAL3-101, MAL3-51, CJ-21,058 and Equisetin.

This example studied the effect of small molecule modulators of Hsp70 on protein import into ThRM. MAL3-101 (structure shown in FIG. 5) blocked import of VSG_$117_{86}$ into TbRM (FIG. 2, lanes 3 and 4). Surprisingly, MAL3-51 and MAL3-90 that inhibit intrinsic Hsp70 ATPase activity (Fewell et al., 2004, *J Biol Chem;* 279(49):51131-40) do not inhibit protein translocation into TbRM. The difference in results between MAL3-51 (or MAL3-90) and MAL3-101 suggests that J-domain protein (e.g., Hsp40 or Sec63) modulation of Hsp70 (or Kar2p) contributes to translocation of protein into TbRM. Thus, *T. brucei* homologs of Hsp70/Hsp40 or Kar2p/Sec63p may be important for protein import into ThRM.

MAL3 compounds were tested for their effect on cultured *T. brucei*. MAL3-101 killed *T. brucei* at sub-micromolar level (FIG. 4A) and had undetectable effect on a mammalian cell line (FIG. 4A). The $IC_{50}$ of MAL3-101 is comparable to that of drugs currently to treat human African trypanosomiasis (HAT) ($IC_{50}$ of suramin is 1.4-2.3 µM, pentamidine is 0.3 nM) (del Rayo Camacho et al., 2002, *Phytother Res;* 16(5):432-6). MAL3-51 and MAL3-90 were not trypanocidal, even at millimolar concentrations, consistent with their inability to inhibit protein translocation into TbRM. These data suggest that MAL3-101 is a lead compound for anti-trypanosome drug discovery.

Equisetin and CJ-21,058 are natural products from the fungii *Fusarium heterosporum* (Vesonder et al., 1979, *J Antibiot (Tokyo);* 32(7):759-61), and CL47745 (Sugie et al., 2002, *J Antibiot (Tokyo);* 55(1):25-9), respectively. They are acyl tetramic acid derivatives (pyrrolidine-2,4-diones) (Burke et al., 2000, *Org Lett;* 2(23):3611-3) some of which have antibiotic or antiviral activities. Equisetin may be produced in large amounts, since it has been synthesized chemically (Burke et al., 2000, *Org Lett;* 2(23):3611-3).

Both equisetin and CJ-21,058 inhibit import of proteins into TbRM (FIG. 2), and both compounds are trypanocidal (FIG. 3), with little effect on human HeLa cells (FIG. 4). $IC_{50}$ of equisetin (3.3 µM) and CJ-21,058 (7 µM) is comparable to that of suramin that is used for treatment of HAT. Equisetin has been considered for treatment of HIV infection (reviewed in De Clercq, 2000, *Med Res Rev;* 20(5):323-49). Finally, the minimum concentration at which MAL3-101, equisetin, and CJ-21,058 exhibited trypanocidal effect ($IC_{100}$) was used to test their protein translocation blocking effect on TbRM. All compound inhibited protein translocation into TbRM at the concentration used. This example demonstrates that inhibition of protein import into the ER is a mode of the anti-trypanosomal action of these compounds in vivo. Thus, MAL3-101, equisetin, and CJ-21,058 are lead compounds for anti-trypanosome drug development.

Example 3

Role of Cytosol in Translocation

The present invention has developed, for the first time, a cell-free microsomal system for import of trypanosome proteins into the parasite ER. This example shows that cytosol from *T. brucei* is required for translocation of the full-length variant surface glycoproteins VSG_117 and VSG_MVAT7 into *T. brucei* microsomes (TbRM).

Trypanosome microsome preparation. Following procedures also described in Examples 1 and 2, *T. brucei* blood stream form were harvested from infected rat blood, washed in phosphate buffered saline, and resuspended ($2 \times 10^9$/ml) in homogenization buffer (50 mM HEPES-KOH, pH 7.5, 250 mM sucrose, 50 mM KOAc, 0.1 mM EDTA, 1 mM DTT). Each milliliter (ml) of parasites was lysed by Dounce homogenization, and cell lysis verified by microscopic examination. Lysates were centrifuged at 2,000-x g (10 minutes, 4° C.) to pellet nuclei and large aggregates. The supernatant from the first centrifugation was centrifuged at 12,000-x g (20 minutes, 4° C.), and the pellet saved as *T. brucei* rough microsomes (TbRM). The supernatant was centrifuged at 186,000-x g (4° C., 60 min) to obtain an 186,000 g-RM. All pellets were resuspended in rough microsome buffer (RMB) (at $OD_{280}$=50 per ml) and stored at −80° C. until use. One microliter (µl) of this TbRM preparation equals one equivalent of microsomes.

Preparation of cytosol from *T. brucei*. To obtain cytosol, the supernatant from preparation of the 186,000 g-RM described above was filtered and concentrated. Two ml of supernatant was placed in an ultrafiltration tube (Microcon-10; molecular weight cut-off, 10 kDa) (Amicon). The tube was centrifuged (3,000-xg, 4° C., 120 min), producing a 40 µl retentate, the cytosol preparation that was frozen in liquid nitrogen, and stored at −80° C.

Coding sequences for "cargo proteins" (for ER translocation) were cloned downstream of a (phage) T7 promoter. mRNAs were synthesized in vitro with the Ampliscribe T7 transcription kit (Epicenter), and concentrated as directed by the kit manufacturer. Rabbit reticulocyte lysate (Promega) was used to synthesize potential cargo proteins (e.g., VSG_117). [$^{35}$S]Methionine was added to the reticulocyte lysate, following vendor's instructions, in order to produce [$^{35}$S] Met-labeled protein that could be monitored easily by phosphorimager detection.

Import of trypanosome proteins. As detailed in Example 2, rough microsomes from *T. brucei* (TbRM) import a truncated form of VSG_$117_{86}$ (approximately 86 amino acids long (VSG86), termed mini-VSG)) synthesized in vitro. Protein import activity was associated with TbRM but not the 186, 000 g-RM. Signal peptide dependence of mini-VSG translocation into TbRM was investigated. When the signal sequence was deleted from mini-VSG the protein was not imported. ER translocation of mini-VSG only works with T brucei microsomes, but not canine microsomes. A signal sequence is necessary for import of protein into TbRM, and translocation of mini-VSG into TbRM is posttranslational because TbRM was introduced into the reaction mixture after cycloheximide, which inhibits protein synthesis in *T. brucei*, had been added.

Cytosol from *T. brucei* is required for the import of a 27-kDa Protein into TbRM. Encouraged by the successful import of mini-VSG into TbRM, it was next attempted to import longer versions of the protein. A 114-amino acid long VSG_117 (VSG_117$_{114}$) was imported efficiently but a substrate that was 260 amino acids long (VSG_117$_{260}$) could not be translocated into TbRM. Similarly, full-length VSG_117 was not imported into TbRM under these circumstances. These results were baffling, because all substrates contained the same signal sequence that facilitated import of mini-VSG into TbRM.

Since all the protein translocation studied occurred post-translationally, it was reasoned that a longer substrate might not translocate into TbRM because it may have adopted a conformation that was not "favorable" for import into the ER. In yeasts and *E. coli* that have posttranslational protein import systems, aggregated proteins can be "disentangled" by molecular "disaggregases" in the cytoplasm. Based on this information, it was suspected that cytosol from *T. brucei* might contain factors that could stimulate import of full-length VSG_117 into TbRM. To test this idea, cytosol was prepared from *T. brucei*, and used to supplement the in vitro system for translocation of VSG_MVAT7.

TbRM could not import full-length VSG_MVAT7 in the absence of cytosol. In the presence of cytosol, however, VSG_MVAT7 was protected from proteinase K. When detergent was added to permeabilize the microsomes prior to protease digestion, VSG_MVAT7 was degraded. Similar results were obtained with full-length VSG_117. Thus, it can be concluded that *T. brucei* cytosol contains a factor that is essential for posttranslational import of full-length VSG into TbRM.

Example 4

Small Molecule Inhibitors of In Vitro Protein Import onto the Trypanosome Endoplasmic Reticulum

*Trypanosoma brucei* causes human African trypanosomiasis (HAT), a disease against which new drugs are needed. To maintain an infection in vivo, T brucei relies on its cell surface proteins, including variant surface glycoproteins (VSGs). For VSG to be targeted to the exoplasmic side of the plasma membrane it must first translocate into the endoplasmic reticulum. Protein import into the ER is a good focus for the discovery of novel anti-trypanosome lead compounds. This example identifies compounds that inhibited protein translocation into ER microsomes, using an in vitro *T. brucei* microsomal system (TbRM) and a model VSG substrate (VSG-117$_{86}$). Post-translational import of VSG-117$_{86}$ into TbRM was inhibited by sodium azide, but not by valinomycin. Sodium azide is an inhibitor of F-type ATPases and SecA, thus an azide-sensitive chaperone is important for protein translocation into TbRM. The pyrmidinone-peptoid derivatives MAL3-101 and MAL3-51 inhibited post-translational import of VSG-117$_{86}$ into microsomes. Compounds of this class modulate Hsp70 ATPase activity, and thus MAL3-101 and MAL3-51 likely affect ER protein import by inhibiting Hsp70 interaction with VSG-117$_{86}$. Against cultured bloodstream T brucei, MAL3-101 was trypanocidal with an IG$_{50}$ of 1.5 μM; however, MAL3-51 did not kill the parasite. A cyclopeptolide, NFI028, inhibited import of VSG-117$_{86}$ into microsomes while a similar compound, CAM741, did not. Cyclopeptolides affect signal peptide recognition at the Sec61 translocon in a signal peptide-dependent manner. Thus, the signal peptide of VSG-117$_{86}$ is inhibited at the Sec61 translocon by NFI028, but not by CAM741. Both NFI028 and CAM741 were trypanocidal with IG$_{50}$'s of 1.5 μM and 2.0 μM, respectively. Therefore, MAL3-101, NFI028, and CAM741 are lead compounds for the discovery of pyrimidinone-peptoid and cyclopeptolide derivatives as new anti-trypanosome drugs.

Central to *T. brucei* survival in a vertebrate is variant surface glycoprotein (VSG). Proper VSG expression on the exoplasmic leaflet of the plasma membrane is crucial for *T. brucei* viability (Cross, 1975, *Parasitology;* 71(3):393-417; Sheader et al., 2005, *Proc Natl Acad Sci USA;* 102(24):8716-21; reviewed by Taylor and Rudenko, 2006, *Trends Genet;* 22(11):614-20). VSGs are delivered to the plasma membrane by way of the secretory pathway. The committed step for protein entry into the secretory pathway is translocation into the endoplasmic reticulum (reviewed by Shimizu and Hendershot, 2007, *Adv Exp Med Biol;* 594:37-46); a process directed by ER signal peptides. ER signal peptides occur at the N-terminus of secretory precursor proteins (reviewed by Izard and Kendall, 1994, *Mol Microbiol;* 13(5):765-73; and Hegde and Bernstein, 2006, *Trends Biochem Sci;* 31(10):563-71), and must be recognized by a Sec61 translocon complex at the ER membrane (Simon and Blobel, 1991, *Cell;* 65(3):371-80; Crowley et al., 1994, *Cell;* 78(3):461-71; and Jungnickel and Rapoport, 1995, *Cell;* 82(2):261-70).

Signal peptides can be targeted to the ER by two pathways. Co-translational import is an ER import pathway that occurs as translation of a polypeptide on the ribosome is ongoing; it depends on a signal recognition particle (SRP) and an SRP-receptor (SR) at the ER membrane. In an alternative pathway, post-translational import, protein translocation into the ER occurs after full translation of the secretory precursor in the cytoplasm; it does not depend on SRP. In *T. brucei*, protein import into the ER occurs both co-translationally and post-translationally (Liu et al., 2002, *J Biol Chem;* 277(49):47348-57; Lustig et al., 2007, *Eukaryot Cell;* 6(10):1865-75; and Goldshmidt et al., 2008, *J Biol Chem;* 283(46):32085-98). This example evaluated the effects of small molecule compounds on post-translational import of VSG-117$_{86}$ into *T. brucei* microsomes (TbRM).

Because Hsp70s in the cytoplasm and ER lumen are instrumental in protein translocation into the ER, compounds that inhibit their function could block VSG entry into the secretory pathway. Similarly, compounds that selectively inhibit *T. brucei* Sec61 translocon function could block VSG expression at the cell surface, and could be anti-trypanosome lead compounds.

The pyrimidinone-peptoid MAL3-101 (FIG. 6A) inhibits large T antigen (TAg, a J-domain containing protein) stimulation of Hsp70 ATPase activity, and inhibits post-translational translocation of pre-pro-alpha mating factor (pp MF) into *S. cerevisiae* microsomes (Fewell et al., 2004, *J Biol Chem;* 279(49):51131-40). With this example, the effects of MAL3-101 and a related compound, MAL3-51 (FIG. 6B) were tested on the post-translational import of VSG-117$_{86}$ into TbRM.

Cyclopeptolides CAM741 (FIG. 6C) and NFI028 (FIG. 6D) inhibit co-translational translocation of certain secretory proteins in a signal peptide-dependent fashion. Both CAM741 and NFI028 inhibit secretion of alkaline phosphatase possessing a signal peptide from vascular cell adhesion molecule 1 (VCAM1) by interfering with signal peptide binding to the Sec61 translocon (Besemer et al., 2005, *Nature;* 436(7048):290-3; Harant et al., 2006, *J Biol Chem;* 281(41):30492-502; and Harant et al., 2007, *Mol Pharmacol;* 71(6):1657-65). However, CAM741, but not NFI028, inhibited protein import directed by a vascular endothelial growth factor (VEGF) signal peptide. Because both CAM741 and NFI028 inhibit ER protein import with non-identical selectivity of signal peptides, both compounds were tested on VSG-117$_{86}$ import into TbRM.

Azide interferes with a variety of cellular processes across biological kingdoms. Growth of bloodstream *T. brucei* is inhibited by azide (IG$_{50}$ of 100 µM); however, it is not known how azide affects *T. brucei* (Steverding and Scory, 2004, *J Parasitol;* 90(5):1188-90). In *E. coli* and other prokaryotes, azide blocks protein translocation in vivo and in vitro by inhibiting the ATPase of SecA, a protein translocation chaperone (Oliver et al., 1990, *Proc Natl Acad Sci USA;* 87(21): 8227-31; van der Wolk et al., 1997, *EMBO J;* 16(24):7297-304; and reviewed by Schmidt and Kiser, 1999, *Microbes Infect;* 1(12):993-1004). Based on data showing *T. brucei* azide sensitivity and the ability of azide to inhibit post-translational protein translocation in prokaryotes, whether sodium azide affected post-translational translocation of VSG-117$_{86}$ into TbRM was tested.

This example identifies pyrimidinone-peptoids and cyclopeptolides as two classes of compounds that inhibit *T. brucei* ER protein import. Further, some of the compounds are trypanocidal. Therefore, pyrimidinone-peptoids and cyclopeptolides are lead compounds for discovery of new anti-trypanosomal compounds.

Materials and Methods

Materials. Taq DNA polymerase, amino acid mixture minus methionine and cysteine, and nuclease treated rabbit reticulocyte lysate were obtained from Promega (Madison, Wis.). dNTPs were obtained from Sigma (St. Louis, Mo.). DEPC-treated water was from USB Corporation (Cleveland, Ohio); QIAquick PCR purification kit was from Qiagen (Valencia, Calif.); Ampliscribe T7 in vitro transcription kit was from Epicentre (Madison, Wis.); TRAN35S—LABEL™ No-thaw metabolic labeling reagent was from MP Biomedicals (Solon, Ohio); cycloheximide was from Calbiochem (La Jolla, Calif.); proteinase K and leupeptin were from Roche (Indianapolis, Ind.); PMSF was from Boehringer Mannheim (Mannheim, Germany); ethanol and urea were from Fisher Scientific (Norcross, Ga.); Acrylagel and Bis-Acrylagel were from National Diagnostics (Atlanta, Ga.); TEMED and ammonium persulfate, were from Bio-Rad (Hercules, Calif.); DE52 was from Whatman (Hillsboro, Ohio); MAL3-101 and MAL3-51 were provided by Dr. Jeffrey L. Brodsky and Dr. Peter Wipf (University of Pittsburgh); AEE788, CAM741 and NFI028 were provided by Novartis (Vienna, Austria); sodium azide was from J. T. Baker (Phillipsburg, N.J.); valinomycin and all other chemicals and reagents were obtained from Sigma (St. Louis, Mo.).

Plasmids. VSG-117$_{86}$ DNA was made through PCR mutagenesis of a plasmid template, pVSG-117 (Innis et al., 1988, *Proc Natl Acad Sci USA;* 85(24):9436-40; Bangs et al., 1996, *J Biol Chem;* 271:18387-93).

Cell Strain and Isolation. Monomorphic *Trypanosoma brucei* strain 427 were grown in and purified from Sprague Dawley rats, using chromatography on DE52 (Cross 1975).

Primer Construction For VSG-117$_{86}$. PCR mutagenesis was used to create VSG-117$_{86}$ from the template pVSG-117 using variations of the forward primer TAATACGACT CAC-TATAGGG aggagggttt ttaccATGGA CTGCCATACA AAG-GAG (SEQ ID NO:22). Each primer contained a T7 promoter (upper case) and a translational enhancer (lower case) (Teilhet et al., 1998, *Gene;* 222(1):91-7). The coding region of VSG-117 starts at position 36 and ends at primer position 56 (upper case). The VSG-117 protein was truncated to 86 amino acids, using the reverse primer cgaacaacga aggggttcTT ATAGTGCGTA GATCGTAGCT TCGTTTC (SEQ ID NO:23), which has a stop codon (upper case) after the 27 nucleotides priming for nucleotides 295-321 (upper case) of the pVSG-117 sequence.

Generation of VSG-117$_{86}$ DNA. A VSG-117$_{86}$ PCR product was generated in a 100 µl reaction mixture containing 224 ng pVSG-117 template, 0.5 µM of each forward and reverse primer, Innis buffer (10 mM Tris-HCl pH 8, 2.5 µM MgCl$_2$, 0.05% Tween-20, 0.05% nonidet P-40, 50 mM KCl) (Innis et al., 1988, *Proc Natl Acad Sci USA;* 85(24):9436-40), 250 µM dNTPs, and 5 units of Taq DNA polymerase. The PCR reaction was carried out for 25 cycles as follows: 95° C. for 90 seconds, 56° C. for 90 seconds, and 74° C. for 2 minutes. The PCR product was purified using a QIAquick PCR purification kit (Qiagen). Purified PCR products were quantitated at 260 nm.

In Vitro Transcription. One µg of purified DNA was used as a template for transcription with an Ampliscribe™ T7 kit (Epicentre Technologies). One µl (1 MBU) of RNase free DNase I was added to the reaction (20 µl) and allowed to incubate at 37° C. for 15 minutes. The mixture was extracted with an equal volume of TE-saturated phenol/chloroform, and the aqueous phase extracted with chloroform. To the aqueous phase, sodium acetate (27 mM final concentration) was added along with 2.5 times the total volume of 100% ethanol. This mixture was allowed to precipitate at −20° C. overnight. The precipitate was recovered at 16,100×g at 4° C. for 15 minutes, rinsed with 70% ethanol, and pelleted at 16,100×g. The pellet was allowed to air dry, and resuspended in 40 µl of nuclease free water. The RNA concentration was determined by measuring the absorbance at 260 µm.

Microsome Preparation from Bloodstream *Trypanosoma brucei*. Bloodstream *T. brucei* lister 427 (1×10$^{10}$ cells/ml) were resuspended in 5 ml of fresh homogenization buffer (HB) (250 mM sucrose, 50 mM HEPES-KOH, 50 mM KOAc, 6 mM Mg(OAc)$_2$, 1 mM EDTA, 1 mM DTT, 1 µg/ml TLCK, 5 µg/ml leupeptin, 0.5 mM PMSF). In a clean, pre-chilled dounce homogenizer 2.5 ml of the resuspended cells were lysed on ice by 2 repetitions of 40 strokes with a tight-fitting pestle, with a one minute break after 40 strokes. The homogenates were pooled, aliquoted into microcentrifuge tubes (1 ml/tube), and centrifuged at 400×g for 10 minutes at 4° C. The supernatants from all tubes were pooled, aliquoted into a new microcentrifuge tube, and centrifuged at 13,400×g for 20 minutes at 4° C. The supernatants from the 13,400×g centrifugation step were recovered and pooled. Pellets from the 13,400×g centrifugation step were resuspended in 50 µl/pellet (total volume) of fresh rough microsome buffer (RMB) (250 mM sucrose, 50 mM HEPES-KOH, 50 mM KOAc, 1 mM DTT, 0.5 µg/ml TLCK, 2.5 µg/ml leupeptin). The microsome concentration was determined by measuring the absorbance at 260 nm, and the concentration was adjusted to an OD$_{260}$ of 50 (1 equivalent with an OD$_{260}$ of 50 µl). The microsomes were aliquoted into 20 µl portions, quick frozen in liquid nitrogen, and stored at −80° C. (Pellets from the 400×g centrifugation and the supernatant from the 13,400×g centrifugation were also saved).

Cytosol Preparation from Bloodstream *Trypanosoma brucei*. The supernatant saved from the 13,400×g centrifugation step (above) during the microsome preparation was centrifuged at 179,500×g at 4° C. for one hour in a Beckman Coulter Optima TLX ultracentrifuge. The supernatant was recovered, pooled (approximately 4 ml total), and concentrated using a Centricon-10 filter by centrifuging at 5000×g at 4° C. in 30 minute intervals until approximately 250 µl of concentrated cytosol remained. The cytosol was adjusted to an OD$_{280}$ of 50 (1 equivalent=50 OD units/µl), aliquoted, quick-frozen in liquid nitrogen, and stored at −80° C.

In Vitro Translation and Import of VSG Into *T. brucei* Microsomes (TbRM). RNA (250-500 ng) in DEPC-treated H$_2$O (7 µl) was incubated at 65° C. for three minutes. After cooling on ice for one minute, 1.5 µl (75 µM final concentration) of an amino acid mixture lacking methionine and cysteine (Promega), 1.5 µl of $^{35}$S-cysteine and methionine (2.5 mCi total activity, MP Biomedicals), 10 µl of rabbit reticulocyte lysate (Promega), and 1 µl of *T. brucei* cytosol was added to the RNA mixture, bringing the final volume to 21 µl. This reaction mixture was incubated at 37° C. for one hour. Translation was stopped with cycloheximide (1 mM final concentration).

The translation reaction was then divided into four separate portions of 5 µl each. Two of these portions were left untreated while the remaining two portions were supplemented with 1 µl (1 µl=1 equivalent, which has an OD$_{260}$ of 50) of TbRM. For inhibitor studies, one of the following was then added: MAL3-101 (10 µM final concentration), MAL3-51 (10 µM final concentration), CAM741 (1 µM final concentration), NFI028 (1 µM final concentration), sodium azide (8 µM final concentration), or AEE788 (8 µM final concentration). The four reaction aliquots were further incubated at 37° C. for 1.5 hours and then transferred to ice. Next, one of each sample (translation mixture with or without TbRM) was treated with a proteolysis mixture containing urea (3M) and proteinase K (0.5 mg/ml) (final concentrations) on ice for one hour. PMSF (34 mM final concentration) was added to quench the proteolysis reaction. Proteins were precipitated with 60% (NH$_4$)$_2$SO$_4$ on ice for 15 minutes, and centrifuged at 16,100×g at 4° C. for 7 minutes. The pellets were resuspended in 20 µl of 2.5×SDS sample buffer and resolved by SDS-PAGE in a Tris-Tricine gel system (16%—Resolving; 3%—Stacking) (reviewed by Gallagher, 2007 "One-dimensional SDS gel electrophoresis of proteins," Curr Protoc Cell Biol Chapter 6: Unit 6.1)). Radioactive polypeptides were detected with a phosphorimager; bands were quantitated with Quantity-One software (version 4.6.5, Bio-Rad).

Quantitation of Percent VSG Import. Using Quantity-One software (version 4.6.5, Bio-Rad), phosphorimages were adjusted so that gel bands corresponding to proteinase K-protected VSG-117$_{86}$ were visible. Next, background noise signals were subtracted using the "filter wizard" application. A Tiff image preserving these adjustments to the gel image was acquired. From this Tiff image, gel bands in each lane were quantitated by measuring the volume (counts*mm$^2$) of the band representing VSG-117$_{86}$. For background signal, the volume of an area in each lane of the gel image that best represented the average background pixel intensity was measured. In band and background intensity quantitation, the dimensions of the volume boxes were maintained. Next, a volume analysis report was performed to calculate the "adjusted volumes" (volume of VSG-117$_{86}$ band–volume of average background bands) of the VSG-117$_{86}$ bands. VSG import percentages were obtained as follows: the "adjusted volume" corresponding to a band detected in the presence of TbRM and challenged with proteinase K was divided by the "adjusted volume" corresponding to a band detected in the presence of TbRM without proteinase K. This quotient was multiplied by 100 to obtain a percentage of VSG import.

Cell Culture. Bloodstream *T. brucei* cell culture and drug susceptibility studies were performed as previously described. Bloodstream *T. brucei* CA427 were cultured in HMI-9 media (Hirumi and Hirumi, 1994, *Parasitol Today;* 10(2):80-4) to a density of 10$^6$ cells/ml. Cells were seeded (500 µl of 4×10$^4$ cells/ml) to a 24-well plate and exposed to MAL3-101, CAM741, and NFI028 at listed concentrations (see figure legends) or an equal volume of DMSO. Cells were incubated at 37° C. and counted after 24 and 48 hours, using a hemocytometer.

Results

MAL3-101 and MAL3-51 Inhibit Post-Translational Import of VSG-117 into *T. brucei* Microsomes. Cytosolic chaperones are essential for post-translational protein import into the ER (McClellan et al., 1998, *Mol Biol Cell;* 9(12): 3533-45; McClellan and Brodsky, 2000, *Genetics;* 156(2): 501-12; Ngosuwan et al., 2003, *J Biol Chem;* 278(9):7034-42; and Wickner and Schekinan, 2005, *Science;* 310(5753): 1452-6). Specifically, homologues of Hsp70 and its co-chaperone Hsp40 facilitate import in yeast by rendering secretory precursors "import competent" (Caplan et al., 1992, *Cell;* 71(7):1143-55; McClellan and Brodsky, 2000, *Genetics;* 156(2):501-12; Ngosuwan et al., 2003, *J Biol Chem;* 278(9):7034-42). MAL3-101 inhibits Hsp40 stimulation of Hsp70 ATPase, and inhibits post-translational translocation of pp MF into yeast microsomes (Fewell et al., 2004, *J Biol Chem;* 279(49):51131-40). In *T. brucei*, VSG can enter ER microsomes (TbRM) post-translationally. Since post-translational VSG translocation into ThRM may depend on cytosolic chaperones, the effects of MAL3-101 and MAL3-51 on import of the protein into TbRM were tested. As a model substrate we used VSG-117 that is truncated to 86 amino acids because unlike longer substrates it appears to have less stringent requirements for efficient import into TbRM.

Figure 7:
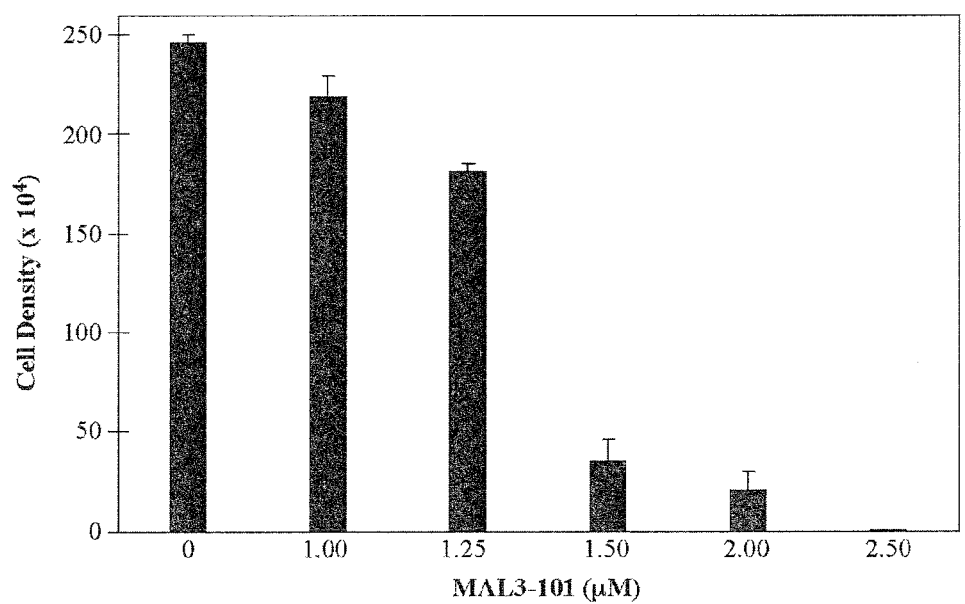
FIGS. 7A to 7C. MAL3-101 and MAL3-51 affect import of VSG-117$_{86}$ into *T. brucei* microsomes.

MAL3-101 (10 µM) reduced VSG-117$_{86}$ import into ThRM by 54% compared to a DMSO control (FIGS. 7A and 7B). Thus, MAL3-101 inhibits post-translational import of VSG-117$_{86}$ into TbRM. In *T. brucei*, cytosol is crucial for post-translational import of full-length VSG into ThRM. Therefore, the effect of *T. brucei* cytosol on VSG-117$_{86}$ import into TbRM in the presence of MAL3-101 was tested. *T. brucei* cytosol suppressed MAL3-101 inhibition of VSG-117$_{86}$ import into TbRM; 90% of VSG-117$_{86}$ was imported into TbRM in the presence of MAL3-101 (10 µM) (FIGS. 7A and 7B).

MAL3-51 (10 µM) also reduced import of VSG-117$_{86}$ into TbRM by 41% compared to the control (FIGS. 7A and 7B). However, *T. brucei* cytosol failed to rescue the MAL3-51 inhibition of VSG-117$_{86}$ import into TbRM; 45% of VSG-117$_{86}$ was imported into TbRM in the presence of MAL3-51 (10 µM) (FIGS. 7A and 7B).

This data demonstrates that the target of MAL3-101 is most likely a cytosolic protein (or factor); excess quantities of it from *T. brucei* cytosol bypass inhibition by the compound. On the other hand, excess amounts of the target of MAL3-51 are not present in cytosol from *T. brucei*.

The effects of MAL3-101 and MAL3-51 on VSG import into TbRM suggested that these compounds might inhibit translocation of other proteins in vivo, and compromise viability of *T. brucei*. Therefore, whether MAL3-101 and MAL3-51 were trypanocidal was tested. MAL3-101 inhibited cell growth (IG$_{50}$ of 1.5 µM), killing all parasites at 3 µM (FIG. 7C). However, MAL3-51 did not kill *T. brucei* at concentrations up to 500 µM.

NFI028 Inhibits VSG-117$_{86}$ Import into TbRM. CAM741 and NFI028 (FIGS. 6C and 6D) are cyclopeptolides, both of which inhibit mammalian co-translational protein import into the ER in a signal peptide-dependent fashion (Besemer et al., 2005, *Nature;* 436(7048):290-3; Harant et al., 2006, *J Biol Chem;* 281(41):30492-502; Harant et al., 2007, *Mol Pharmacol;* 71(6):1657-65). The effects of NFI028 and CAM741 on post-translational import have not been tested. In general however, *T. brucei* signal peptides are different from most mammalian signal peptides and are not translocated into canine microsomes (Al-Qahtani et al., 1998, *Biochem J;* 331: 521-9). Based on these facts, the effects of NFI028 and CAM741 on import of VSG-$117_{86}$ into TbRM was tested to evaluate their possible effects on *T. brucei* VSG-117.

NFI028 (1 μM) inhibited VSG-$117_{86}$ translocation into TbRM by 49%, compared to a DMSO control (FIGS. 8A and 8B). Higher concentrations of NFI028 (5 and 10 μM) inhibited VSG-$117_{86}$ import into TbRM to the same degree. In contrast, CAM741 (1 μM) did not affect import; VSG-$117_{86}$ import into TbRM was 73% and 74% in the presence of CAM741 or DMSO (solvent), respectively (FIGS. 8A and 8B). Similar results were obtained when import of VSG-$117_{86}$ into TbRM was tested with 10 μM CAM741.

NFI028 and CAM741 are Trypanocidal. Based on the observation that NFI028 inhibited post-translational import of VSG-$117_{86}$ into TbRM, it was determined if NFI028 was trypanocidal. If NFI028 inhibited ER protein import of VSG-$117_{86}$ in the present cell-free system it might also block translocation of other proteins in vivo. CAM741 was studied as a control compound. Upon exposure of bloodstream *T. brucei* to NFI028, the cells were killed ($IG_{50}$ of 1.5 μM) (FIG. 8C). Surprisingly, cells exposed to CAM741 were also killed with an $IG_{50}$ of 2 μM (FIG. 8D).

Sodium Azide Inhibits Post-Translational Import of VSG-$117_{86}$ into TbRM. Azide is a metabolic poison (Detimary et al., 1994, *Biochem J;* 297 (Pt 3):455-61; Van de Casteele et al., 2003, *Biochem Biophys Res Commun;* 312(4):937-44; Bowler et al., 2006, *Proc Natl Acad Sci USA;* 103(23):8646-9) that inhibits growth of bloodstream *T. brucei* (Steverding and Scory, 2004, *J Parasitol;* 90(5):1188-90). Azide inhibits F-type ATPases (Bowler et al., 2006, *Proc Natl Acad Sci USA;* 103(23):8646-9) and SecA, blocking protein secretion in prokaryotes (Oliver et al., 1990, *Proc Natl Acad Sci USA;* 87(21):8227-31; van der Wolk et al., 1997, *EMBO J;* 16(24): 7297-304; Miller et al., 2002, *Biochemistry;* 41(16):5325-32). To test the nature of (chaperone) ATPases that might influence post-translational translocation of VSG-$117_{86}$ into TbRM, the effects of azide and AEE788 were tested. AEE788 is an ATP mimic which inhibits kinase activities of endothelial growth factor receptor (EGFR) and vascular endothelial growth factor receptor (VEGFR) (Traxler et al., 2004, *Cancer Res;* 64(14):4931-41; Park et al., 2005, *Clin Cancer Res;* 11(5):1963-73; and Yazici et al., 2005, *Prostate;* 65(3):203-15).

When VSG-$117_{86}$ import into TbRM was tested in the presence of sodium azide (8 μM), post-translational import of the protein into TbRM was inhibited by 54% (FIGS. 9A and 9B). Similarly, VSG-$117_{86}$ import into TbRM was inhibited by 20% with 4 μM sodium azide. However, AEE788 (8 μM) failed to inhibit post-translational import of VSG-$117_{86}$ into TbRM (FIGS. 9A and 9B).

Next, it was determined if sodium azide was inhibiting ER protein import by acting on a membrane component of TbRM. This was accomplished by testing import of VSG-$117_{86}$ into TbRM that had been pre-treated with sodium azide (8 μM); TbRM pre-treated with NFI028 (1 μM) was used as a control. TbRM were treated with concentrations of sodium azide or NFI028 that were previously shown to inhibit ER protein import (FIGS. 9A-B and 8A-B, respectively). Addition of pre-treated microsomes to the reaction mixture reduced the effective concentrations of sodium azide and NFI028 from 8 μM and 1 μM to 1.4 μM and 0.2 μM, respectively. Protein import of VSG-$117_{86}$ into azide-treated microsomes was not inhibited (FIGS. 9C-D), suggesting that azide does not act on TbRM membranes. As a control, TbRM were pre-treated with NFI028 (1 μM) and tested for protein import. Import of VSG-$117_{86}$ into these NFI028-treated microsomes was inhibited by 10% (FIGS. 9C-D), indicating that, unlike sodium azide, NFI028 could act on TbRM membranes, or NFI028 inhibits protein import into TbRM when present at low concentrations in the reaction mixture.

Azide inhibits cytochrome c oxidase leading to a reduction of mitochondrial membrane potential, and blocks protein translocation into mitochondria (Bennett et al., 1992, *J Geriatr Psychiatry Neurol;* 5(2):93-101). However, bloodstream form *T. brucei* do not possess a functional mitochondria and lack cytochromes (Vickerman, 1985, *Br Med Bull;* 41(2): 105-14; Gull, 2002, *Curr Pharm Des;* 8(4):241-56; Steverding and Scory, 2004, *J Parasitol;* 90(5):1188-90). Therefore, azide is unlikely to reduce mitochondrial membrane potential in bloodstream *T. brucei*. Nevertheless, to ensure that the inhibitory effect of azide on VSG-$117_{86}$ import was occurring at ER-derived TbRM and not indirectly through inhibition of mitochondrial functions, the effect of valinomycin on VSG-$117_{86}$ post-translational import was tested. Valinomycin is a potassium ionophore that lowers membrane potential and inhibits mitochondrial protein import (at 0.5 μM) in *T. brucei* (Yermovsky-Kammerer and Hajduk, 1999, *Mol Cell Biol;* 19(9):6253-9; Priest and Hajduk, 2003, *J Biol Chem;* 278 (17):15084-94). The efficiency of VSG-$117_{86}$ import into TbRM was not affected by 0.5 μM valinomycin (FIGS. 9C-D), a concentration shown to inhibit mitochondrial protein import (Priest and Hajduk, 2003, *J Biol Chem;* 278(17): 15084-94).

This data demonstrate that sodium azide reduces post-translational import of VSG-$117_{86}$ into TbRM. However, azide does not have a direct effect on the *T. brucei* ER membrane.

Discussion

MAL3-101 and MAL3-51 Inhibit TbRM Protein Import But Only MAL3-101 Kills *T. brucei*. MAL3-101 inhibits Hsp40-stimulated Hsp70 activity (Fewell et al., 2004, *J Biol Chem;* 279(49):51131-40). In *T. brucei*, MAL3-101 inhibited post-translational VSG-$117_{86}$ import into TbRM (FIGS. 7A-B). However, cytosol from the parasite suppressed MAL3-101 inhibition of protein import (FIGS. 7A-B). *T. brucei* cytosol contains proteins that could function as chaperones necessary for post-translational protein import. Cytosol may reduce MAL3-101 inhibition for a variety of reasons: one possibility is that the addition of cytosol raised the concentration of Hsp40, excess amounts of which overcame the effect of the inhibitor. There is precedent for this phenomenon: MAL3-101 inhibition of T-antigen (TAg) stimulated Hsp70 ATPase activity could be suppressed with excess amounts of TAg (Fewell et al., 2004, *J Biol Chem;* 279(49): 51131-40).

MAL3-51 inhibited import of VSG-$117_{86}$ into TbRM in the absence of *T. brucei* cytosol, but unlike MAL3-101, cytosol did not block MAL3-51 effects on VSG-$117_{86}$ import into TbRM (FIGS. 7A-B), indicating that MAL3-51 and MAL3-101 inhibit post-translational protein import into TbRM by different mechanisms. First, MAL3-51 could inhibit Hsp70 chaperoning of VSG-$117_{86}$, but not by inhibiting Hsp40/Hsp70 ATPase stimulation. Second, MAL3-51 could interact with different types of Hsps than those bound by MAL3-101. As an example of such phenomenon, MAL3-101 inhibits TAg stimulation of Hsp70 ATPase, but does not inhibit Ydj1 (Hsp40) stimulation of Hsp70 ATPase activity (Fewell et al., 2004, *J Biol Chem;* 279(49):51131-40).

MAL3-101 is trypanocidal, inhibiting bloodstream *T. brucei* growth in vitro ($IG_{50}$ of 1.5 μM) (FIG. 7C). This data indicate that MAL3-101 can cross the plasma membrane of the parasite to exert its effects. Given the diverse roles of Hsp40/Hsp70 chaperones in vivo, this example indicates that MAL3-101 affects ER protein import as well as a variety of other cellular processes (such as, protein folding, protein import into the nucleus, protein import into glycosomes, signal transduction pathways) (reviewed in Brodsky and Chiosis, 2006, *Curr Top Med Chem;* 6(11):1215-25).

MAL3-51 did not kill bloodstream *T. brucei* cultured in vitro. When the structures of MAL3-101 and MAL3-51 are compared (FIGS. 6A-B), it is evident that the difference in abilities of MAL3-101 and MAL3-51 to inhibit protein import into TbRM and kill *T. brucei* may be a direct result of their structural differences. MAL3-101 possesses a pyrimidinone linked to a peptoid group by a hexylamino group (FIG. 6A, grey boxes) (Wright et al., 2008, *Bioorg Med Chem;* 16(6):3291-301). MAL3-51 has a peptoid group, but does not possess a pyrimidinone group (FIG. 6B) (Wright et al., 2008, *Bioorg Med Chem;* 16(6):3291-301). Also, the peptoid scaffolds of MAL3-101 and MAL3-51 have different substituents. Studies in mammalian tumor cells suggest that substituents off of the pyrimidinone group (R1) and peptoid group (R3) (FIG. 6A) are crucial for MAL3-10's ability to inhibit tumor growth (Wright et al., 2008, *Bioorg Med Chem;* 16(6): 3291-301). MAL3-51 does not have a pyrimidinone group as seen in MAL3-101, and thus lacks a chemical group at the R1 position (compare FIGS. 6A and 6B). Ultimately, these chemical differences may affect their cell permeability properties, causing MAL3-101 to be more effective than MAL3-51 in vivo (Wright et al., 2008, *Bioorg Med Chem;* 16(6): 3291-301).

Two Related Cyclopeptolides have Different Effects on VSG Import into TbRM. NFI028, but not CAM741, inhibited VSG-117$_{86}$ import into TbRM (FIGS. 8A-B). This example is the first demonstration that NFI028 inhibits signal peptide function in a post-translational system. In a mammalian system, CAM741 and NFI028 inhibit ER protein import of a select group of signal peptides (Besemer et al., 2005, *Nature;* 436(7048):290-3; Harant et al., 2006, *J Biol Chem;* 281(41): 30492-502; Harant et al., 2007, *Mol Pharmacol;* 71(6):1657-65). Specifically, CAM741 inhibits ER import of proteins whose signal peptides are relatively inefficient at directing import, and those with "helix-breaking" residues (glycine and proline) in their signal peptides. It is suggested that CAM741 prevents proper association of the signal peptide with the Sec61 translocon by binding directly to the signal peptide and/or by competitively associating with the signal peptide-binding site at the translocon (Harant et al., 2007, *Mol Pharmacol;* 71(6):1657-65).

Figure 6:
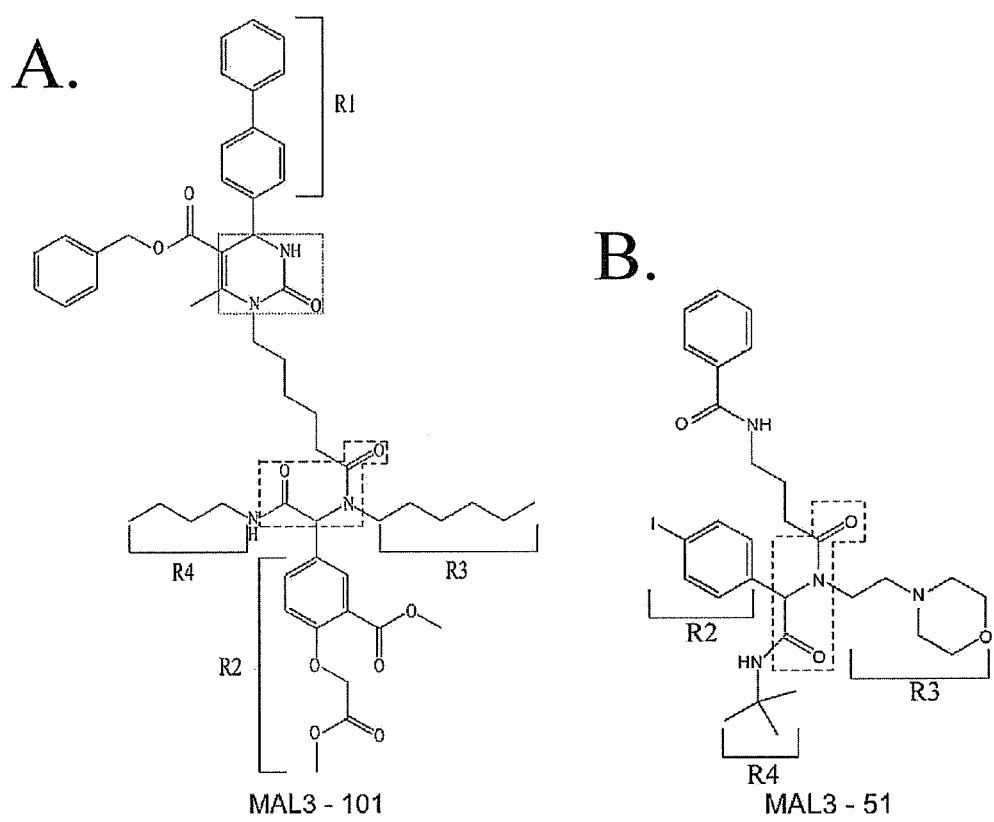
FIGS. 6A to 6D. Structures of MAL3-101, MAL3-51, CAM741, and NFI028. The chemical structures for MAL3-101 (FIG. 6A) and MAL3-51 (FIG. 6B) were reproduced from (Wright et al., 2008, *Bioorg Med Chem;* 16(6):3291-301), using ChemBioDraw Ultra (version 11.0.1 CambridgeSoft). The pyrimidinone group is highlighted by a box of dotted lines. The peptoid group is highlighted by a box of dashed lines, and substitutions (R1-R4) are marked by brackets. CAM741 (FIG. 6C) and NFI028 (FIG. 6D) chemical structures were reproduced from (Harant et al., 2007, *Mol Pharmacol;* 71(6):1657-65), using ChemBioDraw Ultra (version 11.0.1 CambridgeSoft). Different spatial orientations between CAM741 and NFI028 are highlighted by light grey boxes, and different chemical substituents are denoted by dark grey boxes.

Both NFI028 and CAM741 inhibited *T. brucei* growth, with similar IG$_{50}$ concentrations (1.5 μM and 2.0 μM, respectively) (FIGS. 8C-D). This data suggests that CAM741, along with NFI028, could inhibit other signal peptides in vivo thereby compromising viability of *T. brucei*. Also, the data indicates that CAM741 and NFI028 are transported into *T. brucei*, and thus are candidates for anti-trypanosome lead compounds. Furthermore, NFI028 and CAM741 have differences in their structures (FIGS. 6C-D, light grey box); NFI028 possesses a piperidine-1-carbaldehyde substitution while CAM741 is substituted with a propyl propionate group in that position (FIGS. 6C-D, dark grey box). These differences in structure produce unique effects on the VSG-117 signal peptide. CAM741 could inhibit other signal peptides in vivo, but not VSG-117. This indicates that derivatives of cyclopeptolides may posses anti-trypanosomal properties.

Azide Inhibits Post-Translational Import of VSG-117$_{86}$ Into TbRM. Post-translational import of VSG-117$_{86}$ into TbRM was inhibited by sodium azide (FIGS. 9A-B), but protein translocation was not inhibited when TbRM was pre-incubated with sodium azide (FIGS. 9C-D). AEE788, a competitive inhibitor of ATP for protein tyrosine kinases, had no effect on protein translocation (FIGS. 9A-B). These data indicated that azide did not inhibit all ATP-binding proteins, but blocked a select group of ATP-binding proteins. Further, valinomycin, an inhibitor of mitochondrial protein import, did not alter VSG-117$_{86}$ import into TbRM (FIGS. 9C-D) at a concentration shown to inhibit mitochondrial protein import, verifying that azide inhibited protein import at ER-derived membranes and not some mitochondrial contaminant of ThRM. These data demonstrate that azide inhibits a cytosolic chaperone that is important for VSG import into TbRM. Azide inhibits F-ATPases and SecA ATPase activity by forming a tight complex with bound-ADP in the ATPase catalytic site (Bowler et al., 2006, *Proc Natl Acad Sci USA;* 103(23): 8646-9), preventing the exchange of ADP for ATP. Since ATP hydrolysis is needed to drive SecA-dependent protein translocation, prokaryotic protein secretion is blocked in the presence of azide because the site of ATP hydrolysis is competitively inhibited by the ADP-azide complex (Oliver et al., 1990, *Proc Natl Acad Sci USA;* 87(21):8227-31; van der Wolk et al., 1997, *EMBO J;* 16(24):7297-304; Miller et al., 2002, *Biochemistry;* 41(16):5325-32; Bowler et al., 2006, *Proc Natl Acad Sci USA;* 103(23):8646-9). One possible explanation for azide sensitive ER protein import observed in *T. brucei* is that *T. brucei* could possess an azide-sensitive SecA-like cytosolic chaperone that is crucial for post-translational protein translocation into the ER. Alternatively, azide might inhibit chaperones with F-ATPase domains, halting protein translocation through the Sec61 channel in TbRM.

Protein translocation chaperones (e.g. Hsp40/Hsp70) and ER signal peptides are essential to post-translational protein import into the ER. Using a T brucei in vitro translocation system, this example has shown that protein translocation into TbRM can be blocked by small molecule inhibitors that target these components. The properties of these inhibitors will be further explored for the discovery of new anti-trypanosome lead compounds.

Example 5

Specificity of TbRM for Signal Peptides from Different Biological Families

Several studies have indicated that trypanosomatid signal peptides are not compatible with the translocon in vertebrates. However, *T. brucei* microsomes (TbRM) import proteins from the parasite, as expected. This example determined that the species-specificity of signal peptide utilization of canine microsomes is also exhibited by *T. brucei* microsomes. For this purpose, proteins from *E. coli* (β-lactamase), *S. cerevisiae* (prepro-alpha mating factor), *Bos taurus* (bovine) (preprolactin) and *Leishmania major* (gp63) were each translated in vitro and incubated with microsomes and cytosol from *T. brucei*. Translocation of the proteins into ThRM was tested with protease protection assays, as described in the previous examples.

Trypanosome TbRM could not protect proteins from the other species listed above from digestion by protease K. In control experiments, VSG_117 was protected from the protease under identical conditions. From these data, it can be concluded the TbRM is specific, in general, for signal peptides from T brucei. Failure of gp63 to enter TbRM was surprising since *L. major* is a trypanosomatid. However, the composition and design of *Leishmania major* signal peptides is similar to those from Gram-positive bacteria whereas *T.*

*brucei* signal sequences are not very similar in composition or organization of the subdomains to the prokaryote signal sequences.

Example 6

Defining Properties of *Trypanosoma brucei* Signal Peptides

Plasma membrane proteins are important for cellular communication and viability. Movement of proteins to the plasma membrane requires translocation into the endoplasmic reticulum (ER). An N-terminal signal sequence is required for import of proteins into the ER. In *T. brucei*, rudimentary properties of the ER protein translocation system have not been studied, despite the glaring importance of the pathway in the parasite. For instance, the essential features of signal peptides have not been defined. Although signal sequences had been thought to be interchangeable between species, in general, signal peptides from *T. brucei* are not functional with canine microsomes that are widely used to study mechanisms of ER protein import. ER signal peptides contain an h-region that is thought to be composed of random hydrophobic amino acids. Bioinformatic analyses reveal that h-regions of *T. brucei* contain conserved peptide patterns (motifs). Human h-regions contain motifs that are different from those in *T. brucei*.

The objective of this example is to provide a comprehensive account of the pathways and mechanisms of protein import into the ER of trypanosomes. Accomplishing this goal requires a study of both signal peptides and factors that are required for translocation of protein into TbRM. By comparing the properties of the trypanosome protein import pathway with those of mammalian host cells, new lead anti-trypanosome compounds will be identified.

In this example, *T. brucei* signal sequences will be studied. Specifically, this example will test whether peptide motifs that have discovered in h-regions (i.e., h-motifs) contribute to VSG translocation into the ER. The importance of specific amino acids (e.g., Leu and Val), order of residues, and hydrophobicity of the amino acids will be examined using both in vitro and in vivo approaches.

Two trypanosome proteins (VSG_117 and VSG_MVAT7) will be used to investigate the role of h-region motifs in the import of a native *T. brucei* protein into the ER. Motifs will be altered by site-directed mutagenesis to determine how h-region motifs affect signal peptide function. Then, h-motifs will be studied in context of a model peptide that will enable us to test whether or not *T. brucei* h-motifs are important for signal sequence activity in a trypanosome.

First, this example will determine if a single motif in a natural h-region is sufficient for protein import into the ER. Second, this example will explore whether the positioning of hydrophobic amino acids in a motif is sufficient for signal peptide activity, based on the observations that the all the fixed and ambiguous components in the *T. brucei* motifs are hydrophobic amino acids, although *T. brucei* signal sequences have many polar residues (e.g., Ser and Thr). It is predicted that any three hydrophobic residues (from the group Ala, Met, Cys, Phe, Leu, Val or Ile) could be substituted for the fixed and ambiguous components of the motif without diminishing biological activity of the signal peptide. Third, this example will investigate whether the order of amino acids in a motif is important for biological function. It is predicted that scrambling the h-motif sequence will either inhibit or abolish import of protein into the ER. Fourth, this example will evaluate the importance of h-motifs for variant surface glycoprotein (VSG_117) translocation into the ER in vivo.

Full-length VSG_117 containing the h-region mutants or the unmutated signal sequence will be tested for translocation into TbRM and the data quantitated. For each cargo substrate, the relative efficiency of VSG import into TbRM will be normalized to the activity of the unmutated VSG_117 h-region, in order to assess any inhibitory (or stimulatory) effects of the mutations on entry of VSG_117 into the ER. For a change in VSG import to be considered significant, the decrease in protein translocation must be greater than 50%.

H-regions containing various *T. brucei* h-motifs (singly, and in combinations found in the two native signal peptides VSG_117 and VSG_MVAT7) will be used to replace that of VSG_117, using megaprimer oligonucleotide-directed PCR mutagenesis and a cDNA encoding VSG_117 as template. RNA will be prepared using the purified PCR products as template for transcription, and used for translation/translocation with *T. brucei* microsomes. The proportion of protein imported into TbRM will be quantitated by comparing the residual radiolabeled substrate after protease K treatment with input (total) radiolabeled protein.

This example will determine how different motifs in h-regions of *T. brucei* alone, in multiple copies, or in different combinations contribute to signal peptide activity in *T. brucei*. It will also determine how the different h-motifs in two native signal peptides (VSG_117 and VSG_MVAT7) affect the ability of the proteins to enter the ER of a trypanosome.

Example 7

H-Motifs: The Importance of Hydrophobic Residues in ER Signal Peptides

Protein entry into the ER lumen depends on two components, Sec61 translocon at the ER membrane and a signal peptide (reviewed be Rapoport, 2007, *Nature;* 450(7170): 663-9). Protein translocation into the ER lumen can occur by two mechanisms. In mammals, secretory precursor proteins are brought to and translocated through the Sec61 translocon predominantly by a co-translational mechanism that requires a signal recognition particle (SRP) and its receptor (SR) (Walter and Blobel, 1981, *J Cell Biol;* 91(2 Pt 1):557-61; reviewed by Rapoport, 2007, *Nature;* 450(7170):663-9). In a second mechanism, termed post-translational translocation, protein import occurs after translation of the secretory precursor is completed in the cytoplasm. This mechanism involves the Sec71/72 and Sec62/63 complexes as well as the Sec61 translocon (reviewed by Matlack et al., 1998, *Cell;* 92(3):381-90; and Rapoport, 2007, *Nature;* 450(7170):663-9). Furthermore, cytosolic Hsp70 and Hsp40 chaperones are necessary for post-translational protein import into the ER (Caplan et al., 1992, *Cell;* 71(7):1143-55; Becker et al., 1996, *Mol Cell Biol;* 16(8):4378-86; McClellan and Brodsky, 2000, *Genetics;* 156(2):501-12; Ngosuwan, 2003, *J Biol Chem;* 278(9):7034-42; and reviewed by Rapoport, 2007, *Nature;* 450(7170):663-9). In both mechanisms, post-targeting recognition of a signal peptide at the Sec61 translocon is necessary for protein translocation into the ER (Jungnickel and Rapoport, 1995, *Cell;* 82(2):261-70). Recognition of signal peptides at the ER involves transmembrane segments TM2 and TM7 of Sec61 (Plath et al., 1998, *Cell;* 94(6):795-807; Van den Berg et al., 2004, *Nature;* 427(6969):36-44; and reviewed by Clemons et al., 2004, *Curr Opin Struct Biol;* 14(4):390-6).

An ER signal peptide has a charged n-region, an h-region composed of approximately 7-13 non-charged or hydrophobic amino acids, and a polar c-region (von Heijne, 1985, *J Mol Biol;* 184(1):99-105; Haeuptle et al., 1989, *J Cell Biol;* 108

(4):1227-36; and reviewed by Izard and Kendall, 1994, *Mol Microbiol;* 13(5):765-73; and Hegde and Bernstein, 2006, *Trends Biochem Sci;* 31(10):563-71). The hydrophobic core is necessary for signal peptide function (Kaiser et al., 1987, *Science;* 235(4786):312-7), and the peak hydrophobicity of this region is a major factor governing the ability and pathway by which a protein enters the ER (Chou and Kendall, 1990, *J Biol Chem;* 265(5):2873-80; Doud et al., 1993, *Biochemistry;* 32(5):1251-6; Ng et al., 1996, *J Cell Biol;* 134(2):269-78; and reviewed by Hegde and Bernstein 2006).

ER signal peptide h-regions lack sequence conservation (reviewed by Zheng and Gierasch, 1996, *Cell;* 86(6):849-52) and some have been replaced by apparently "random" hydrophobic sequences selected to promote protein import into the ER (Kaiser et al., 1987, *Science;* 235(4786):312-7). Nevertheless, several studies suggest that signal peptides of equivalent peak hydrophobicity can be species-specific (Abrahmsen et al., 1985, *EMBO J;* 4(13B):3901-6; Bird et al., 1987, *J Cell Biol;* 105(6 Pt 2):2905-14; Al-Qahtani et al., 1998, *Biochem J;* 331 (Pt 2):521-9; Zheng and Nicchitta, 1999, *J Biol Chem;* 274(51):36623-30), suggesting that h-region sequences may not be composed of random hydrophobic amino acids. For example, *E. coli* β-lactamase and *T. brucei* VSG-117 h-regions are strikingly similar in composition and peak hydrophobicity, yet *E. coli* β-lactamase is imported into canine microsomes (CfRM) whereas *T. brucei* VSG-117 is not translocated into CfRM (Al-Qahtani et al., 1998, *Biochem J;* 331 (Pt 2):521-9). Furthermore, h-region sequences are not truly random on a gross level because all of the possible hydrophobic amino acids are not equally represented (von Heijne, 1985, *J Mol Biol;* 184(1):99-105; von Heijne and Abrahmsen, 1989, *FEBS Lett;* 244(2):439-46). Different species have preference for specific amino acids in their h-regions; *Saccharomyces cerevisiae* shows preference for serine while *E. coli* favors alanine (von Heijne, 1981, *Eur J Biochem;* 116 (2):419-22; Nielsen et al., 1997, *Protein Eng;* 10(1):1-6). Finally, recent re-evaluation of h-regions from *E. coli, S. cerevisiae,* and humans has revealed that each species has a unique set of h-motifs in its signal peptides.

While it cannot be denied that high hydrophobicity contributes to translocation of signal peptides into the ER, this example demonstrates that peak hydrophobicity alone is not sufficient for signal peptide activity. Moreover, the arrangement of key amino acid residues (hydrophobic or polar) into motifs in an h-region (h-motifs) imparts physiological activity to a signal peptide.

Materials and Methods

Taq DNA polymerase, amino acid mixture minus methionine and cysteine, and nuclease treated rabbit reticulocyte lysate were obtained from Promega (Madison, Wis.). dNTPs were obtained from Sigma (St. Louis, Mo.). DEPC-treated water was from USB Corporation (Cleveland, Ohio); QIAquick PCR purification kit was from Qiagen (Valencia, Calif.); Ampliscribe T7 in vitro transcription kit was from Epicentre (Madison, Wis.); TRAN35S—LABEL™ No-thaw metabolic labeling reagent was from MP Biomedicals (Solon, Ohio); cycloheximide was from Calbiochem (La Jolla, Calif.); proteinase K and leupeptin were from Roche (Indianapolis, Ind.); PMSF was from Boehringer Mannheim (Mannheim, Germany); ethanol and urea were from Fisher (Norcross, Ga.); Acrylagel and Bis-Acrylagel were from National Diagnostics (Atlanta, Ga.); TEMED and ammonium persulfate were from Bio-Rad (Hercules, Calif.); DE52 was from Whatman (Hillsboro, Ohio). All other chemicals and reagents were obtained from Sigma (St. Louis, Mo.).

Plasmids. All VSG-117 mutants were made through PCR mutagenesis (Inis et al., 1988, *Proc Natl Acad Sci USA;* 85(24):9436-40) of a plasmid template, pVSG-117 (Bangs et al., 1996, *J Biol Chem;* 271(31):18387-93).

Cell Strain and Isolation. Monomorphic *Trypanosoma brucei* strain 427 were grown in and purified from Sprague Dawley rats, using chromatography on DE52 (Cross, 1975, *Parasitology;* 71(3):393-417).

Primer Construction For VSG-117 h-Region Mutants. PCR mutagenesis was used to create VSG-117 h-region mutants from the template, pVSG-117, using variations of the forward primer TAATACGACT CACTATAGGG aggagggttt ttaccATGGA CTGCCATACA AAGGAGACAC TGGGGT-CACA CAATGGAGGC GATCAACGAT GttcACACTA TCAttcttcT ActtcATCAC TCCAGCG (SEQ ID NO:3). Each primer contained a T7 promoter (upper case) and a translational enhancer (lower case) (Teilhet et al., 1998, *Gene;* 222 (1):91-7). The coding region of VSG-117 starts at position 36 and ends at primer position 83; it includes the n-region of VSG-117. This is followed by primer positions 84-128, which encodes for the h-region of the VSG-117 protein. All VSG-117 h-region mutants contained mutations within the forward primer as exemplified above in the $(Phe)_4$-VSG-$117_{86}$ mutant. All VSG-117 proteins were truncated to 86 amino acids, using the reverse primer cgaacaacga aggggttcTT ATAGTGCGTA GATCGTAGCT TCGTTTC (SEQ ID NO:4), which has a stop codon after the 27 nucleotides priming for nucleotides 295-321 of the pVSG-117 sequence.

Generation of VSG-117 Mutant DNA. VSG-117 PCR products were generated in 100 µl reactions mixtures containing 224 ng pVSG-117 template, 0.5 µM of each forward and reverse primer, Innis buffer (10 mM Tris-HCl pH 8, 2.5 mM $MgCl_2$, 0.05% Tween-20, 0.05% nonidet P-40, 50 mM KCl) (Innis et al., 1988, *Proc Natl Acad Sci USA;* 85(24):9436-40), 250 µM dNTPs, and 5 units of Taq DNA polymerase. PCR reactions were carried out for 25 cycles as follows: 95° C. for 90 seconds, 56° C. for 90 seconds, and 74° C. for 2 minutes. All PCR products were purified using a QIAquick PCR purification kit (Qiagen). Purified PCR products were quantitated at 260 nm.

In Vitro Transcription. One µg of purified DNA was used as a template for transcription with an Ampliscribe™ T7 kit (Epicentre Technologies). One µl (1 MBU) of RNase free DNase I was added to the reaction (20 µl) and allowed to incubate at 37° C. for 15 minutes. The mixture was extracted with an equal volume of TE-saturated phenol/chloroform, and the aqueous phase extracted with chloroform. To the aqueous phase, sodium acetate (27 mM final concentration) was added along with 2.5 times the total volume of 100% ethanol. This mixture was allowed to precipitate at −20° C. overnight. The precipitate was recovered at 16,100×g at 4° C. for 15 minutes, rinsed with 70% ethanol, and pelleted at 16,100×g. The pellet was allowed to air dry, and resuspended in 40 µl of nuclease free water. The RNA concentration was determined by measuring the absorbance at 260 nm.

Microsome Preparation from Bloodstream Form *Trypanosoma brucei.* Bloodstream form *T. brucei* lister 427 ($1 \times 10^{10}$ cells/ml) were resuspended in 5 ml of fresh homogenization buffer (HB) (250 mM sucrose, 50 mM HEPES-KOH, 50 mM KOAc, 6 mM $Mg(OAc)_2$, 1 mM EDTA, 1 mM DTT, 1 µg/ml TLCK, 5 µg/ml leupeptin, 0.5 mM PMSF). In a clean, prechilled dounce homogenizer 2.5 ml of the resuspended cells were lysed on ice by 2 repetitions of 40 strokes with a tight-fitting pestle, with a one minute break after 40 strokes. The homogenates were pooled, aliquoted into microcentrifuge tubes (1 ml/tube), and centrifuged at 400×g for 10 minutes at 4° C. The supernatants from all tubes were pooled, aliquoted into a new microcentrifuge tube, and centrifuged at 13,400×g for 20 minutes at 4° C. The supernatants from the 13,400×g centrifugation step were recovered and pooled. Pellets from the 13,400×g centrifugation step were resuspended in 50 µl/pellet (total volume) of fresh rough microsome buffer (RMB) (250 mM sucrose, 50 mM HEPES-KOH, 50 mM KOAc, 1 mM DTT, 0.5 µg/ml TLCK, 2.5 µg/ml leupeptin). The microsome concentration was determined by measuring the absorbance at 260 nm, and the concentration was adjusted to an $OD_{260}$ of 50 (1 equivalent=$OD_{260}$ of 50=1 µl). The microsomes were aliquoted into 20 µl portions, quick frozen in liquid nitrogen, and stored at −80° C. (pellets from the 400×g centrifugation and the supernatant from the 13,400×g centrifugation were also saved).

In Vitro Translation and Import of VSG Into *T. brucei* Microsomes (TbRM). RNA (250-500 ng) in DEPC-treated $H_2O$ (7 µl) was incubated at 65° C. for three minutes. After cooling on ice for one minute, 1.5 µl (75 µM final concentration) of an amino acid mixture lacking methionine and cysteine (Promega), 1.5 µl of $^{35}S$-cysteine and methionine (2.5 mCi total activity, MP Biomedicals), and 10 µl of rabbit reticulocyte lysate (Promega) was added to the RNA mixture, bringing the final volume to 20 µl. This reaction mixture was incubated at 37° C. for 1 hour. Translation was stopped with cycloheximide (1 mM final concentration).

The translation reaction was then divided into four separate portions of 5 µl each. Two of these portions were left untreated while the remaining two portions were supplemented with 1 µl (1 µl=1 equivalent, which has an $OD_{260}$ of 50) of TbRM. The four reaction aliquots were further incubated at 37° C. for 1.5 hours and then transferred to ice. Next, one of each sample (translation mixture with or without TbRM) was treated with a proteolysis mixture containing urea (3M) and proteinase K (0.5 mg/ml) (final concentrations) on ice for 1 hour. PMSF (34 mM final concentration) was added to quench the proteolysis reaction. Proteins were precipitated with 60% $(NH_4)_2SO_4$ on ice for 15 minutes, and centrifuged at 16,100×g at 4° C. for 7 minutes. The pellets were resuspended in 20 µl of 2.5×SDS sample buffer and resolved by SDS-PAGE in a Tris-Tricine gel system (16%—Resolving; 3%—Stacking) (as reviewed by Gallagher, 2007, "One-dimensional SDS gel electrophoresis of proteins." Curr Protoc Cell Biol Chapter 6). Radioactive polypeptides were detected with a phosphorimager; bands were quantitated with Quantity-One software (version 4.6.5, Bio-Rad).

Quantitation of Percent VSG Import. Using Quantity-One software (version 4.6.5, Bio-Rad), phosphorimages were adjusted so that gel bands corresponding to proteinase K-protected VSG-$117_{86}$ were visible. Next, background noise signals were subtracted using the "filter wizard" application. A Tiff image preserving these adjustments to the gel image was acquired. From this Tiff image, gel bands in each lane were quantitated by measuring the volume (counts*$mm_2$) of the band representing VSG-$117_{86}$. For background signal, the volume of an area in each lane of the gel image that best represented the average background pixel intensity was measured. In band and background intensity quantitation, the dimensions of the volume boxes were maintained. Next, a volume analysis report was performed to calculate the "adjusted volumes" (volume of VSG-$117_{86}$ band–volume of average background bands) of the VSG-$117_{86}$ bands. VSG import percentages were obtained as follows: the "adjusted volume" corresponding to a band detected in the presence of TbRM and challenged with proteinase K was divided by the "adjusted volume" corresponding to a band detected in the presence of TbRM without proteinase K. This quotient was multiplied by 100 to obtain a percentage of VSG import.

Results

Factors Other Than h-Region Peak Hydrophobicity May Govern Protein Import into ER Microsomes. The hydrophobic core (h-region) of a signal peptide is necessary for protein import into the ER (as reviewed by Hegde and Bernstein, 2006, *Trends Biochem Sci;* 31 (10):563-71). Surprisingly, h-region sequences are not conserved. It has been suggested that an h-region is composed of random hydrophobic amino acids, and that the overall hydrophobic nature of this region governs signal peptide activity. However, not all h-regions of similar hydrophobicity are equivalent in function (reviewed by Zheng and Gierasch, 1996, *Cell;* 86(6):849-52; and Hegde and Bernstein, 2006, *Trends Biochem Sci;* 31(10):563-71). Therefore, this example revisited the role of h-region hydrophobicity in protein import into the ER with the hope of offering new perspectives. With this example, the role of h-region hydrophobicity in ER protein import in *T. brucei* was evaluated using a truncated VSG-117 substrate (86 amino acids long) and a *T. brucei* cell-free translocation system. VSG-117 is imported into TbRM, but it is not imported into canine microsomes, although VSG-117 possesses similar h-region hydrophobicity as other proteins that are imported into canine microsomes. From this, the hypothesis was formed that h-region characteristics other than hydrophobicity may be responsible for ER protein import, and we sought to determine how an h-region directs import of VSG-117 into TbRM. To examine the importance of h-region hydrophobicity in ER protein import, h-region mutants were created from VSG-117 (VSG-$117_h$) where residues 4, 8, 9, and 11 were simultaneously mutated from $Leu_4$, $Leu_8$, $Leu_9$, $Ala_{11}$ to $Gly_4$, $Gly_8$, $Gly_9$, $Gly_{11}$ or $Ser_4$, $Ser_8$, $Ser_9$, $Ser_{11}$, creating the mutants $(Gly)_4$-VSG-$117_h$ and $(Ser)_4$-VSG-$117_h$, respectively (Table 1). Unmutated VSG-$117_h$ (VSG-$117_h$) contains seven hydrophobic amino acids (Table 1), and by mutating four of these hydrophobic amino acids to the non-hydrophobic amino acids glycine or serine the peak hydrophobicity was reduced by approximately 75% from 2.08 to 0.43 or 0.30, respectively (FIG. 10B). Because of the drop in peak hydrophobicity, VSG import into TbRM was expected to decrease in both $(Gly)_4$-VSG-$117_{86}$ and $(Ser)_4$-VSG-$117_{86}$-Curiously, while only 8% of $(Gly)_4$-VSG-$117_{86}$ was imported into TbRM, 44% of $(Ser)_4$-VSG-$117_{86}$ was imported into TbRM (FIGS. 10A (panels A-C) and 10B).

TABLE 1

| VSG | Position of Amino Acids in h-region Sequence | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| VSG-$117_h$ | S | T | M | L | T | L | S | L | L | Y | A | I | T | P |
| $(Gly)_4$-VSG-$117_h$ | S | T | M | G | T | L | S | G | G | Y | G | I | T | P |
| $(Ser)_4$-VSG-$117_h$ | S | T | M | S | T | L | S | S | S | Y | S | I | T | P |
| $(Ala)_7$-VSG-$117_h$ | S | T | A | A | T | A | S | A | A | Y | A | A | T | P |
| $(Ala)_6$-Ile12-VSG-$117_h$ | S | T | A | A | T | A | S | A | A | Y | A | I | T | P |
| $(Ala)_4$-VSG-$117_h$ | S | T | M | A | T | L | S | A | A | Y | A | I | T | P |

Amino Acid Sequences of VSG-$117_h$, $(Gly)_4$-VSG-$117_h$, $(Ser)_4$-VSG-$117_h$, $(Ala)_7$-VSG-$117_h$, $(Ala)_6$-Ile12-VSG-$117_h$, and $(Ala)_4$-VSG-$117_h$.
The h-Region sequences of VSG-$117_h$ (SEQ ID NO:5), $(Gly)_4$-VSG-$117_h$ (SEQ ID NO:6), $(Ser)_4$-VSG-$117_h$ (SEQ ID NO:7), $(Ala)_7$-VSG-$117_h$ (SEQ ID NO:8), $(Ala)_6$-Ile12-VSG-$117_h$ (SEQ ID NO:9), and $(Ala)_4$-VSG-$117_h$ (SEQ ID NO:10) are aligned.
Position 1 denotes the beginning of the h-region and position 14 marks its end.
Mutations to VSG-$117_h$ are listed in bold.

To test whether or not import of (Ser)$_4$-VSG-117$_{86}$ into TbRM was an anomaly, a new h-region mutant was created by mutating all seven hydrophobic amino acids in the VSG-117 h-region to alanine (i.e. seven alanine residues at positions 3, 4, 6, 8, 9, 11, & 12), creating (Ala)$_7$-VSG-117$_h$ (Table 1). (Ala)$_7$-VSG-117$_h$ has a peak hydrophobicity more than twice that of (Ser)$_4$-VSG-117$_h$ (FIG. 10B), and was predicted to be imported into TbRM with greater efficiency than the former signal peptide. Surprisingly, (Ala)$_7$-VSG-117$_{86}$ was not imported into TbRM (1%) (FIG. 10A (panel "D") and FIG. 10B). This data is reminiscent of studies of E. coli signal peptides; a model h-region comprised of polyalanine is non-functional (Doud et al., 1993, Biochemistry; 32(5):1251-6). However, activity was restored to this polyalanine signal peptide when more hydrophobic amino acids were introduced into the peptide. Using these data as precedent, amino acids at positions (1) 12 or (ii) 3, 6, and 12 from VSG-117$_h$ were introduced back into (Ala)$_7$-VSG-117$_h$, making the new h-region mutants (Ala)$_6$-Ile$_{12}$-VSG-117$_h$ or (Ala)$_4$-VSG-117$_h$, respectively (Table 1). Changing Ala$_{12}$ in (Ala)$_7$-VSG-117$_h$ to Ile$_{12}$ in (Ala)$_6$-Ile$_{12}$-VSG-117$_h$ raised the hydrophobicity from 0.89 in (Ala)$_7$-VSG-117$_h$ to 1.21 in (Ala)$_6$-Ile$_{12}$-VSG-117$_h$. Likewise, mutating Ala$_3$, Ala$_6$, and Ala$_{12}$ in (Ala)$_7$-VSG-117$_h$ to Leu$_3$, Leu$_6$, and Ile$_{12}$ in (Ala)$_4$-VSG-117$_h$ increased the hydrophobicity from 0.89 in (Ala)$_7$-VSG-117$_h$ to 1.41 in (Ala)$_4$-VSG-117$_h$ (FIG. 10B). Interestingly, 18% of (Ala)$_6$-Ile$_{12}$-VSG-117$_{86}$ was imported into TbRM while 82% of (Ala)$_4$-VSG-117$_{86}$ was translocated into TbRM (FIG. 10A (panels "E" and "F") and FIG. 10B).

The data from translocation of (Gly)$_4$-VSG-117$_{86}$, (Ser)$_4$-VSG-117$_{86}$, (Ala)$_7$-VSG-117$_{86}$, (Ala)$_6$-Ile$_{12}$-VSG-117$_{86}$, and (Ala)$_4$-VSG-117$_{86}$ showed that as peak hydrophobicity increases VSG import into TbRM did not increase correspondingly (FIG. 10B). In fact, only (Ser)$_4$-VSG-117$_{86}$ and (Ala)$_4$-VSG-117$_{86}$ were imported into TbRM in significant amounts (44% and 82% respectively). The inability of (Gly)$_4$-VSG-117$_{86}$, (Ala)$_7$-VSG-117$_{86}$, and (Ala)$_6$-Ile$_{12}$-VSG-117$_{86}$ to be imported into TbRM convincingly (FIG. 10A (panels "B," "D," and "E") and FIG. 10B) seems to be at odds with data suggesting that increases in h-region hydrophobicity increases ER protein import efficiency. (Gly)$_4$-VSG-117$_{86}$, (Ala)$_7$-VSG-117$_{86}$, and (Ala)$_6$-Ile$_{12}$-VSG-117$_{86}$ all have h-region hydrophobicity values higher than that of (Ser)$_4$-VSG-117$_{86}$ (0.43, 0.89, and 1.21 vs. 0.3, respectively) (FIG. 10B). One would expect that h-regions with hydrophobicity values greater than 0.3 would be imported into TbRM; however, this was not observed. These data show how h-region hydrophobicity fails to predict the biological activity of a signal peptide, and do not support the idea that peak hydrophobicity is the major factor governing protein import into TbRM. Consequently, two factors that had potential to be responsible for VSG import into microsomes were investigated; kinetics of protein translocation into the ER, and arrangement of amino acids within the h-region.

Kinetics of VSG-117$_{86}$ and (Ala)$_4$-VSG-117$_{86}$ Import into ThRM. How hydrophobicity of VSG-117$_{86}$ (2.08 hydrophobicity units, FIG. 10B) and (Ala)$_4$-VSG-117$_{86}$ (1.41 hydrophobicity units, FIG. 10B) affected import of VSG into ThRM was investigated by evaluating the rate and extent of translocation of the two signal peptides.

Figure 11:
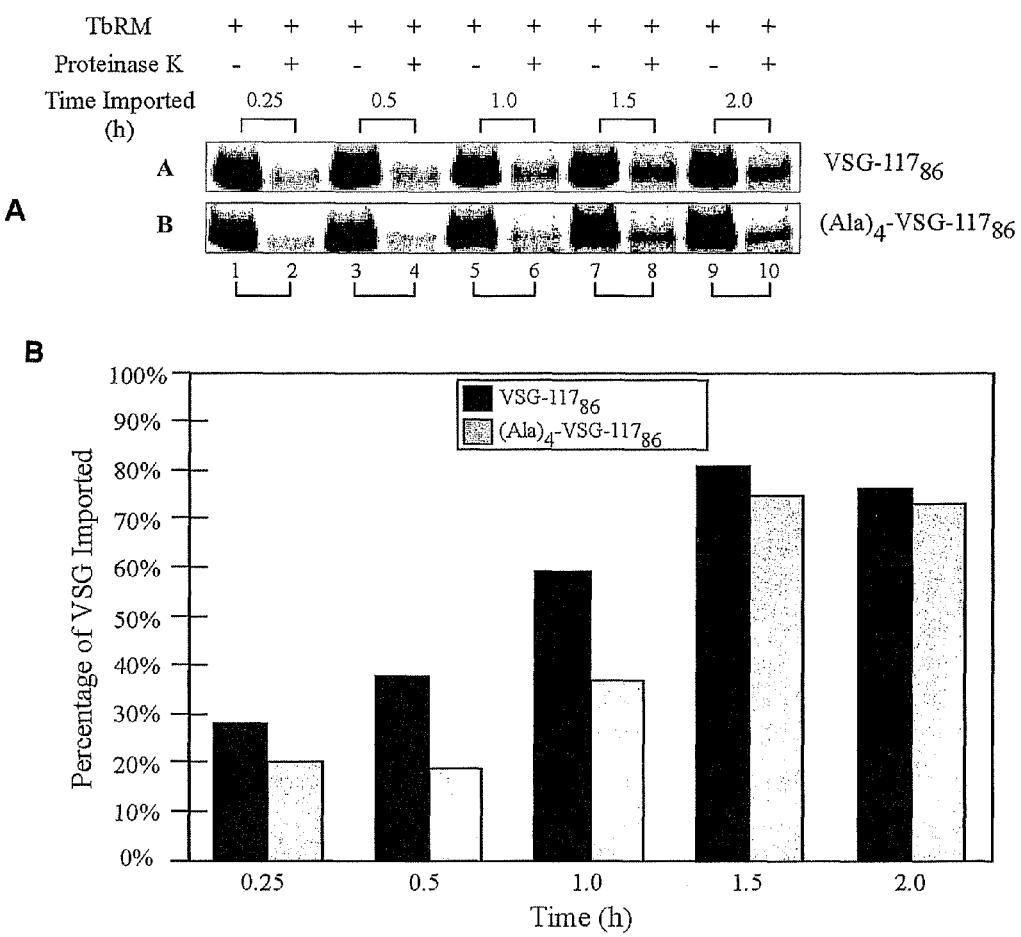
FIGS. 11A and 11B present translocation time courses of VSG-117$_{86}$ and (Ala)$_4$-VSG-117$_{86}$ into *T. brucei* microsomes.
Figure 16:
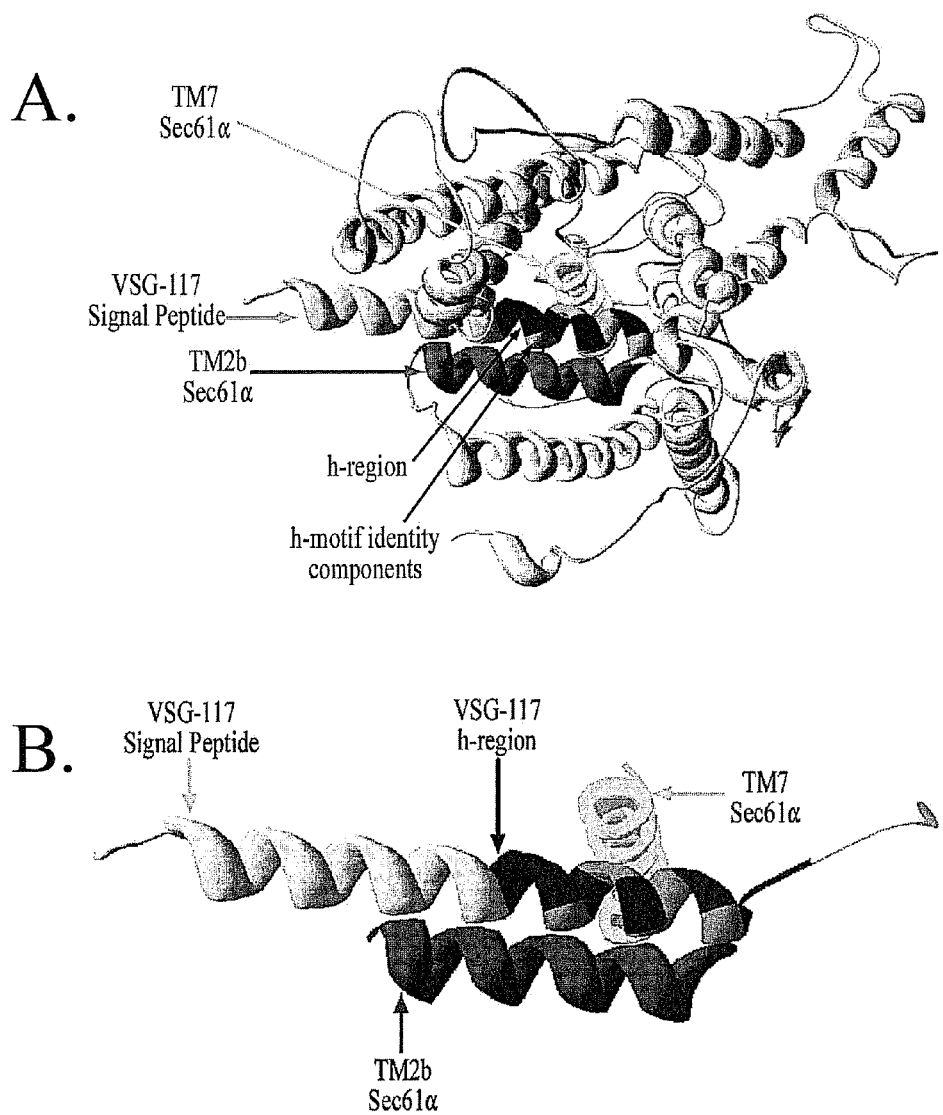
FIGS. 16A to 16D present models for Sec61 and signal peptide h-region interactions.

A time-course of VSG import into TbRM showed that (Ala)$_4$-VSG-117$_{86}$ is translocated into TbRM at a slower rate than VSG-117$_{86}$. Whereas half of the total amount of VSG-117$_{86}$ is imported into TbRM within approximately 0.5 h (FIG. 11A (panel "A") and FIG. 11B), it took one hour for half of the total amount of (Ala)$_4$-VSG-117$_{86}$ to be imported into ThRM (FIG. 11A (panel "B") and FIG. 11B). However, both VSG-117$_{86}$ and (Ala)$_4$-VSG-117$_{86}$ achieve maximum accumulation at 1.5 hours (81% and 75%, respectively) (FIG. 11A (panels "A" and "B") and FIG. 11B). This data supports a hydrophobicity difference of 0.67 (approximately 30%) between the h-regions of VSG-117$_{86}$ and (Ala)$_4$-VSG-117$_{86}$ affected the rate of VSG import up to the 60 minute time-point. At 90 minutes and beyond, only differences in extent of VSG import into TbRM are discernable. Therefore, any reduction in import of a VSG-117 h-region mutant at the 90-minute time-point is not a consequence of slower import kinetics.

Arrangement of Amino Acids in h-Region Affects VSG Import into TbRM. If peak hydrophobicity could not explain the failure to import (Gly)$_4$-VSG-117$_{86}$, (Ala)$_7$-VSG-117$_{86}$, and (Ala)$_6$-Ile$_{12}$-VSG-117$_{86}$ into TbRM (FIG. 10A (panels "B," "D," and "E") and FIG. 10B), what h-region characteristics influenced the process? One hypothesis to explain these data is that the arrangement of h-region amino acids is important for signal peptide activity. To test this hypothesis, new VSG-117 h-regions were designed by scrambling the sequences of (Ala)$_4$-VSG-117$_h$ and (Ser)$_4$-VSG-117$_h$, producing "scrambled (Ala)$_4$-VSG-117$_h$" and "scrambled (Ser)$_4$-VSG-117$_h$," respectively (Table 2). Scrambling the (Ala)$_4$-VSG-117$_h$ sequence reduced peak hydrophobicity by approximately 0.3 units (24% reduction), while "scrambled (Ser)$_4$-VSG-117$_h$" differed from (Ser)$_4$-VSG-117$_h$ by only 0.01 units (3% reduction) (FIG. 12A (panel "F"). Also, a variant of (Ala)$_4$-VSG-117$_h$ was created by exchanging tyrosine at position 10 for alanine at position 9, yielding (Ala)$_4$-Tyr$_9$-VSG-117$_h$ (Table 2). Because (Ala)$_4$-Tyr$_g$-VSG-117$_h$ was created from (Ala)$_4$-VSG-117$_h$ by switching the positions of two amino acids, the peak hydrophobicity was not affected (FIG. 12B). Since the amino acid composition of each sequence was not altered, any change in translocation competence would be attributable to amino acid sequence alterations.

Microsomal import assays comparing "scrambled" h-region mutants to their unscrambled counterparts showed a drastic reduction in the import of the "scrambled" mutants. (Ala)$_4$-VSG-117$_{86}$ was imported into TbRM at approximately 86% while only 14% of "scrambled (Ala)$_4$-VSG-117$_{86}$" was imported into TbRM (FIG. 12A (panels "B" and "C") and FIG. 12B). Approximately 70% of (Ser)$_4$-VSG-117$_{86}$ was imported into TbRM while 27% of "scrambled (Ser)$_4$-VSG-117$_{86}$" was imported into the microsomes (FIG. 12A (panels "D" and "E") and FIG. 12B). Similarly, 64% of (Ala)$_4$-Tyr$_g$-VSG-117$_{86}$ was imported into TbRM, whereas 84% of (Ala)$_4$-VSG-117$_{86}$ was translocated into TbRM (FIG. 12A (panels "B" and "F") and FIG. 12B). These data support the principle that arrangement of h-region amino acids is a crucial factor for translocation of VSG into TbRM.

Discovery of Peptide Motifs in T. brucei h-Regions. The data of this example indicated that h-region amino acid sequence was crucial to VSG import into TbRM (FIGS. 12A and 12B). However, an alignment of trypanosome signal peptides fails to unearth a consensus sequence. To resolve this conundrum, it was hypothesized that h-region amino acids formed peptide motifs that could not be discovered with sequence alignments. In an initial test of this hypothesis, 50 h-regions of secretory proteins from T. brucei were analysed. Through computational peptide pattern searches the motifs shown Table 3 were identified.

An h-region motif (h-motif) has three "identity components" and a "wild card region". There are two types of "identity components"; a "fixed identity component" is a unique amino acid, and a "variable identity component", which is a position that can be filled by one of a defined set of amino acids. The "wild card region" separates "identity components"; it can be one or multiple amino acids. For example, the h-motif L-x(1,2)-L-[AILV] possesses three "identity components". The first two are "fixed identity components", namely leucine (L), where the first leucine is separated from the second leucine by one or two "wild card" residues. The last "identity component" is a "variable identity component" that can be alanine (A) or isoleucine (I) or leucine (L) or valine (V) (i.e. [AILV]).

TABLE 2

| VSG | Position of Amino Acids in h-region Sequence |
|---|---|
| | 1 2 3 4 5 6 7 8 9 10 11 12 13 14 |
| VSG-117$_h$ | S T M L T S L L Y A I T P |
| Scrambled (Ala)$_4$-VSG-117$_h$ | A S L T A M A T S A Y I T P |
| Scrambled (Ser)$_4$-VSG-117$_h$ | S S L T S M S T S S Y I T P |
| (Ala)$_4$-VSG-117$_h$ | S T M A T L S A A Y A I T P |
| (Ala)$_4$-Tyr9-VSG-117$_h$ | S T M A T L S A Y A A I T P |

Amino Acid Sequences of VSG-117$_h$, scrambled (Ala)$_4$-VSG-117$_h$, scrambled (Ser)$_4$-VSG-117$_h$, (Ala)$_4$-VSG-117$_h$, and (Ala)$_4$-Tyr9-VSG-117$_h$.
The VSG-117$_h$ (SEQ ID NO:5), scrambled (Ala)$_4$-VSG-117$_h$ (SEQ ID NO:11), scrambled (Ser)$_4$-VSG-117$_h$ (SEQ ID NO:12), (Ala)$_4$-VSG-117$_h$ (SEQ ID NO:10), and (Ala)$_4$-Tyr9-VSG-117$_h$ (SEQ ID NO:13) mutants are aligned by h-region sequences.
Position 1 denotes the beginning of the h-region and position 14 marks its end.
h-Region sequence differences in (Ala)$_4$-VSG-117$_h$ and (Ala)$_4$-Tyr9-VSG-117$_h$ are listed in bold.

Three h-motifs were discovered in *T. brucei* (L-L-x-[AILV], L-x(1,2)-L-[AILV], and L-x(2,3)-L-[AILPV]) (Table 3). Of the 50 signal peptides, 37 (74%) contained at least one *T. brucei* h-motif. Most of the signal peptides contain multiple *T. brucei* h-motifs. This is exemplified by VSG-117, whose h-region contains one of each h-motif (Table 3). These h-motifs are different in organization and "identity component" composition from those h-motifs identified in yeast, *E. coli*, and humans.

Experimental Data Can Be Used to Expand "Identity Components" of Bioinformatically Identified h-Motifs. Existence of h-motifs does not prove their biological relevance. Thus, h-motifs are important for signal peptide activity. To evaluate this hypothesis, the four positions necessary to form every motif in the h-region of VSG-117 were mutated. Residues at h-region positions 4, 8, 9, and 11 (Leu$_4$, Leu$_8$, Leu$_9$, and Ala$_{11}$, respectively) were all changed to phenylalanine or valine (residues that were not discovered as "fixed identity components" in our data set), resulting in the new h-region mutants (Phe)$_4$-VSG-117$_h$ and (Val)$_4$-VSG-117$_h$, respectively (Table 4). Although the mutants lack h-motifs (Table 3), their hydrophobicities were similar to that of VSG-117$_h$ (FIG. 13B). Therefore, any reduction in protein import would be due principally to the loss of the h-motif. Both (Phe)$_4$-VSG-117$_{86}$ and (Val)$_4$-VSG-117$_{86}$ were imported into TbRM with similar efficiencies (78% and 83%, respectively) as compared to VSG-117$_{86}$ (99%) (FIG. 13A (panels "A," "B," and "C") and FIG. 13B. These data were compared with earlier ones (FIG. 10A (panels "B"-"F"), FIG. 10B, FIG. 13A (panels "A"-"C") and FIG. 13B) to obtain a general picture of the contributions of h-motifs to signal peptide activity.

The signal peptides of (Ala)$_4$-VSG-117$_{86}$ and (Ser)$_4$-VSG-117$_{86}$ were efficient at directing protein import into TbRM (FIG. 12A (panels B and D) and FIG. 12B). However, scrambling the h-region sequences of (Ala)$_4$-VSG-117$_{86}$ and (Ser)$_4$-VSG-117$_{86}$ caused a drastic reduction in the ability of these signal peptides to direct import into TbRM (FIG. 12A (panels C and E) and FIG. 12B). This indicated that the arrangement of h-region amino acids is crucial for signal peptide activity. Bioinformatic analysis of *T. brucei* signal peptides suggests that h-region amino acids are arranged into h-motifs where specific hydrophobic amino acids serve as "identity components" (Table 3). Data from "scrambled (Ala)$_4$-VSG-117$_{86}$" and "scrambled (Ser)$_4$-VSG-117$_{86}$" combined with bioinformatic data suggests that the rearrangement of h-region amino acids in "scrambled (Ala)$_4$-VSG-117$_{86}$" and "scrambled (Ser)$_4$-VSG-117$_{86}$" disrupted the arrangement of h-region amino acids serving as "identity components" in these h-motifs. This, in turn, affected the ability of these signal peptides to direct import into TbRM. Like (Ser)$_4$-VSG-117$_{86}$ and (Ala)$_4$-VSG-117$_{86}$, (Phe)$_4$-VSG-117$_{86}$ and (Val)$_4$-VSG-117$_{86}$, were imported into TbRM efficiently (FIG. 10A (panels C and F), FIG. 10B, FIG. 13A (panels A, B, and C) and FIG. 13B) while (Gly)$_4$-VSG-117$_{86}$, (Ala)$_7$-VSG-117$_{86}$, and (Ala)$_6$-Ile$_{12}$-VSG-117$_{86}$ were barely imported into TbRM (FIG. 10A (panels B, D, and E) and FIG. 10B).

TABLE 3

| Name | h-Motif | Location of Amino Acids in h-Motifs of VSG-117$_h$ |
|---|---|---|
| | | 1 2 3 4 5 6 7 8 9 10 11 12 13 14 |
| | | S T M L T S L L Y A I T P |
| Tb1 | L-L-x-[AILV] | L L x A |
| Tb2 | L-x(1, 2)-L-[AILV] | L x L L |
| Tb3 | L-x(2, 3)-L-[AILPV] | L x x x L L | h-Region Peptide Motifs in VSG-117.

The peptide motifs in the VSG-117 h-region are shown. Motifs are displayed in PROSITE syntax.

Peptide patterns were obtained from analysis of 50 *T. brucei* h-regions, using PRATT pattern matching tool (Jonassen et al., 1995, Protein Sci; 4(8):1587-95).

The PRATT parameters were determined empirically to identify patterns with three or more "identity components." The parameters were: C% (52); PL (50); PN (50); PX (5); FN (5); FL (2); FP (20); E (3).

The amino acid sequence STMLTLSLLYAITP is VSG-117$_h$ (SEQ ID NO:5), Tb1 (LLxA) is SEQ ID NO:14, Tb2 (LxLL) is SEQ ID NO:15, and Tb3 (LxxxLL) is SEQ ID NO:16.

However, all VSG-117$_h$ mutants with functional signal peptides or non-functional signal peptides lack *T. brucei* h-motifs identified by bioinformatics (compare sequences in Table 1 and 4 with motifs in Table 3). To reconcile this dilemma the bioinformatic and experimental data were combined, and the conclusion that "identity components" are important for efficient protein import into TbRM was drawn, and only a select set of amino acids can serve as "identity components" for a signal peptide to function. However, the data of this example indicate that *T. brucei* h-motifs allow hydrophobic residues (or serine residues) other than those found by bioinformatics to serve as "identity components."

TABLE 4

| VSG | Position of Amino Acids in h-region Sequence |  |  |  |  |  |  |  |  |  |  |  |  |  |
|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |
| VSG-117$_h$ | S | T | M | L | T | L | S | L | L | Y | A | I | T | P |
| (Phe)$_4$-VSG-117$_h$ | S | T | M | F | T | L | S | F | F | Y | F | I | T | P |
| (Val)$_4$-VSG-117$_h$ | S | T | M | V | T | L | S | V | V | Y | V | I | T | P |

Sequences of VSG-117$_h$, (Phe)$_4$-VSG-117$_h$, and (Val)$_4$-VSG-117$_h$ h-Regions.
Amino acids in VSG-117$_h$ (SEQ ID NO:5), (Phe)$_4$-VSG-117$_h$ (SEQ ID NO:17), and (Val)$_4$-VSG-117$_h$ (SEQ ID NO:18) are aligned by h-region sequences.
Position 1 is the beginning of the h-region and position 14 marks its end.
Mutations in the VSG h-regions are listed in bold.

VSG-117 h-Regions do Not Require Leucines. Mammalian h-regions are leucine-rich (von Heijne, 1981, *Eur J Biochem;* 116(2):419-22; von Heijne and Abrahmsen, 1989, *FEBS Lett;* 244(2):439-46; and Izard and Kendall, 1994, *Mol Microbiol;* 13(5):765-73). Experimental demonstration of a requirement for a leucine in a mammalian h-region was obtained in a study of *E. coli* proLamB. proLamB was nonfunctional at the canine microsome, but gained translocation activity into CfRM when leucine was substituted for alanine residues in its h-region (Zheng and Nicchitta, 1999, *J Biol Chem;* 274(51):36623-30). In an earlier study, replacement of glycine with leucine in the h-region of *S. cerevisiae* carboxypeptidase Y allowed the yeast protein to be imported into canine microsomes (Bird et al., 1987, *J Cell Biol;* 105(6 Pt 2):2905-14). The importance of leucine in trypanosome signal peptides has not been tested directly.

TABLE 5

| VSG | Position of Amino Acids in h-region Sequence |  |  |  |  |  |  |  |  |  |  |  |  |  |
|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |
| (Ala)$_4$-VSG-117$_h$ | S | T | M | A | T | L | S | A | A | Y | A | I | T | P |
| (Ala)$_4$-Phe6-VSG-117$_h$ | S | T | M | A | T | F | S | A | A | Y | A | I | T | P |
| (Ala)$_4$-Val6-VSG-117$_h$ | S | T | M | A | T | V | S | A | A | Y | A | I | T | P |
| (Ala)$_4$-Ile6-VSG-117$_h$ | S | T | M | A | T | I | S | A | A | Y | A | I | T | P |

Amino Acid Sequences of (Ala)$_4$-VSG-117$_h$, (Ala)$_4$-Phe6-VSG-117$_h$, (Ala)$_4$-Val6-VSG-117$_h$, and (Ala)$_4$-Ile6-VSG-117$_h$.
The h-Region sequences of (Ala)$_4$-VSG-117$_h$ (SEQ ID NO:10), (Ala)$_4$-Phe6-VSG-117$_h$ (SEQ ID NO:19), (Ala)$_4$-Val6-VSG-117$_h$ (SEQ ID NO:20), and (Ala)$_4$-Ile6-VSG-117$_h$ (SEQ ID NO:21) are aligned. Position 1 marks the beginning of the h-region and position 14 is its end.
Mutations to the VSG h-regions are listed in bold.

The majority of VSG-117 signal peptide variants that were imported into TbRM possessed at least one leucine in their h-regions. However, data from (Gly)$_4$-VSG-117$_{86}$, "scrambled (Ala)$_4$-VSG-117$_{86}$", and "scrambled (Ser)$_4$-VSG-117$_{86}$" showed that leucine is not sufficient for efficient VSG import into TbRM because each of these h-regions contained leucine, yet they were imported into TbRM in negligible amounts (FIG. 10A (panel "B"), FIG. 10B, FIG. 12A (panels "C" and "E") and FIG. 12B). Nevertheless, leucine is found in all h-motifs identified in *T. brucei* (Table 3). From these facts we hypothesized that while leucine is not sufficient for signal peptide activity, it could facilitate efficiency of h-region activity at TbRM. To investigate this idea new variants of (Ala)$_4$-VSG-117$_h$ were made where its sole leucine at position six was mutated to other hydrophobic amino acids, namely, phenylalanine, valine, or isoleucine, creating the mutants (Ala)$_4$-Phe$_6$-VSG-117$_h$, (Ala)$_4$-Val$_6$-VSG-117$_h$, and (Ala)$_4$-Ile$_6$-VSG-117$_h$, respectively (Table 5). Since (Ala)$_4$-VSG-117$_h$, (Ala)$_4$-Phe$_6$-VSG-117$_h$, (Ala)$_4$-Val$_6$-VSG-117$_h$, and (Ala)$_4$-Ile$_6$-VSG-117$_h$ only differed by one amino acid at position six their h-region peak hydrophobicity values were similar (FIG. 14B). Therefore, any difference in the extent of VSG import among these h-regions is not attributable to peak hydrophobicity.

The h-regions were imported into TbRM with different efficiencies; import efficiencies for (Ala)$_4$-Phe$_6$-VSG-117$_{86}$, (Ala)$_4$-Val$_6$-VSG-117$_{86}$, and (Ala)$_4$-Ile$_6$-VSG-117$_{86}$ were 71%, 54%, and 40%, respectively (FIG. 14A (panels "A," "B," "C," "D," and "E") and FIG. 14B). Therefore, while mutating leucine to phenylalanine altered VSG import efficiency into TbRM by 6%, substitution of leucine with valine or isoleucine caused significant reduction (14% or 28%, respectively) in the amount of VSG imported into TbRM (FIG. 14B).

This example demonstrates that leucine in the VSG-117 h-region is not essential for signal peptide activity; other hydrophobic residues can be used in the signal sequence. Further, as the hydrophobicity of the amino acid occupying position six of (Ala)$_4$-VSG-117$_h$ increased the efficiency of import decreased (FIG. 14A (panels "A," "B," "C," "D," and "E") and FIG. 14B, suggesting a hierarchy of hydrophobic residues (L≧F>V>I) in that position of the h-region.

Discussion

Arrangement of h-Region Amino Acids Is Important For Signal Peptide Function. Cell surface protein expression is essential for cell viability in all biological kingdoms. Instrumental to entry into the secretory pathway is protein translocation into the ER (reviewed by Shimizu and Hendershot, 2007, *Adv Exp Med Biol;* 594:37-46), a process that requires an ER signal peptide (reviewed by Schatz and Dobberstein, 1996, *Science;* 271(5255):1519-26; and Hegde and Bernstein, 2006, *Trends Biochem Sci;* 31(10):563-71). To date the best model available to explain signal peptide function relies heavily on h-region peak hydrophobicity as the determinant of activity (Ryan et al., 1986, *J Biol Chem;* 261(7):3389-95; Chou and Kendall, 1990, *J Biol Chem;* 265(5):2873-80; Doud et al., 1993, *Biochemistry;* 32(5):1251-6; Ryan et al., 1993, *Virus Genes;* 7(1):5-21; Tomilo et al., 1994, *J Biol Chem;* 269(50):32016-21; and Ng et al., 1996, *J Cell Biol;* 134(2):269-78). Although many experiments support this paradigm, there are numerous exceptions to this dogma (Abrahmsen et al., 1985, *EMBO J;* 4(13B):3901-6; Bird et al., 1987, *J Cell Biol;* 105(6 Pt 2):2905-14; Laforet et al., 1989, *J Biol Chem;* 264(24):14478-85; von Heijne and Abrahmsen, 1989, *FEBS Lett;* 244(2):439-46; Ryan and Edwards, 1995, *J Biol Chem;* 270(46):27876-9; Al-Qahtani et al., 1998, *Biochem J;* 331 (Pt 2):521-9; Matoba and Ogrydziak, 1998, *J Biol Chem;* 273(30):18841-7; and Ramirez et al., 1999, *J Eukaryot Microbiol;* 46(6):557-65). These observations bolster two ideas; one, h-region hydrophobicity alone is not sufficient to impart signal peptide function, and, two, the h-region sequence contains cryptic information that is crucial for signal peptide activity.

Three sets of data show that h-region peak hydrophobicity cannot predict import of VSG-117 h-region variants into TbRM (FIGS. 10A and 10B). First, introduction of four serine residues into specified positions of the VSG-117 h-region (Table 1) produced an h-region with one of the lowest peak hydrophobicity values in this study (FIG. 10B), yet it was imported into TbRM (FIG. 10A (panel "C") and FIG. 10B). In contrast, (Gly)$_4$-VSG-117$_{86}$ was imported into TbRM in negligible amounts even though the peak hydrophobicity of this h-region was very similar to that of (Ser)$_4$-VSG-117$_{86}$ (FIG. 10B). Further, (Ala)$_7$-VSG-117$_{86}$ and (Ala)$_6$-Ile$_{12}$-VSG-117$_{86}$ possessed even higher h-region peak hydrophobicities, but were not translocated convincingly (1% and 18%, respectively) (FIG. 10A (panels "D" and "E") and FIG. 10B). Second, import of "scrambled (Ser)$_4$-VSG-117$_{86}$" (FIG. 12A (panels "D" and "E") and FIG. 12B) was the most striking example of how h-region peak hydrophobicity does not solely govern signal peptide function. Peak hydrophobicity of "scrambled (Ser)$_4$-VSG-117$_h$" differed by only 0.01 from (Ser)$_4$-VSG-117$_h$, yet 27% of "scrambled (Ser)$_4$-VSG-117$_{86}$" was imported into TbRM while 70% of (Ser)$_4$-VSG-117$_{86}$ was imported into TbRM (FIG. 12A (panels "D" and "E") and FIG. 12B). Third, exchanging amino acids at positions Ala$_9$ and Tyr$_{10}$ in (Ala)$_4$-VSG-117$_{86}$ for Tyr$_9$ and Ala$_{10}$ in (Ala)$_4$-Tyr$_g$-VSG-117$_{86}$ (Table 2) did not alter the peak hydrophobicity of (Ala)$_4$-VSG-117$_{86}$ and (Ala)$_4$-Tyr$_g$-VSG-117$_{86}$, but caused a significant reduction in import (22%) of (Ala)$_4$-Tyr$_g$-VSG-117$_{86}$ into ThRM (FIG. 12A (panels "B" and "F") and FIG. 12B). These data make a compelling case that peak hydrophobicity of the h-region is not the sole determinant of signal peptide activity.

h-Regions Contain Amino Acid Motifs That Are Important for Biological Function of Signal Peptides. To discover what other information, apart from hydrophobicity, that might be present in h-regions this example used bioinformatic approaches (Jonassen et al., 1995, *Protein Sci;* 4(8):1587-95) to analyze h-regions from *T. brucei*, and discovered three motifs (Table 3). This observation supports the idea that h-region sequences are not random, as previously believed (reviewed by Zheng and Gierasch, 1996, *Cell;* 86(6):849-52).

The functional significance of h-motifs was evaluated experimentally by mutating "identity component" positions 4, 6, 8, 9, and 11 (Tables 1, 4, and 5). The data showed that hydrophobic amino acids at positions 4, 8, 9, and 11 could be replaced with other hydrophobic amino acids and also with serine (FIG. 10A (panels "B," "C," and "F"), FIG. 10B, FIG. 13A (panels "B," and "C") and FIG. 13B). Further, leucine at h-region position six could be functionally replaced with phenylalanine, valine, or isoleucine (FIG. 14A (panels "A," "B," "C," "D," and "E") and FIG. 14B). However, hydrophobicity of the amino acid occupying this position appeared to be inversely proportional to efficiency of VSG import for that h-region. This begs the question that if other hydrophobic amino acids and serine can serve as identity components why were they not found in the bioinformatic analysis? One possible explanation as to why h-motifs containing phenylalanine, valine, isoleucine, or serine were not identified (Table 3) is that proteins containing them were not a significant proportion of the *T. brucei* proteome. The bioinformatic analysis of this example would not score motifs from small sets because they did not comprise 52% (PRATT minimum percentage (C %)) of the total input data set.

Natural selection and signal peptide competition for ER entry could also explain why some h-motifs direct VSG import in vitro, but are not detected in trypanosome signal peptides. Mutations could have created h-region sequences that were preferred by the translocation machinery over other h-regions. Thus, while they still directed import in vivo these less efficient h-region sequences might have been out-competed by the more efficient signal peptides. Similarly, an example of signal peptide competition in *E. coli* showed that advantageous mutations in a signal peptide corresponded with preferential use of this more efficient signal peptide over its non-mutated counterpart to direct protein translocation (Chen et al., 1996, *J Bacteriol;* 178(23):6658-64). Alternatively, h-region sequences that direct import in vitro might be too efficient in vivo, out-competing signal peptides that direct import of proteins essential for viability, possibly causing cells to be non-viable. As such, these signal peptides would not be preserved during evolution.

Collectively, this example supports the arrangement of hydrophobic amino acid within an h-region is crucial for the biological activity of a signal peptide. This example demonstrates that h-region amino acids are arranged into motifs, and it is the presence of these h-motifs that direct protein translocation into the ER. In this scenario, h-regions are hydrophobic because they contain h-motifs that possess predominantly hydrophobic "identity components." The elucidation of h-motifs in signal peptides indicates that primary sequence has a role in signal peptide activity.

h-Motifs Interact With TM2b and/or TM7 of Sec61α. Signal peptides are proposed to have a high propensity to form α-helices (Bruch and Gierasch, 1990, *J Biol Chem;* 265(7):3851-8; Izard and Kendall, 1994, *Mol Microbiol;* 13(5):765-73). From chemical cross-linking studies in *S. cerevisiae*, and X-ray crystal structure of Sec61 it has been proposed that transmembrane domains (TMs) 2b and 7 of Sec61α are in proximity to signal peptides (Plath et al., 1998, *Cell;* 94(6):795-807; Van den Berg et al., 2004, *Nature;* 427(6969):36-44). However, it is not known what areas of signal peptide h-regions are contacted by Sec61α. With this example, helical-wheel modeling of the VSG-117 h-region was used to offer a structure-based explanation of how h-motifs might interact with the Sec61 translocon and confer biological function to a signal peptide.

Figure 15:
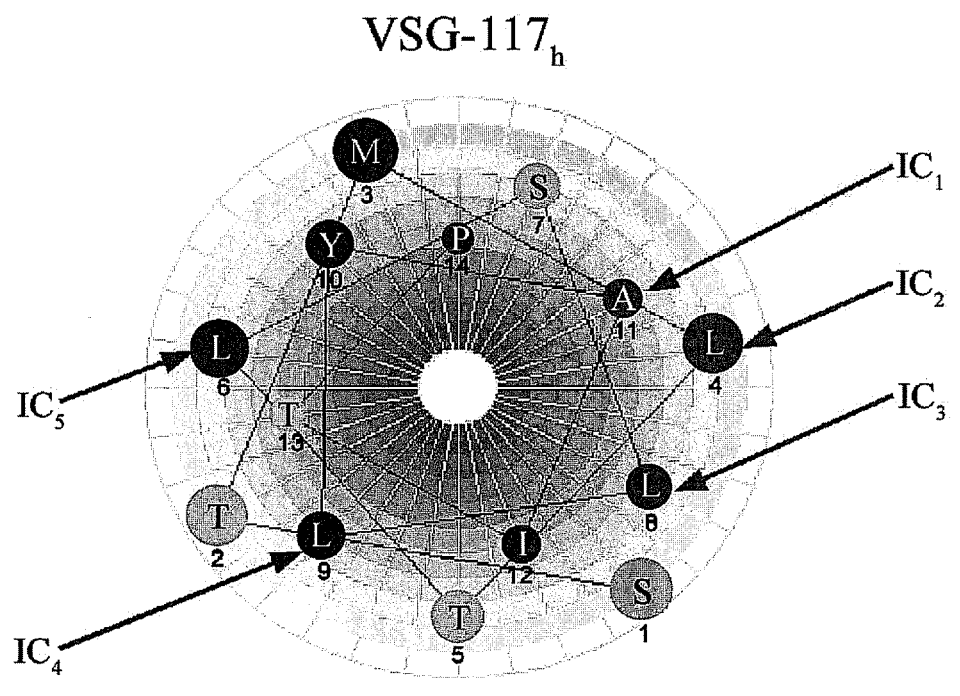

*T. brucei* h-motifs Tb1-3 (Table 3) specify positions 4, 6, 8, 9, and 11 of the VSG-117 h-region as "identity components." When the VSG-117 h-region is arranged into an α-helix, the "identity components" at h-region positions 4, 8, and 11 are placed on one side of an α-helix. Interestingly, the "identity components" at h-region positions 6 and 9 are positioned on the other half of the α-helix of the h-region (FIG. 15). Such positioning of h-motif "identity components" could allow amino acids at those positions to make concurrent contacts with transmembrane helices TM2b and/or TM7 of Sec61α (FIG. 51 and FIGS. 16A-16D) (Van den Berg et al., 2004, *Nature;* 427(6969):36-44). Chemical cross-linking studies and a Sec61-signal peptide model from yeast (Plath et al., 1998, *Cell;* 94(6):795-807) suggests that h-region amino acids on opposite sides of the signal peptide α-helix could make three contacts with TM2b of Sec61α and two contacts with TM7 of Sec61α. Using this as a model, it is apparent that the three h-region "identity components" in positions 4, 8, and 11 contact one half of the signal peptide-binding site of Sec61 (possibly at TM2b) while the two h-region "identity components" in positions 6 and 9 contact the other half of the Sec61α signal peptide-binding site (possibly at TM7) (FIGS. 16A-16D).

An ER signal peptide was once thought to be a random set of hydrophobic residues, but as supported by this example, turns out to be unexpectedly more complex than originally anticipated. Hydrophobic cores are non-charged "scaffolds" in which h-motifs, important for signal peptide function, are embedded.

Example 8

Drug Discovery with TbRM

The TbRM system of the present invention will advance our understanding of structure and function of trypanosome signal peptides that are important for targeting of nutrient receptors, virulence factors, and variant surface antigens to the plasma membrane of the parasite.

Using the methods described in more detail in the previous examples, which identified equisetin, CJ21,058, and MAL3-101 as new lead compounds for anti-trypanosome drug discovery, additional compounds will be screened, to identify additional lead compounds.

Example 9

Preparation of Microsomes from Other Parasitic Organisms

Using the methods described in more detail in Examples 1-6, for the preparation of microsomes from trypanosomes, microsomes will be prepared from other protozoan parasites, including, various *Leishmania* species, such as, for example, *Leishmania major*. Such microsomes may be used for the characterization of signaling sequences in the transport and translocation of proteins in protozoan parasites and in assays for the identification of lead compounds for the development of new drugs for the treatment and prevention of diseases caused by various parasitic organisms.

Example 10

A Full Length VSG__117 Construct and Drug Discovery at the Endoplasmic Reticulum of a Trypanosome With this example, a trypanosome microsomal system (TbRM) that imports full length VSG__117 post-translationally was developed. Using this system, MAL3-101, equisetin and CJ-21,058 functioned as small molecule inhibitors of VSG__117 translocation into the ER. These agents also killed blood stream *T. brucei* in vitro; the concentrations at which fifty percent of parasites was killed ($IC_{50}$) were 1.5 µM (MAL3-101), 3.3 µM (equisetin) and 7 µM (CJ-21,058), respectively. Thus, VSG__117 import into ThRM is a rapid and novel assay to identify "new chemical entities" for anti-trypanosome drug development and MAL3-101, equisetin, and CJ-21,058 as new lead compounds for anti-trypanosome drug discovery.

Materials and Methods

Reagents and Chemicals. Plasmid pVSG__117 (Bangs et al., 1996, *J Biol Chem;* 271(31):18387-93) served as a temple. The acyl tetramic acid (3-acyl-5-hydroxymethyl-2,4-dione) derivatives CJ-21,058 and equisetin were from Pfizer Inc. (New York, N.Y.). Rabbit reticulocyte lysate and methionine/cysteine-free amino acid mixture was purchased from Promega (Madison, Wis.). [$^{35}$S]Redivue Promix™ was purchased from Amersham Biosciences (Piscataway, N.J.), etoposide from Sigma (St. Louis, Mo.). Ampliscribe T7 In vitro transcription kit was purchased from Epicentre Technologies (Madison, Wis.).

DNA Templates and RNA Synthesis In vitro. DNA template (one µg) was transcribed using the Ampliscribe™ T7 kit (Epicentre Technologies) following the manufacturer's protocol. A template for in vitro transcription was obtained by PCR using the forward primer ccctaatacg actcactata gggag-gaggg tttttaccat ggactgccat acaaaggag (SEQ ID NO:1), which contains a T7 promoter and a translation enhancer. The first 21 nucleotides of the VSG__117 coding sequence are in regular style font. The forward primer for VSG__117$_{500}$ΔSP was ccctaatacg actcactata gggaggaggg tttttaccat ggccacactg agaaaggttgc (SEQ ID NO:24). It contained nucleotides 51-57 of the coding region. Other features are similar to those mentioned for the previous forward primer. The reverse primer for VSG__117$_{500}$ was catcatcatt tcctaaaaaa gcaaggc (SEQ ID NO:25). It contained nucleotides 516-525 of the coding region. The substrate for synthesis of VSG_MVAT7 was plasmid SL/3 (kindly provided by Dr. John Donelson, Univ. of Iowa).

The forward primer for the reaction was ccctaatacga ctcactatagg gaggagggtt tttaccatgt caacaagagt ccaacaa (SEQ ID NO:26). It contained a T7 promoter, a translational enhancer, and the first 21 nucleotides of VSG_MVAT7 coding sequence. One µl (1 MBU) of RNase free DNase I was added to the reaction mixture that was incubated at 37° C. for 15 minutes (1 MBU digests 1 µg of pUC19 DNA in 10 minutes ("min")). An equal volume of TE-saturated phenol/chloroform was then added to the reaction, which was agitated on a Vortex mixer, and centrifuged (13,200 rpm, 15 minutes) at 4° C. The aqueous phase was withdrawn, combined with an equal volume of chloroform, agitated on a Vortex mixer, and centrifuged (15 minutes, 13,200 rpm, 4° C.). To this aqueous phase 0.3M sodium acetate (final concentration) and precipitated with ethanol at −20° C. overnight. The precipitate was recovered by centrifugation (13,200 rpm, 4° C. for 15 minutes), rinsed with 70% ethanol, air-dried and dissolved 40 µl of nuclease free water. The RNA concentration was determined by measuring the absorbance at 260 µm, and confirmed by analysis with agarose gel electrophoresis/ethidium bromide staining.

Preparation of *T. brucei* Microsomes (TbRM). Blood stream trypanosomes were obtained from the blood of infected rats, and purified by DE-52 chromatography. Cells ($1 \times 10^{10}$) were resuspended in 5 ml of homogenization buffer (250 mM sucrose, 50 mM HEPES-KOH, 50 mM KOAc, 6 mM Mg(OAc)$_2$, 1 mM EDTA, 1 mM DTT, 1 µg/ml TLCK, 5 µg/ml leupeptin, 0.5 mM PMSF (final concentrations). Two and half ml of resuspended cells were added to a pre-chilled dounce homogenizer where they were lysed with 40 strokes of a tight-fitting pestle on ice. After a 1 minute rest, another after 40 strokes was delivered with the pestle. Homogenized cells were kept on ice while the remaining 2.5 ml of resuspended cells were broken. Both sets of homogenized lysates were pooled and centrifuged (2,000 rpm, 10 min, 4° C.) in microfuge tubes. The supernatants were pooled, aliquoted into new microfuge tubes, and centrifuged at 12,000 rpm for 20 min at 4° C., and pellets were resuspended in 40 µl (total volume) of fresh rough microsome buffer (RMB) (250 mM sucrose, 50 mM HEPES-KOH, 50 mM KOAc, 6 mM Mg(OAc)$_2$, 1 mM DTT, 0.5 µg/ml TLCK, 2.5 µg/ml leupeptin). The absorbance of the resuspended pellet (TbRM) was determined at 260 nm, and the concentration of TbRM was adjusted (with RMB) to OD$_{260}$ nm of 50. TbRM was aliquoted (20 µl portions), quick frozen in liquid nitrogen, and stored at −80° C. One equivalent of TbRM has an OD$_{260}$ of 50. Supernatant from the 12,000 rpm centrifugation step (above) was also saved (see below).

Preparation of Cytosol from *T. brucei*. The 12,000×g supernatant obtained during the preparation of TbRM (see above) was centrifuged at 65,000×g (60 min, 4° C., Beckman TLA 100.3 rotor). Two ml of the resulting supernatant was concentrated twenty-fold by ultrafiltration with a Centricon-10 filter (Amicon). The retentate was retrieved, an aliquot was diluted 50-fold with 0.1% SDS, and the OD$_{280}$ was measured. One equivalent of cytosol has an OD$_{280}$ of 50. Fifty microliter aliquots were quick-frozen in liquid nitrogen, and stored at −80° C.

Protein Import Into TbRM. Two µg of RNA encoding VSG__117 (or VSG_MVAT7) was translated in 30 µl of a reaction mixture containing 15 µl rabbit reticulocyte lysate, 60 μM amino acid mixture (-Met, -Cys), and 2.4 μCi [$^{35}$S] Promix. The reaction was incubated at 37° C. for 15 min. Cycloheximide (50 μg/ml, final concentration) was used to stop further translation, and the mixture was divided into two portions. *T. brucei* microsomes (TbRM) (1 equivalent) was added to one aliquot, and to the other portion an equal volume of RM buffer was added. The reactions were incubated at 37° C. for 45 min. To measure the post-translational import of VSG_117 into TbRM, each reaction mixture was divided into three portions (each 10 μl) and treated with one of the following on ice for one hour: (i) RM buffer; (ii) 30 μg/ml protease K; (iii) NP-40 (2%, final concentration) and protease K (30 μg/ml, final concentration). PMSF (20 mM final concentration) was added to stop protease K digestion. Samples were precipitated with an equal volume of cold $(NH_4)_2SO_4$ sulphate (saturated) and total proteins were resolved by SDS-PAGE (14% total acrylamide, 3% cross linker in Tricene-HCl system). The gels were dried, and radioactive polypeptides were detected with a phosphorimager (Personal Molecular Imager FX, (BioRad). Data were quantified with Quantity-One software (BioRad), and graphs were plotted with Delta-Graph (Red Rock software).

Results

*T. brucei* Microsomes (TbRM) Import Trypanosome VSGs. Microsomes from canine pancreas are a model system used to study protein import into the ER of eukaryotes. Unfortunately, signal sequences of *T. brucei* are generally incompatible with the protein import machinery of canine microsomes. Consequently, it was crucial to develop a trypanosomatid microsome system using ER membranes from *T. brucei* (TbRM) in order to study the ER import of a trypanosome protein. The substrate used for these studies was the VSG coat protein. Standard tests for successful microsomal ER protein import include: proteinase protection of the translocated protein, and loss of protease protection after detergent permeabilization of the microsomes. Native VSG protein is retained on membranes by a glycosylphosphatidylinositol (GPI) anchor at its C-terminus. All VSG constructs were engineered to produce "soluble secreted proteins" by addition of a stop codon upstream of the coding sequence for the GPI-signal peptide. Following import into ER microsomes, a soluble secreted protein is protected from exogenous protease by the ER membrane.

In this example, full-length VSG_117 was tested as a substrate protein for TbRM (see FIG. 17A for a flow chart of the protocol). In Example 2, truncated VSG_117$_{86}$ (86 amino acids long) was translocated in ThRM. However, full-length VSG_117 (500 amino acids long) was not imported into the microsomes (FIG. 17, lanes 1-3). Cytosolic chaperones that enable full-length proteins to maintain an "import-competent status" are required for post-translational import of proteins into the ER of yeasts. Therefore, it was suspected that full-length VSG_117 was not imported into TbRM because trypanosome chaperones were absent from the reaction mixture of reticulocyte lysate and TbRM. Thus, cytosol was prepared from *T. brucei* and evaluated its effect on translocation of full-length VSG_117 into TbRM.

Addition of *T. brucei* cytosol to TbRM led to protection of VSG_117 from protease K digestion (FIG. 17B, lanes 4 and 5). Detergent permeabilization of TbRM allowed proteinase K to digest VSG_117 in presence of cytosol (FIG. 17A, lane 6), indicating that the proteaseprotected full-length VSG_117 was imported into TbRM. Thus, cytosol from *T. brucei* is required for import of full-length VSG_117 into TbRM.

To test whether results with VSG_117 were applicable to other trypanosome proteins, this example also tested whether TbRM could import another full-length trypanosome protein VSG_MVAT7 (500 amino acids). This substrate was chosen because the VSG_MVAT7 signal peptide primary structure is different from that of VSG_117 (Al-Qahtani et al., 1998, *Biochem J;* 331 (Pt 2):521-9). Nevertheless, in the absence of TbRM, VSG_MVAT7 was degraded by proteinase K (FIG. 17C, lane 2), but the addition of cytosol and TbRM led to protection of VSG_MVAT7 from protease K (FIG. 17C, lane 5). Without cytosol the protein was not imported in TbRM. When detergent was introduced, proteinase K degraded the protected VSG_MVAT7 (FIG. 17, lane 6). Thus, VSG_MVAT7 is also imported into TbRM.

N-terminal signal sequences mediate import of proteins into the ER. Therefore the role of a signal sequence in VSG translocation into TbRM was evaluated with VSG_117$_{500}$ΔSP, which was obtained by deleting the signal peptide from VSG_117. VSG_117$_{500}$ΔSP was not protected from proteinase K in the presence of both ThRM and cytosol from *T. brucei* (FIG. 17D, compare lanes 3 and 4). Thus, an N-terminal signal peptide is essential for VSG_117 import into TbRM.

Proteins imported into the TbRM were not N-glycosylated because the molecular weight of the protease-protected VSGs was identical to the size of the protein synthesized in the absence of TbRM (FIG. 17B and FIG. 17C). However, absence of glycosylation does not mean that TbRM failed to import the proteins. Protein import into the ER and subsequent processing can be uncoupled, with oligosaccharyltransferase (OST) and signal peptidase acting after import of the substrate by the Sec61p complex. Thus it is likely that TbRM is deficient in OST activity, as has been observed in other in vitro ER systems. Nevertheless, the ThRM import assay of the present invention meets the "gold standard" for demonstrating the movement of a polypeptide into a membrane vesicle (or organelle), protease protection of the imported cargo, and digestion of the previously protected cargo by protease in the presence of detergent that permeabilizes the microsomal membrane.

MAL3-101 Inhibits VSG Translocation into TbRM. Posttranslational protein import into *S. cerevisiae* ER and across the *E. coli* inner membrane requires cytosolic chaperones or chaperone-like proteins, respectively. Since import of full-length VSG into *T. brucei* microsomes is posttranslational and dependent on cytosol, the possibility that the parasite cytosol contains Hsp70/Hsp40 that facilitate VSG_117 translocation into TbRM was considered. To explore this concept, it was tested whether VSG import into TbRM could be prevented by MAL3-101, a small molecule inhibitor of Hsp40-stimulated Hsp70 ATPase activity that blocks posttranslational import of pre-pro-alpha-factor (ppαMF) into microsomes from *S. cerevisiae*. Cytosol was pre-incubated with MAL3-101 (or an equal volume of DMSO) while VSG_117 mRNA was translated in a reticulocyte lysate. TbRM was then added to reticulocyte lysate that had been supplemented with cytosol (MAL3-101 or DMSO-treated) containing VSG and the mixture was incubated at 37° C. to promote import of VSG into the microsomes. Each mixture was treated with proteinase K (see FIG. 18A for flow chart of the protocol) in order to detect the imported VSG.

TbRM imported approximately 80% of VSG_117, as measured by protection from proteinase K digestion (FIG. 18B, compare lanes 1, 2), when only DMSO was added to the reaction mixture. In contrast, MAL3-101 inhibited translocation of VSG_117 into ThRM; only 13% of the protein was protected from proteinase K when MAL3-101 was present (FIG. 18B, lanes 3, 4). MAL3-51 (FIG. 5), which is structurally similar to MAL3-101 but has no effect on yeast translocation, had significantly less impact on import of VSG into TbRM even when used at a 3-fold higher concentration (FIG. 18B, lanes 5 and 6). These data indicate that the import of VSG_117 into TbRM is inhibited specifically by MAL3-101.

CJ-21,058 and Equisetin Inhibit Protein Translocation into TbRM. Post-translational protein translocation in *E. coli* requires SecA whose ATPase activity is inhibited by the small molecule CJ-21,058 (FIG. 5C). In *T. brucei*, cytosolic chaperones involved in ER protein import have not been completely characterized. The possible involvement of a SecA-like domain in polypeptide import into ThRM was tested using CJ-21,058 to pharmacologically challenge TbRM protein import.

CJ-21,058 inhibited import of VSG_117 into TbRM by 70%, compared to a DMSO control (FIG. 18B, compare lanes 1 and 2 to lanes 9 and 10). Similarly, equisetin, an analog of CJ-21,058 (FIG. 5D) inhibited VSG_117 translocation into TbRM by 95% (FIG. 18B, compare lanes 7 and 8). Thus, a protein with a SecA-like ATPase domain may contribute to the import of VSG_117 into TbRM. Nevertheless, the target of equisetin (and CJ-21,058) in the trypanosome system is not likely to be a protein with extensive sequence similarity to the SecA protein, for two reasons. First, a SECA gene is not encoded in the *T. brucei* genome. Second, sodium azide, an inhibitor of SecA, does not inhibit translocation of VSG_117 into ThRM. Interesting, SecA contains a DEAD-like domain that is also found in some proteins in *T. brucei* genome. Therefore, it is possible that equisetin inhibits the activity of a protein with this domain that is required for VSG import into the ER of *T. brucei*.

Discussion

Cell-free Protein Import Into Trypanosome ER Microsomes. This example developed a cell-free system using *T. brucei* microsomes (TbRM) into which trypanosome VSG_117 could be imported post-translationally (FIG. 17B and FIG. 17C) in a signal sequence dependent manner (FIG. 17D). Cytosol from *T. brucei* is needed for import of full-length VSGs into TbRM (FIG. 17B and FIG. 17C), reminiscent of the requirement for cytosol in the post-translational import of proteins into ER-derived microsomes from the fungi *S. cerevisiae* and *Candida maltosa*.

Factors involved in (or predicted to participate in) the import of proteins into the ER of *S. cerevisiae*, humans, and *T. brucei* include: KAR2 (BIP) (in *S. cerevisiae*, humans, and *T. brucei*); HSC70 (SSA1) (in *S. cerevisiae*, humans, and *T. brucei*); HSP40 (DJ1) (in *S. cerevisiae*, humans and *T. brucei*); SEC61α (Sec61p) (in *S. cerevisiae*, humans, and *T. brucei*); SEC61β (in *S. cerevisiae*, and humans); SEC61γ (in *S. cerevisiae*, humans, and *T. brucei*); SEC62 (in *S. cerevisiae* and humans); SEC63 (in *S. cerevisiae* and humans); SEC71 (in *S. cerevisiae*); SEC72 (in *S. cerevisiae*); SRP54 (in *S. cerevisiae*, humans, and *T. brucei*); SRP101 (Srα) (in *S. cerevisiae*, humans, and *T. brucei*); and SRP102 (Srβ) (in *S. cerevisiae* and humans). Some of the corresponding genes, for example SEC62, SEC63, SEC71 and SEC72, which are found in *S. cerevisiae* appear to be absent from the genomes of *T. brucei* and Archaea. The human genome lacks SEC71 and SEC72, whereas Archaea lack HSC70, a chaperone that is important for post-translational protein translocation in yeasts. However, absence of a protein homolog may preclude activity of a "functional analog" that may provide the needed biochemical function. In fact, for *T. brucei* there is precedent for this phenomenon; transferrin receptor and the nuclease Dicer lack sequence homology with their mammalian equivalents although the biochemical functions of the proteins are retained. In Archaea, proteins can be secreted post-translationally although the cells appear to lack cytoplasmic Hsp70 as well as Sec71/72p. Functional analogs of Hsp70 (or SecB) probably exist in Archaea. Alternatively, it is possible that the protein secretion pathways evolved independent of these factors.

In *T. brucei*, three lines of evidence support the existence of post-translational protein translocation into the ER, and suggest that this may be the most common route for entry into the secretory pathway. First, SRP is dispensable for protein import into the secretory pathway, suggesting the existence of an alternative (i.e., chaperone-dependent) route for protein entry into the organelle. Second, *T. brucei* genome lacks a gene for Srα (SRP102) (Table 1), which is one of the two subunits of the SRP receptor that is required for co-translational protein import into the ER. These facts suggest that the parasite may be unable to efficiently import proteins co-translationally into the ER. The caveat to this view is that a functional analog of SRα exists in *T. brucei*. Third, we demonstrate posttranslational import of VSG_117 into TbRM in vitro. These data are the most direct evidence that post-translational protein import into the ER can occur in vivo. If SRP is not involved in co-translational import into the ER of the trypanosome, why do the parasites have the genes encoding the complex? SRP has multiple functions in a cell. SRP can direct proteins that lack an N-terminal ER signal sequence to the ER post-translationally. Therefore, one cannot rule out a role for SRP in post-translational protein import into the ER of *T. brucei*.

The Secretory Pathway as a Target for Anti-Parasite Drug Discovery. Cell surface proteins, for example VSG, transferrin receptors, nucleobase transporters, and GP63 are important for establishing trypanosomatid infections in humans. Movement of these proteins to the plasma membrane is dependent on entry into the parasite ER, following paradigms worked out in model eukaryotes. The ER is a "gateway" for the transport of proteins to the Golgi, endosomes, lysosomes, and plasma membrane. Small molecules that interfere with import of proteins into the ER of a trypanosome may have value as anti-parasite agents. Moreover, mammals primarily translocate proteins into the ER by the co-translational route, so that compounds that interfere with post-translational ER protein import in *T. brucei* may compromise viability of the parasite without significant effect on mammalian cells. Data supporting this premise are provided in Example 2.

Molecular chaperones and chaperone-like proteins such as cytoplasmic Hsp70/Hsp40, ER luminal Kar2p/BiP (in eukaryotes), SecB and SecA (in eubacteria) are important for posttranslational protein import. Thus, small molecule modulators of Hsp70/Hsp40 might reduce post-translational import of VSG_117 into TbRM. MAL3-101 inhibits the cochaperone-stimulated ATPase of Hsp70 and inhibits translocation of pre-pro-alpha factor into yeast microsomes. When added to the TbRM protein import system, MAL3-101 (FIG. 5A) inhibited translocation of VSG_117 into parasite microsomes (FIG. 18B, lanes 3 and 4). Further, MAL3-101 killed *T. brucei* (Example 2). The efficacy of MAL3-101 against *T. brucei* ($IC_{50}$ was 1.5 µM) is comparable to that of suramin, a drug that is used to treat human African trypanosomiasis ($IC_{50}$ for suramin is 1.4-2.3 µM). These data indicate that MAL3-101 is a chemical entity that is worthy of optimization for anti-trypanosome drug discovery.

Equisetin (FIG. 5D) and CJ-21,058 (FIG. 5C), both fungal products inhibited import of VSG_117 into TbRM (FIG. 18), and the compounds were trypanocidal (Example 2). Fortunately, a total synthesis of equisetin has been described (Burke et al, 2000, Org Lett; 2:3611-3), an achievement that could guide future efforts, in the light of their anti-trypanosomal effects, to synthesize bioactive analogs for structure-activity studies on *T. brucei*. Finally, it will be interesting to test whether other equisetin-related compounds (e.g., altersetin, hexahydroaltersetin, dihydroaltersetin, tetrahydroequisetin, and phomasetin) (De Clercq, 2000, Med Res Rev; 20:323-49; Hellwig et al., 2002, *J Antibiot (Tokyo)*; 55:881-92; Tziveleka, 2003, Curr Top Med Chem; 3:1512-35) are trypanocidal.

Example 11

VSG Binding to *T. brucei* Microsomes (TbRM)

Proteins imported into the ER must first bind to the membrane of the organelle before translocation across the lipid bilayer. Further, the imported proteins remain associated with intact microsomal vesicles after their import into the ER. This example demonstrates an VSG__117 association with TbRM, an important step in the translocation pathway. In a "membrane flotation" study without TbRM, 90% of VSG__117 was detected in the 2.3 M sucrose layer, with only 5% in the 1.5 M sucrose layer where membranes sediment (FIG. 19C lanes 2 and 3). When TbRM was added to the mixture, 4-fold more VSG (i.e., 20%) was membrane-bound, in the 1.5 M sucrose cushion (FIG. 19D). This data is consistent with our earlier conclusions; VSG__117 binds to TbRM and is imported into the microsomes (Example 10).

Specifically, VSG-117 mRNA was translated in rabbit reticulocyte lysate for one hour at 37° C. Cycloheximide was added to stop protein synthesis. Two 5 µl aliquots of reaction mixture were aliquoted to new tubes. One aliquot was left untreated while 1 µl of TbRM was added to the other aliquot. The samples were incubated at 37° C. for 1.5 hours. Translocation was stopped by incubating the samples on ice. As shown in FIG. 19A, carbonate extraction of VSG-117 in the absence or presence of TbRM was performed using similar methods to those described in Zhang et al. (Zhang et al., 2001, *Mol Biol Cell;* 12(5):1303-14). Sodium carbonate (100 mM) was added to the samples and incubated on ice for 30 minutes. Next, the samples were centrifuged at 230,000×g for one hour. The supernatant from each sample was extracted, precipitated with ammonium sulfate for 30 minutes on ice, and pelleted at 16,060×g for 10 minutes at 4° C. The pellets from the 230,000×g and 16,060×g centrifugation steps were resuspended in SDS sample buffer, resolved by Tris-Tricine SDS-PAGE, and quantitated using a phosphorimager and Quantity One software. In FIG. 19A, lanes 1 and 2 represent VSG-117 carbonate extraction without TbRM. Lanes 3 and 4 represent VSG-117 carbonate extraction with TbRM present. "S" denotes proteins precipitated from the supernatant of the 230,000×g step while "P" represents proteins recovered from the 230,000×g centrifugation step. Brackets denote lanes that were compared to obtain a percentage to total VSG-117 present. FIG. 19B presents the quantitation of data from FIG. 19A. Percentage of total VSG-117 present is expressed as the amount of VSG detected in a single lane divided by the sum of the amount of VSG detected in the supernatant and pellet lanes.

In FIG. 19C the floatation of VSG-117 in the absence (top panel) or presence (bottom panel) of TbRM was performed, again using similar methods to those described by Zhang et al. [$^{35}$S]Met-labelled VSG117 was translated in a rabbit reticulocyte lysate and incubated with or without TbRM. Reaction mixtures were combined with 2.3 M sucrose in rough microsome buffer (RMB) (2.3 M Top) and layered onto a bottom layer of 2.3 M sucrose in RMB (2.3 M Bottom). Next, RMB containing 1.5 M sucrose was layered above the 2.3M layer, and RMB containing 0.25 M sucrose was layered above the 1.5 M layer. The sucrose gradient was then centrifuged at 100,000×g for five hours at 4° C. Each layer was then extracted, precipitated with ammonium sulfate, resuspended in SDS sample buffer, resolved using Tris-Tricine SDS-PAGE, and quantitated using a phosphorimager and Quantity One software. In FIG. 19C, lane 1 represents proteins obtained from the 0.25 M sucrose layer; lane 2 represents proteins obtained from the 1.5 M sucrose layer; lane 3 represents proteins obtained from the top 2.3 M sucrose layer; and lane 4 represents proteins recovered from the bottom 2.3 M sucrose layer and those protein pelleted from the 100,000×g centrifugation step. FIG. 19D presents a quantitation of data from FIG. 19C. The percentage of total VSG-117 present is expressed as the amount of VSG detected in a single lane divided by the sum of VSG detected in lanes 1-4. "*" Represents 0% VSG-117 detected.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified.

Sequence Listing Free Text

SEQ ID NO: 1-4, 22-26 synthetic oligonucleotide primers
SEQ ID NO:5-13, 17-21 amino acid sequences of VSG-117$_h$ constructs
SEQ ID NO:14-16 amino acid sequences of h-motifs

What is claimed is:

1. A composition comprising:
as one component an isolated cell free preparation of protozoan microsomes; the cell free preparation of protozoan microsomes the resuspended pellet of a low speed spin of about 5,000 g to about 20,000 g of a lysate of a protozoan of the genus *Trypanosoma* selected from the group consisting of *T. cruzi, T. brucei, T.b. gambiense*, and *T.b. rhodesiense*; and translocates a polypeptide into the microsome;
and as a second component an isolated purified cell free preparation of protozoan cytosol; the preparation of protozoan cytosol the supernatant of a high speed spin of greater than 20,000 g of a lysate of a protozoan of the genus *Trypanosoma* selected from the group consisting of *T. cruzi, T. brucei, T.b. gambiense*, and *T.b. rhodesiense*; and facilitates the translocation of a plasma membrane polypeptide into a cell free preparation of protozoan microsomes.

2. The composition of claim 1 wherein the translocated polypeptide is protected from exogenous detergent.

3. The composition of claim 1, wherein the composition facilitates the translocation of a VSG $117_{500}$ substrate into the cell free preparation of protozoan microsomes.

4. A composition comprising:
as one component an isolated cell free preparation of protozoan microsomes; the cell free preparation of protozoan microsomes the resuspended pellet of a low speed spin of about 5,000 g to about 20,000 g of a lysate of a protozoan of the genus *Trypanosoma*; and translocates a polypeptide into the microsome;
and as a second component an isolated purified cell free preparation of protozoan cytosol; the preparation of protozoan cytosol the supernatant of a high speed spin of greater than 20,000 g of a lysate of a protozoan of the genus *Trypanosoma*; and facilitates the translocation of a plasma membrane polypeptide into a cell free preparation of protozoan microsomes.

5. The composition of claim 4, wherein the composition facilitates the translocation of a VSG $117_{500}$ substrate into the cell free preparation of protozoan microsomes.

6. The composition of claim 4 wherein the translocated polypeptide is protected from exogenous detergent.

7. A method of endoplasmic reticulum (ER) translocation of a polypeptide; the method comprising contacting a polypeptide comprising a translocation signal sequence of protozoan origin with a composition of claim 1.

8. A method of screening for an agent that modulates the ER translocation of a polypeptide in a protozoan, the method comprising:
contacting the composition of claim 1 with an agent;
and monitoring ER translocation of a polypeptide comprising a translocation signal sequence of protozoan origin; wherein a modulation in the ER translocation of the polypeptide indicates the agent modulates ER translocation of a polypeptide in a protozoan.

9. A method of screening for an agent for the treatment and/or prevention of a protozoan infection, the method comprising: contacting the composition of claim 1 with an agent; and monitoring ER translocation of a polypeptide comprising a translocation signal sequence of protozoan origin; wherein a modulation in the ER translocation of the polypeptide indicates the agent is a candidate for the treatment and/or prevention of a protozoan infection.

10. The method of claim 9, wherein the modulation is a decrease or inhibition in the ER translocation of the polypeptide.

11. A method of screening for an agent that kills, inhibits the growth, and/or inhibits the reproduction of a protozoan, the method comprising:
contacting the composition of claim 1 with an agent;
and monitoring ER translocation of a polypeptide comprising a translocation signal sequence of protozoan origin; wherein a modulation in the ER translocation of the polypeptide indicates the agent is a candidate agent that kills, inhibits the growth, and/or inhibits the reproduction of a protozoan.

12. The method of claim 11, wherein the modulation is a decrease or inhibition in the ER translocation of the polypeptide.

13. The method of claim 7 wherein the translocated polypeptide is a soluble secreted polypeptide or a plasma membrane polypeptide.

14. The method of claim 7 wherein the translocated polypeptide is a polypeptide of nonprotozoan origin with a protozoan signal sequence.

15. The method of claim 8 wherein the translocated polypeptide is protected from exogenous detergent.

16. The method of claim 9 wherein the translocated polypeptide is protected from exogenous detergent.

17. The method of claim 11 wherein the translocated polypeptide is protected from exogenous detergent.

* * * * *